US 6,849,450 B2

(12) United States Patent
Langley et al.

(10) Patent No.: US 6,849,450 B2
(45) Date of Patent: Feb. 1, 2005

(54) ANTIBODIES TO THE METALLOPROTEINASE INHIBITOR

(75) Inventors: Keith E. Langley, Newbury Park, CA (US); Yves A. DeClerck, Los Angeles, CA (US); Thomas C. Boone, Newbury Park, CA (US)

(73) Assignees: Childrens Hospital of Los Angeles, Los Angeles, CA (US); Amgen Inc., Thousands Oaks, CA (US)

( * ) Notice: Subject to any disclaimer, the term of this patent is extended or adjusted under 35 U.S.C. 154(b) by 0 days.

(21) Appl. No.: 08/803,954

(22) Filed: Feb. 21, 1997

(65) Prior Publication Data

US 2002/0090654 A1 Jul. 11, 2002

Related U.S. Application Data

(60) Division of application No. 08/803,954, filed on Feb. 21, 1997, which is a division of application No. 08/212,660, filed on Mar. 11, 1994, now Pat. No. 5,714,465, which is a continuation of application No. 08/087,021, filed on Jul. 6, 1993, now abandoned, which is a continuation of application No. 07/710,728, filed on Jun. 3, 1991, now abandoned, which is a continuation-in-part of application No. 07/501,904, filed on Mar. 29, 1990, now abandoned, which is a continuation-in-part of application No. 07/355,027, filed on May 19, 1989.

(51) Int. Cl.[7] .............................................. C07K 16/38
(52) U.S. Cl. ................ 435/331; 530/388.26; 530/391.3
(58) Field of Search ........................... 530/387.1, 388.1, 530/388.26, 391.3, 350, 308.1; 435/338, 331, 326; 424/130.1; 514/2, 12

(56) References Cited

U.S. PATENT DOCUMENTS

| 4,710,473 A | 12/1987 | Morris ..................... 435/320.1 |
| 5,595,885 A | * 1/1997 | Stetler-Stevenson et al. ......... 435/69.2 |
| 5,698,671 A | * 12/1997 | Stetler-Stevenson et al. .......... 530/324 |

FOREIGN PATENT DOCUMENTS

| EP | A 0188342 | 7/1986 |
| EP | 0189784 | 8/1986 |
| EP | A 0404750 | 12/1990 |
| JP | A 63-210665 | 9/1988 |
| WO | WO 83/04053 | 11/1983 |
| WO | WO A 86/04608 | 8/1986 |
| WO | WO A 90/11287 | 10/1990 |
| WO | WO 90/14363 | 11/1990 |

OTHER PUBLICATIONS

Geysen et al. J. Molecular Recognition 1988.*
Clark et al. In "Enzyme–Immunoassay" Chapter 8, (ed. E.T. Maggio) CRC Press, Inc, Boca Raton, Fl, pp. 167–179. 1980.*
Murray et al. J. Biological Chemistry 261(1986) 4154–4159.*
Rudinger In "Peptide Hormones" (Jun. 1976) ed. J.A. Parsons, University Park Press, Baltimore, pp. 1–7.*
Suggs et al., "Use Of Synthetic Oligonucleotides As Hybridization Probes: Isolation Of Cloned cDNA Sequences For Human $\beta_2$–microglobulin," PNAS 78:6613–6617 (1981).
Young et al., "Efficient Isolation Of Genes By Using Antibody Probes," PNAS 80: 1194–1198 (1983).

(List continued on next page.)

Primary Examiner—Gary Kunz
Assistant Examiner—Robert C. Hayes
(74) Attorney, Agent, or Firm—Finnegan, Henderson, Farabow, Garrett & Dunner LLP

(57) ABSTRACT

A novel metalloproteinase inhibitor, analogs thereof, polynucleotides encoding the same, and methods of production, are disclosed. Pharmaceutical compositions and methods of treating disorders caused by excessive amounts of metalloproteinase are also disclosed.

4 Claims, 32 Drawing Sheets

OTHER PUBLICATIONS

Goldberg et al., "Human 72–kilodalton Type IV Collagenase Forms A Complex With A Tissue Inhibitor of Metalloproteases Designated TIMP–2," *PNAS* 86:8207–8211 (1989).
Aggeler et al., J. Cell. Biol. 98, 1662–1671 (1984).
Alvarez et al., J. National Cancer Inst., 589–595 (1990).
Andrews, Nature 295, 185–186 (1982).
Banda et al., Biochem. J., 193, 589–605 (1981).
Baron et al., Cell 28, 395–404 (1982).
Bauer et al., J. Exp. Med. 148, 1378–1387 (1978).
Birkedale–Hansen Methods Enzymol. 144, 140–171 (1987).
Bitter et al., Methods in Enzymol. 153, 516–544 (1987).
Blockinger and Diegelman, Mol. Cell. Biol. 4, 2929–2931 (1984).
Boone et al., Proc. Natl. Acad. Sci. USA 87, 2000 (1990).
Bradford Anal. Bioch. 72, 248–254 (1976).
Brown et al., American J. of Ophthalmology 72, 1139–1142 (1971).
Burnette, Anal. Biochem. 112, 195–203 (1981).
Carmichael et al., Proc. Natl. Acad. Sci. USA 83, 2407–2411 (1986).
Cawston et al. J. Biochem. 195, 159–165 (1981).
Cawston et al., J. Biochem. 211, 313–318 (1983).
Chen et al., Mol. Cell. Biol. 7, 2745–2752 (1987).
Chirgwin et al., Biochem. 18, 5294–5299 (1979).
De Clerck, Arch. Biochem. Biophys. 265, 28–37 (1988).
De Clerck et al., Cancer Research 46, 3580–3586 (1986).
De Clerk, Y.A. et al. (1989) J. Biol. Chem 264, 17445–17453.
Tooze, ed., *DNA Tumor Viruses,* Cold Spring Harbor Laboratories, Cold Spring Harbor, NY (1981), pp. 801–804.
Docherty et al., Nature 318, 65–69 (1985).
Dukes et al., Experimental Hematology 13, 59–66 (1985).
Ellman, G.L. Arch. Biochem. Biophys. 82, 70–771 (1984).
Evanson et al., J. Clin. Invest. 47, 2639–2651 (1968).
Fidler, Nature 242, 148–149 (1973).
Gasser et al., Proc. Natl. Acad. Sci. USA 79, 6522–6526 (1982).
Gelpi et al., Biochem. J. 283, 289–321 (1982).
Glorieux et al., Cancer 58, 2136–2139 (1986).
Graeve et al., Cancer 62, 2125–2127 (1988).
Grant et al., J. Biol. Chem. 262, 5886–5889 (1987).
Guarente et al., Proc. Natl. Acad. Sci. USA 79, 7410–7414 (1982).
Guarente et al., Cell 36, 503–511 (1984).
Herron et al., J. Biol. Chem. 261, 2814–2818 (1986).
Hewick et al., J. Biol. Chem. 256, 7990–7997 (1981).
Hibbs et al., J. Biol. Chem. 260, 2493–2500 (1985).
Hicks et al., Int. J. Cancer 33, 835–844 (1984).
Jiminez et al., Nature 287, 869–871 (1980).
Johnson–Wint, Anal. Biochem., 104, 175–181 (1980).
Jones and De Clerck, Cancer Res. 40, 3220–3227 (1980).
Jones et al., Cancer Res. 41, 4613–4620 (1981).
Kaiser et al., Science 223, 249–255 (1984).
Kaufman and Sharp, J. Mol. Biol. 159, 601–621 (1982).
Khokha et al., Science 243, 947–950 (1986).
Kohler and Milstein Eur. J. Immunol. 6, 511–519 (1976).
Laemmli Nature 227, 680–685 (1970).
Lathe, J. Mol. Biol. 183, 1–12 (1985).
Lerner et al., Cell 23, 309–310 (1981).
Lerner et al., Proc. Natl. Acad Sci. USA, 78, 3403–3407 (1981).
Lerner, Scientific American 248, 66–74 (1983).
Lin et al. Gene 44, 201–209 (1986).
Liotta et al., Biochem. Biophys. Res. Commun. 98, 124–198 (1981).
Liotta et al., Nature 284, 67–68 (1980).
Liotta et al., Proc. Natl. Acad. Sci. USA 76, 2268–2272 (1979).
Lu et al., J., Chromatog. 368, 215–231 (1986).
McCartney et al. Eur. J. Biochem. 130, 79–83 (1983).
Morrissey, Anal. Biochem. 117, 307–310 (1981).
Murphy et al., J. Biochem. 195, 167–170 (1981).
Murphy et al., Biochem. J. 192, 517–525 (1980).
Murray et al., J. Biol. Chem. 261, 4154–4159 (1986).
Nigg et al., PNAS USA, 79, 5322–5326 (1982).
Okayama and Berg, Mol. Cell. Biol. 3, 280–289 (1983).
Palmiter et al., Science 222, 809–814 (1983).
Pisko et al., J. Immunol. 136, 2141–2150 (1986).
Pozzatti et al., Science 232, 223 (1986).
Ross et al., Nature 294, 654–656 (1981).
Salo et al., J. Biol. Chem. 258, 3058–3063 (1983).
Sambrook et al., (1989) Molecular Cloning. A Laboratory Manual, pp. xi–xxxviii.
Sanger et al., PNAS USA 74, 5463–5467 (1977).
Schultz et al., Cancer Research 48, 5539–5545 (1988).
Schultz et al., Proteins: Structure, Function and Genetics 2, 290–297 (1987).
Seiki et al., PNAS USA 80, 3618–3622 (1983).
Slansky et al., Annals of Ophthalmology 2, 488–491 (1970).
Stetler–Stevenson et al., J. Biol. Chem. 264(29), 17374–17378 (1989).
Stetler–Stevenson et al., J. Biol. Chem. 265(23), 13933–13938 (1990).
Stricklin et al., J. Biol. Chem. 258, 12252–12258 (1983).
Takebe et al., Mol–Cell. Biol. 8, 466–472 (1988).
Thorgeirsson et al., J. Natl. Canc. Inst. 69, 1049–1054 (1982).
Tomayko and Reynolds, Cancer Chemother, Pharmacol. 24, 148 (1990).
Tramontano et al., (Nucleic Acid Res. 12, 5049–5059 (1984).
Tsai et al., J. Indust. Microbiol. 2, 181–187 (1987).
Tschumper et al., Gene 10, 157–166 (1980).
Tschumper et al., Gene 23, 221–232 (1983).
Tsu et al., "Solid Phase Radioimmunoassays", pp. 373–397 in Selected Methods in CellularImmunology, (1980).
Uitto, pp. 211–223 in *Proteinases in Inflammation and Tumor Invasion.* H. Tschesche, ed., Walter de Gruyter & Co., Berlin, N.Y. (1988).
Walter et al., PNAS USA 78, 4882–4886 (1981).
Walter et al., PNAS USA 77, 5197–5200 (1980).
Weiland et al., Blut 44, 173–175 (1982).
Werb et al., J. Exp. Med. 142, 346–360 (1975).
Williamson et al., Biochem. J. 268, 267–274 (1990).
Wooley et al., Arthritis and Rheumatism 20, 1231–1239 (1977).
Zoller and Smith Methods Enzymol. 154, 329–240 (1987).
Zsebo et al., J. Biol. Chem. 261, 5858–5865 (1986).

* cited by examiner att ccg gct tct atg gag cac tcg gga cca ggt ccg cgg cgc gcg cac tcg ctc gct cgc cgc ccc cca gcc agc tct cgc ttc cgc gcc gcc agc cgc gcc ccg cgc ctc ctc gct gca ccc cgc gac cta gag cca aga aag ttt gtg tgg cga gtg agg gcc gga gag gag agc gcg ccc gcg gag tgc cgt cca gac cag cgc ggc ccc ggc gga gag ggg agc gcc ccg agc cca ggc ggc ggc ggc tag ccc gag tcc gcg acc
        -26          -20
          Met Gly Ala Ala Ala Arg Ser Leu Pro Leu Ala Phe
ccc gcc cct ccg ccc gcc atg ggc gcc gcc gcc cgc agc ctg ccg ctc gcg ttc
     -10                 -1  1
Cys Leu Leu Leu Leu Gly Thr Leu Leu Pro Arg Ala Asp Ala Cys Ser Cys Ser
tgc ctc ctg ctg ctg ggg acg ctg ctc ccc cgg gcc gac gcc tgc agc tgc tcc
        10                20
Pro Val His Pro Gln Gln Ala Phe Cys Asn Ala Asp Ile Val Ile Arg Ala Lys
ccg gtg cac ccg caa cag gcg ttt tgc aat gca gac ata gtg atc agg gcc aaa
            30                40
Ala Val Asn Lys Lys Glu Val Asp Ser Gly Asn Asp Ile Tyr Gly Asn Pro Ile
gca gtc aat aag aag gag gtg gac tct ggc aac gac atc tac ggc aac ccc atc
                50
Lys Arg Ile Gln Tyr Glu Ile Lys Gln Ile Lys Met Phe Lys Gly Pro Asp Gln
aag cgg att cag tat gag atc aag cag ata aag atg ttc aag gga cct gat cag
    60                  70
Asp Ile Glu Phe Ile Tyr Thr Ala Pro Ala Ala Ala VAl Cys Gly VAl Ser Leu
gac ata gag ttt atc tac aca gcc ccc gcc gct gcc gtg tgt ggg gtc tcg ctg
        80                90
Asp Ile Gly Gly Lys Lys Glu Tyr Leu Ile Ala Gly Lys Ala Glu Gly Asn Gly
gac att gga gga aag aag gag tat ctc att gca ggg aag gcc gag ggg aat ggc
          100                110
Asn Met His Ile Thr Leu Cys Asp Phe Ile Val Pro Trp Asp Thr Leu Ser Ala
aat atg cat atc acc ctc tgt gac ttc atc gtg ccc tgg gac acc ctg agt gcc
            120                130
Thr Gln Lys Lys Ser Leu Asn His Arg Tyr Gln Met Gly Cys Glu Cys Lys Ile
acc cag aag aag agc ctg aac cac agg tac cag atg ggc tgt gag tgc aag atc
                 140
Thr Arg Cys Pro Met Ile Pro Cys Tyr Ile Ser Ser Pro Asp Glu Cys Leu Trp
act cga tgc ccc atg atc cca tgc tac atc tcc tct ccg gac gag tgc ctc tgg
  150                  160
Met Asp Trp Val Thr Glu Lys Asn Ile Asn Gly His Gln Ala Lys Phe Phe Ala
atg gac tgg gtc acg gag aag aac atc aac gga cac cag gcc aag ttc ttc gcc
      170                  180
Cys Ile Lys Arg Ser Asp Gly Ser Cys Ala Trp Tyr Arg Gly Ala Ala Pro Pro
tgc atc aag aga agc gac ggc tcc tgc gcc tgg tac cgc gga gca gca ccc ccc
            190     194
Lys Gln Glu Phe Leu Asp Ile Glu Asp Pro (SEQ ID NO: 7)
aag cag gag ttt ctg gac atc gag gac ccg taa gca ggc cac cag gac tcc tgg ggc caa ttg aca gtg tcc aag agt tca gac tgg tcc agc tcc gac atc cct tcc tgg aca cag cat gaa taa a (SEQ ID NO: 6)

FIG. 1

```
att ccg gcc cgc cgt ccc cca ccc cgc cgc ccc gcc cgg cga att gcg ccc cgc
gcc cct ccc ctc gcg ccc ccg aga caa aga gga gag aaa gtt tgc gcg gcc gag
cgg ggc agg tga gga ggg tga gcc gcg cgg gag ggg ccc gcc tcg gcc ccg gct
cag ccc ccg ccc gcg ccc cca gcc cgc cgc cgc gag cag cgc ccg gac ccc cca
                                                    -26
                                          Met Gly Ala Ala Ala Arg
gcg gcg gcc ccc gcc cgc cca gcc ccc cgg ccc gcc atg ggc gcc gcg gcc cgc
-20                                      -10
Thr Leu Arg Leu Ala Leu Gly Leu Leu Leu Leu Ala Thr Leu Leu Arg Pro Ala
acc ctg cgg ctg gcg ctc ggc ctc ctg ctg ctg gcg acg ctg ctt cgc ccg gcc
   -1  1                                10
Asp Ala Cys Ser Cys Ser Pro Val His Pro Gln Gln Ala Phe Cys Asn Ala Asp
gac gcc tgc agc tgc tcc ccg gtg cac ccg caa cag gcg ttt tgc aat gca gat
                20                                      30
Val Val Ile Arg Ala Lys Ala Val Ser Glu Lys Glu Val Asp Ser Gly Asn Asp
gta gtg atc agg gcc aaa gcg gtc agt gag aag gaa gtg gac tct gga aac gac
                    40                                      50
Ile Tyr Gly Asn Pro Ile Lys Arg Ile Gln Tyr Glu Ile Lys Gln Ile Lys Met
att tat ggc aac cct atc aag agg atc cag tat gag atc aag cag ata aag atg
                        60                                      70
Phe Lys Gly Pro Glu Lys Asp Ile Glu Phe Ile Tyr Thr Ala Pro Ser Ser Ala
ttc aaa ggg cct gag aag gat ata gag ttt atc tac acg gcc ccc tcc tcg gca
                                80
Val Cys Gly Val Ser Leu Asp Val Gly Gly Lsy Lsy Glu Tyr Leu Ile Ala Gly
gtg tgt ggg gtc tcg ctg gac gtt gga gga aag aag gaa tat ctc att gca gga
       90                                      100
Lys Ala Glu Gly Asp Gly Lys Met His Ile Thr Leu Cys Asp Phe Ile Val Pro
aag gcc gag ggg gac ggc aag atg cac atc acc ctc tgt gac ttc atc gtg ccc
           110                                      120
Trp Asp Thr Leu Ser Thr Thr Gln Lys Lys Ser Leu Asn His Arg Tyr Gln Met
tgg gac acc ctg agc acc acc cag aag aag agc ctg aac cac agg tac cag atg
                   130                                      140
Gly Cys Glu Cys Lys Ile Thr Arg Cys Pro Met Ile Pro Cys Tyr Ile Ser Ser
ggc tgc gag tgc aag atc acg cgc tgc ccc atg atc ccg tgc tac atc tcc tcc
                       150                                      160
Pro Asp Glu Cys Leu Trp Met Asp Trp Val Thr Glu Lys Asn Ile Asn Gly His
ccg gac gag tgc ctc tgg atg gac tgg gtc aca gag aag aac atc aac ggg cac
                           170
Gln Ala Lys Phe Phe Ala Cys Ile Lys Arg Ser Asp Gly Ser Cys Ala Trp Tyr
cag gcc aag ttc ttc gcc tgc atc aag aga agt gac ggc tcc tgt gcg tgg tac
   180                                      190              194
Arg Gly Ala Ala Pro Pro Lys Gln Glu Phe Leu Asp Ile Glu Asp Pro  (SEQ ID NO: 9)
cgc ggc gcg gcg ccc ccc aag cag gag ttt ctc gac atc gag gac cca taa gca ggc ctc caa cgc ccc tgt ggc caa ctg caa aaa aag cct cca agg gtt tcg act ggt cca gct ctg aca tcc ctt cct gga aac agc atg aat aaa aca ctc atc ccc gga att c (SEQ ID NO: 8)
```

```
          10         20         30         40         50         60
    CTAGAAAAAA CCAAGGAGGT AATAAATAAT GTGTTCTTGT TCTCCTGTAC ACCCTCAACA
    TTTTTT     GGTTCCTCCA TTATTTATTA CACAAGAACA AGAGGACATG TGGGAGTTGT 70         80         90        100        110        120
    AGCTTTTTGT AACGCTGATG TAGTTATCCG TGCAAAAGCT GTTTCTGAAA AAGAAGTTGA
    TCGAAAAACA TTGCGACTAC ATCAATAGGC ACGTTTTCGA CAAAGACTTT TTCTTCAACT.

130        140        150        160
    TTCTGGTAAC GACATCTACG GTAACCCGAT CAAAAG.
    AAGACCATTG CTGTAGATGC CATTGGGCTA GTTTTCCTAG
```

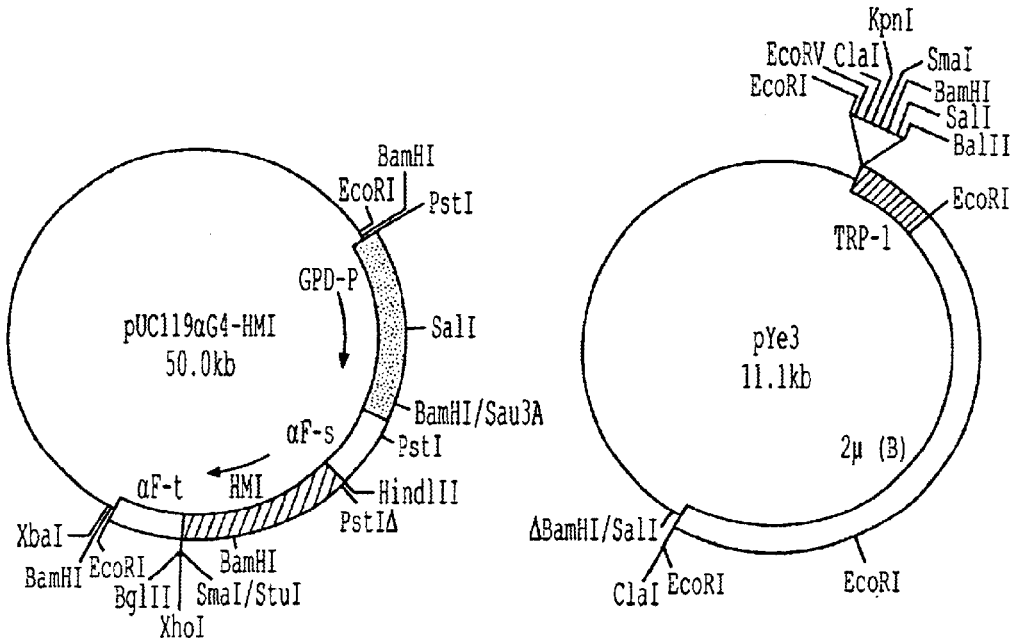
*FIG. 10A*  *FIG. 10B*
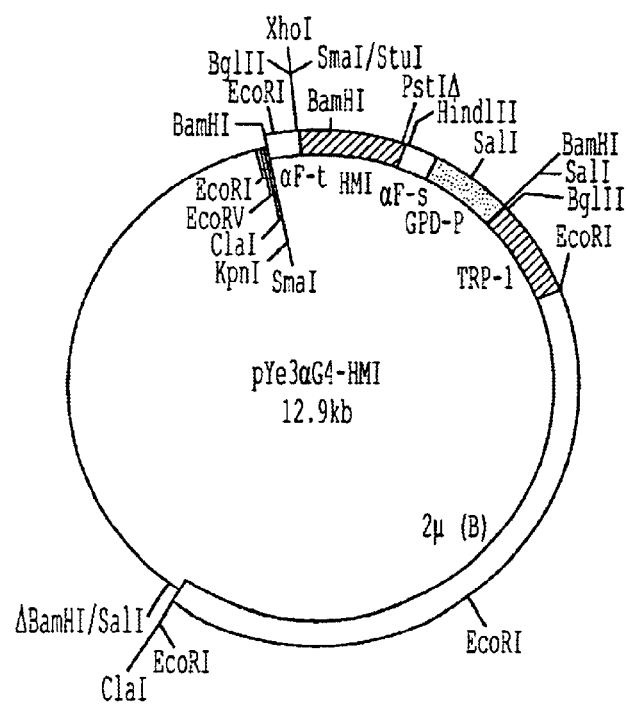
*FIG. 10C*

← smc

← smc

FIG. 28

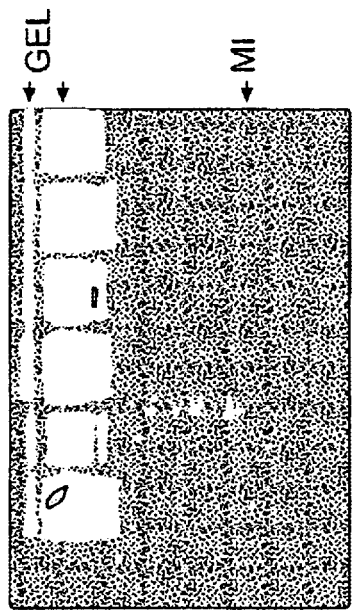
FIG. 29A  4R 8.60 m1 m2 m3 m4 m5
FIG. 29B
FIG. 29C  n1 n2 n3 n4 n5  −1.85  −1.3
FIG. 29D  MI 8.60 m1 m2 m3 m4 m5  −75  −50  −39  −27
FIG. 29E  GEL  MI Band 1: (Cys)-Ser-(Cys)-Ser-Pro-Val-His-Pro-Gln-Gln-Ala-Phe-
(Cys)-Asn-Ala-Asp-Val-Val-Ile- Band 1: Val-Val-Gly-Gly-Pro-(or Ala)-Val-Ala-His-Pro-His-Ser-
Trp-Pro-Thr-Gln-Val-Ser-Leu-Arg-Thr- Band 3: (Cys)-Ser-(Cys)-Ser-Pro-Val-

FIG. 32

ANTIBODIES TO THE METALLOPROTEINASE INHIBITOR

This application is a divisional of U.S. patent application Ser. No. 08/803,954, filed Feb. 21, 1997, which is a divisional of U.S. patent application Ser. No. 08/212,660, filed Mar. 11, 1994, now U.S. Pat. No. 5,714,465, which is a continuation of U.S. patent application Ser. No. 08/087,021, filed Jul. 6, 1993 now abandoned, which is a continuation of U.S. patent application Ser. No.07/710,728, filed Jun. 3, 1991, now abandoned, which is a continuation-in-part of U.S. patent application Ser. No. 07/501,904, filed Mar. 29, 1990, now abandoned, which is a continuation-in-part of U.S. patent application Ser. No. 07/355,027, filed May 19, 1989, pending, all of which are incorporated by reference herein.

The present invention relates in general to metalloproteinase inhibitors and to polynucleotides encoding such factors. In particular, the invention relates to a novel mammalian metalloproteinase inhibitor (MI), to fragments and polypeptide analogs thereof and to polynucleotides encoding the same.

BACKGROUND OF THE INVENTION

Connective tissues are maintained in dynamic equilibrium by the opposing effects of cellular connective tissue synthesis and extracellular degradation. The extracellular connective tissue matrix consists predominantly of collagens, with proteoglycans, fibronectin, laminin and other minor components making up the remainder.

Degradation of the matrix is brought about by the release of neutral metalloproteinases from resident connective tissue cells and invading inflammatory cells that are capable of degrading at physiological pH most of the matrix macromolecules. The proteinases include the mammalian tissue collagenases, gelatinases, and proteoglycanases; leukocyte collagenase and gelatinase [Murphy et al. Biochem. J. 283, 289–221 (1982); Hibbs et al., J. Biol. Chem. 260, 2493–2500 (1985)]; macrophage collagenase and elastase [Werb et al. J. Exp. Med. 142, 346–360 (1975); Banda et al., Biochem. J. 193, 589–605 (1981)]; and tumour collagenases [Liotta et al., Proc. Natl. Acad. Sci. USA 76 2268–2272 (1979); Liotta et al., Biochem. Biophys. Res. Commun. 98, 124–198 (1981); and Salo et al., J. Biol. Chem. 258, 3058–3063 (1983)]. For a general review of collagenases and their role in normal and pathological connective tissue turnover see *Collagenase in Normal and Pathological Connective Tissues,* David E. Woolley and John M. Evanson, eds., John Wiley & Sons Ltd. (1988).

There are over five different collagen types (I, II, III, IV, V, etc.) which are differently distributed among tissues. There is considerable homology and structural similarity among the various collagen types. Particular collagenases are specific for particular collagen types. With regard to inhibition of collagenases and other matrix-degrading metalloproteinases, it is possible that, depending on the actual enzymes, substrates, and inhibitory mechanisms, an inhibitor could act on just one, on several, or on all collagenases and metalloproteinases.

The underlying basis of degradative diseases of connective tissue points to the matrix-specific metalloproteinases as having a fundamental role in the aetiology of these diseases. Such diseases include dystrophic epidermolysis bullosa; rheumatoid arthritis; corneal, epidermal or gastric ulceration; peridontal disease; emphysema; bone disease; and tumor metastasis or invasion, and are discussed in more detail under the section Detailed Description of the Invention.

Most studies on connective tissue degradation and diseases involving such degradation have limited the measurement of metalloproteinases to collagenase (the most widely studied of this group of metalloproteinases). It is understood however, that the simultaneous effects of collagenase and the other matrix-degrading metalloproteinases will exacerbate the degradation of the connective tissue over that achieved by collagenase alone.

Specific natural inhibitors of collagenase were discovered in crude medium from cultured connective tissues. A metalloproteinase inhibitor known as TIMP (tissue inhibitor of metalloproteinases) has been studied with regard to physicochemical properties and the biochemistry of its interaction with collagenase [Murphy et al., J. Biochem. 195, 167–170 (1981); Cawston et al., J. Biochem. 211, 313–318 (1983); Stricklin et al. J. Biol. Chem. 258, 12252–12258 (1983)], and its gene has been isolated [Docherty et al. Nature 318, 65–69 (1985); Carmichael et al., Proc. Natl. Acad. Sci. USA 83, 2407–2411 (1986)]. In an in vitro cell culture model of tumor cell migration through a natural basement membrane, TIMP was able to arrest migration of a collagenase-secreting tumor cell line [Thorgeirsson et al., J. Natl. Canc. Inst. 69, 1049–1054 (1982)]. In vivo mouse lung colonization by murine B16-F10 melanoma cells was inhibited by injections of TIMP [Schultz et al., Cancer Research 48, 5539–5545 (1988)]. European patent application 189784 also relates to TIMP.

McCartney et al. [Eur. J. Biochem. 130, 79–83 (1983)] reported the purification of a metalloproteinase inhibitor from human leukocytes.

DeClerck et al. [Cancer Research 46, 3580–3586 (1986)] described the presence of two inhibitors of collagenase in conditioned medium from bovine aortic endothelial cells.

Murray et al. [J. Biol. Chem. 261, 4154–4159 (1986)] reported the purification and partial amino acid sequence of a bovine cartilage-derived collagenase inhibitor. The amino-terminal amino acid sequence of bovine MI of the subject invention is very similar to that reported by Murray et al. for the bovine cartilage-derived collagenase inhibitor (94% homology over first 38 residues), and the amino acid compositions are similar also. Murray et al. (J. Biol. Chem., supra) pointed out that the bovine cartilage-derived inhibitor had greater than 65% homology to human TIMP over the first 23 residues and that the amino-terminal sequences were "quite similar." Until the present work, no additional molecules related to or homologous to TIMP had ever been isolated from the same species from which a TIMP had been isolated. In the present work, two metalloproteinase inhibitors have been isolated and purified, and extensively characterized, from the same species (bovine) and indeed from the same cell conditioned medium. It is therefore clear that although they are related, as indicated, they cannot both be the bovine homolog of TIMP. One of them (peak II-derived), also as indicated, is probably bovine TIMP. The other (peak I-derived) must consequently be a new and additional molecule. Based on this discovery, it is apparent, for the first time, that there is a homologous inhibitor additional to TIMP encoded by the human genome. This human gene, i.e., the human MI gene, is set forth in Example 3.

To the extent that metalloproteinase inhibitors such as those described herein may prove to be therapeutically significant and hence need to be available in commercial scale quantities, isolation from cultures of naturally-occurring cells is unlikely to provide an adequate source of materials.

SUMMARY OF THE INVENTION

According to the present invention, a novel metalloproteinase inhibitor (MI), as well as analogs of MI, are provided. Also provided are DNA sequences coding for all or part of MI, vectors containing such DNA sequences, and host cells transformed or transfected with such vectors. Also comprehended by the invention are methods of producing recombinant MI, and methods of treating disorders. Additionally, pharmaceutical compositions including MI and antibodies specifically binding MI are provided.

BRIEF DESCRIPTION OF THE DRAWINGS

Note that in all Figures showing sodium dodecyl sulfate (SDS)-polyacrylamide gel electrophoresis (PAGE), numbered marks at the left represent migration positions of standards having molecular weights of $10^3$ times the indicated numbers. These markers were phosphorylase b ($M_r$ of 97,400), bovine serum albumin (BSA; $M_r$ of 66,200), ovalbumin ($M_r$ of 42,700) carbonic anhydrase ($M_r$ of 31,000), soybean trypsin inhibitor ($M_r$ of 21,500), and lysozyme ($M_r$ of 14,400). The standards were always reduced, even when some other samples run on the same gel were unreduced.

FIG. 1 shows the cDNA sequence (SEQ ID NO: 6) and amino acid sequence (SEQ ID NO: 7) of bovine metalloproteinase inhibitor.

FIG. 2 shows the cDNA sequence (SEQ ID NO: 8) and amino acid sequence (SEQ ID NO: 9) of human metalloproteinase inhibitor.

FIG. 9 shows a synthetic DNA fragment (SEQ ID NOs: 35 and 36) constructed for use in the expression of recombinant human metalloproteinase inhibitor in *E. coil*, containing a ribosome binding site, an initiation methionine codon and codons for the first 42 amino acids of the mature protein.

FIGS. 10A, B, C show vectors used for expression of recombinant human metalloproteinase inhibitor in yeast.

FIG. 28 shows Northern blot analysis for production of MI messenger RNA in transfected 4R cells.

FIGS. 29A, B, C, D, and E show Northern blot, immunoblotting, and gelatin substrate SDS-PAGE analyses of metastatic lung nodules from 8.60 cells injected intravenously in nude mice.

FIG. 32 shows results of amino terminal amino acid sequencing of peptides (SEQ ID No.: 2, SEQ ID No.: 3, SEQ ID No.: 4, SEQ ID No.: 5) of the SDS PAGE bands 1, 2, and 3 that were generated by plasmin digestion of CHO-derived human MI.

Figure 3:
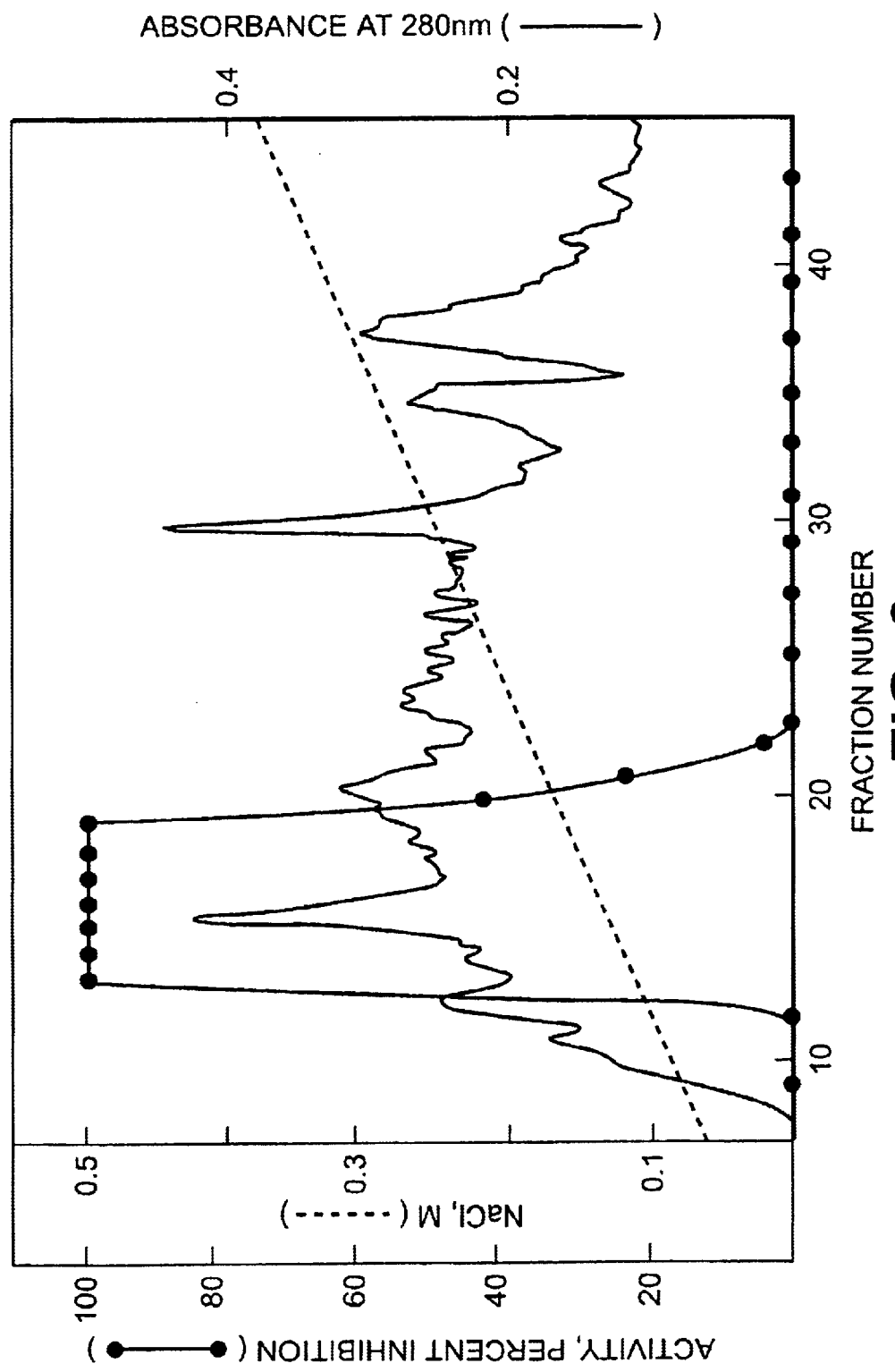
FIG. 3 shows anion exchange chromatography used in purification of bovine peak I-derived metalloproteinase inhibitor (MI).

Numerous aspects and advantages of the invention will be apparent to those skilled in the art upon consideration of the following detailed description which provides illustrations of the practice of the invention in its presently preferred embodiments.

DETAILED DESCRIPTION OF THE INVENTION

According to the present invention, a novel protein metalloproteinase inhibitor (MI) and DNA sequences coding for all or part of such MI are provided. Such sequences include: the incorporation of codons "preferred" for expression by selected nonmammalian hosts; the provision of sites for cleavage by restriction endonuclease enzymes; and the provision of additional initial, terminal or intermediate DNA sequences which facilitate construction of readily expressed vectors. The present invention also provides DNA sequences coding for polypeptide analogs or derivatives of MI which differ from naturally-occurring forms in terms of the identity or location of one or more amino acid residues (i.e., deletion analogs containing less than all of the residues specified for MI; substitution analogs, wherein one or more residues specified are replaced by other residues; and addition analogs wherein one or more amino acid residues is added to a terminal or medial portion of the polypeptide) and which share some or all the properties of naturally-occurring forms.

Novel DNA sequences of the invention include sequences useful in securing expression in procaryotic or eucaryotic host cells of polypeptide products having at least a part of the primary structural conformation and one or more of the biological properties of naturally-occurring MI. DNA sequences of the invention specifically comprise: (a) the DNA sequence set forth in FIG. 1 or FIG. 2 or their complementary strands; (b) a DNA sequence which hybridizes (under hybridization conditions disclosed in Example 3) or more stringent conditions to the DNA sequence in FIG. 1 or FIG. 2 or to fragments thereof; and (c) a DNA sequence which, but for the degeneracy of the genetic code, would hybridize to the DNA sequence in FIG. 1 or FIG. 2. Specifically comprehended in parts (b) and (c) are genomic DNA sequences encoding allelic variant forms of MI and/or encoding MI from other mammalian species, and manufactured DNA sequences encoding MI, fragments of MI, and analogs of MI which DNA sequences may incorporate codons facilitating transcription and translation of messenger RNA in microbial hosts. Such manufactured sequences may readily be constructed according to the methods of Alton et al., PCT published application WO 83/04053.

According to another aspect of the present invention, the DNA sequences described herein which encode MI polypeptides are valuable for the information which they provide concerning the amino acid sequence of the mammalian protein which have heretofore been unavailable. The DNA sequences are also valuable as products useful in effecting the large scale synthesis of MI by a variety of recombinant techniques. Put another way, DNA sequences provided by the invention are useful in generating new and useful viral and circular plasmid DNA vectors, new and useful transformed and transfected procaryotic and eucaryotic host cells (including bacterial and yeast cells and mammalian cells grown in culture), and new and useful methods for cultured growth of such host cells capable of expression of MI and its related products.

DNA sequences of the invention are also suitable materials for use as labeled probes in isolating human genomic DNA encoding MI and related proteins as well as cDNA and genomic DNA sequences of other mammalian species. DNA sequences may also be useful in various alternative methods of protein synthesis (e.g., in insect cells) or in genetic therapy in humans and other mammals. DNA sequences of the invention are expected to be useful in developing transgenic mammalian species which may serve as eucaryotic "hosts" for production of MI and MI products in quantity. See, generally, Palmiter et al., Science 222, 809–814 (1983).

The present invention provides purified and isolated polypeptide products having part or all of the primary structural conformation (i.e., continuous sequence of amino acid residues) and one or more of the biological properties (e.g., immunological properties and in vitro biological activity) and physical properties (e.g., molecular weight) of naturally-occurring MI including allelic variants thereof. The term "purified and isolated" as used herein means substantially homogeneous or purified to apparent homogeneity (e.g., one band by SDS-PAGE). These polypeptides are also characterized by being the natural purified product, or the product of chemical synthetic procedures or of procaryotic or eucaryotic host expression (e.g., by bacterial, yeast, higher plant, insect and mammalian cells in culture) of exogenous DNA sequences obtained by genomic or cDNA cloning or by gene synthesis. The products of expression in typical yeast (e.g., *Saccharomyces cerevisiae*) or procaryote (e.g., *E. coli*) host cells are free of association with any mammalian proteins. The products of expression in vertebrate (e.g., non-human mammalian (e.g. COS or CHO) and avian) cells are free of association with any human proteins. Depending upon the host employed, polypeptides of the invention may be glycosylated with mammalian or other eucaryotic carbohydrates or may be non-glycosylated. Polypeptides of the invention may also include an initial methionine amino acid residue (at position −1).

In addition to naturally-occurring allelic forms of MI, the present invention also embraces other MI products such as polypeptide analogs of MI and fragments of MI. Following the procedures of the above-noted published application by Alton et al. (WO 83/04053), one can readily design and manufacture genes coding for microbial expression of polypeptides having primary conformations which differ from that herein specified for in terms of the identity or location of one or more residues (e.g., substitutions, terminal and intermediate additions and deletions). Alternately, modifications of cDNA and genomic genes may be readily accomplished by well-known site-directed mutagenesis techniques and employed to generate analogs and derivatives of MI. Such products would share at least one of the biological properties of MI but may differ in others. As examples, projected products of the invention include those which are foreshortened by e.g., deletions; or those which are more stable to hydrolysis (and, therefore, may have more pronounced or longer lasting effects than naturally-occurring); or which have been altered to delete one or more potential sites for O-glycosylation (which may result in higher activities for yeast-produced products); or which have one or more cysteine residues deleted or replaced by, e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within MI, which fragments may possess one activity of MI (e.g., receptor binding) and not others (e.g., metalloproteinase inhibiting activity). It is noteworthy that activity is not necessary for any one or more of the products of the invention to have therapeutic utility [see, Weiland et al., Blut 44, 173–175 (1982)] or utility in other contexts, such as in assays of MI antagonism. Competitive antagonists may be quite useful in, for example, cases of overproduction of MI.

Of applicability to MI fragments and polypeptide analogs of the invention are reports of the immunological activity of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically significant proteins such as viral antigens, polypeptide hormones, and the like. Included among the immune reactions of such polypeptides is the provocation of the formation of specific antibodies in immunologically active animals. See, e.g., Lerner et al., Cell 23, 309–310 (1981); Ross et al., Nature 294, 654–656 (1981); Walter et al., Proc. Natl. Acad. Sci. USA 77, 5197–5200 (1980); Lerner et al., Proc. Natl. Acad. Sci. USA, 78 3403–3407 (1981); Walter et al., Proc. Natl. Acad. Sci. USA 78, 4882–4886 (1981); Wong et al., Proc. Natl. Acad. Sci. USA, 79 5322–5326 (1982); Baron et al., Cell 28, 395–404 (1982); Dressman et al., Nature 295, 185–160 (1982); and Lerner, Scientific American 248, 66–74 (1983). See, also, Kaiser et al. [Science 223, 249–255 (1984)] relating to biological and immunological activities of synthetic peptides which approximately share secondary structures of peptide hormones but may not share their primary structural conformation.

The present invention also includes that class of polypeptides coded for by portions of the DNA complementary to the protein-coding strand of the human cDNA or genomic DNA sequences of MI i.e., "complementary inverted proteins" as described by Tramontano et al. [Nucleic Acid Res. 12, 5049–5059 (1984)].

Also comprehended by the invention are pharmaceutical compositions comprising effective amounts of polypeptide products of the invention together with suitable diluents, preservatives, solubilizers, emulsifiers, adjuvants and/or carriers useful in MI therapy. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); covalent attachment of polymers such as polyethylene glycol to the protein (see for example U.S. Pat. No. 4,179,337 hereby incorporated by reference); incorporation of the material into particulate preparations of polymeric compounds such as polylactic acid, polyglycolic acid, etc. or into liposomes. Such compositions will influence the physical state, stability, rate of in vivo release, and rate of in vivo clearance of MI.

The invention also comprises compositions including an additional metalloproteinase inhibitor such as TIMP or low molecular weight chemical inhibitors. It also comprises compositions including additional agents influencing progression of a disease state, e.g., laminin- and/or fibronectin-derived peptides which like MI can impede cancer metastasis.

Polypeptide products of the invention may be "labeled" by association with a detectable marker substance (e.g., radiolabeled with $^{125}$I) to provide reagents useful in detection and quantification of MI in solid tissue and fluid samples such as blood or urine. Nucleic acid products of the invention may also be labeled with detectable markers (such as radiolabels and non-isotopic labels such as biotin) and employed in hybridization processes to locate the human MI gene position and/or the position of any related gene family in a chromosomal map. They may also be used for identifying human MI gene disorders at the DNA level and used as gene markers for identifying neighboring genes and their disorders.

MI when used in pharmacological formulation modifies the pathogenesis and provides a beneficial therapy for diseases of connective tissues characterized by matrix degradation. Also, metalloproteinase inhibitor is useful in the treatment of any disorder where excessive matrix loss is caused by metalloproteinase activity, and in the promotion of wound healing following surgery or other wound situations.

Polypeptide products of the present invention are useful, alone or in combination with other drugs, in the treatment of various disorders such as dystrophic epidermolysis bullosa where the disease is linked to the overproduction of collagenase [Bauer et al., J. Exp. Med. 148, 1378–1387 (1978)]. The products of the present invention are also useful in the treatment of rheumatoid arthritis. Evanson et al. [J. Clin. Invest. 47, 2639–2651 (1968)] noted that large amounts of collagenase are produced, in culture, by excised rheumatoid synovial tissue; this led to immunolocalization studies, by Woolley et al. [Arthritis and Rheumatism 20, 1231–1239 (1977)] with monospecific antibodies directed against human rheumatoid synovial collagenase which detected high levels of immunoreactive collagenase at the sites of joint erosion (cartilage-pannus junctions) but not in the cartilage of associated chondrocytes, and not in the synovium at sites remote from the resorbing front. Collagenases have also been demonstrated using many other different preparations derived from human rheumatoid joints and using tissues characterized by other types of arthritis such as osteoarthritis, Reiter's syndrome, pseudogout, juvenile rheumatoid arthritis, and scleroderma.

In periodontal disease affecting the tooth supporting apparatus, elevation of collagenolytic enzymes is evident, and destruction of collagen and connective tissue [see V.-J. Uitto, pp. 211–223 in *Proteinases in Inflammation and Tumor Invasion*, H. Tschesche, ed., Walter de Gruyter & Co., Berlin, N.Y. (1988)].

Collagenases have been implicated in ulceration including corneal, epidermal, or gastric ulceration [Brown et al., American J. of Ophthalmology 72, 1139–1142 (1971)] and, indeed, metalloproteinase inhibitors are used in the treatment of corneal ulceration [Slansky et al., Annals of Ophthalmology 2, 488–491 (1970)].

In the field of tumor invasion and metastasis, the metastatic potential of some particular tumors correlates with the increased ability to synthesize and secrete collagenases [Liotta et al., Nature 284, 67–68 (1980)], and with the inability to synthesize and secrete significant amounts of a metalloproteinase inhibitor [Hicks et al., Int. J. Cancer 33, 835–844 (1984)]. These processes are related to the passage of tumor cells through connective tissue layers (basement membrane) from tissue sites to the circulation and vice-versa, which could be retarded by MI. MI similarly has therapeutic application in inhibiting tumor cell dissemination during removal of primary tumors, during chemotherapy and radiation therapy, during harvesting of contaminated bone marrow, and during shunting of carcinomatous ascites.

A limiting factor in the use of bone marrow transplantation for many advanced cancers with bone marrow involvement is the absence of adequate purging techniques. For example, metastatic interstitial pneumonitis following infusion of improperly purged bone marrow cells has been noted [Glorieux et al., Cancer 58, 2136–2139 (1986); Graeve et al., Cancer 62, 2125–2127 (1988)]. MI administered during infusion of unpurged bone marrow cells will alleviate the need for developing expensive purging techniques.

Diagnostically, correlation between absence of MI production in a tumor specimen and its metastatic potential is useful as a prognostic indicator as well as an indicator for possible prevention therapy.

Tumors may also become more or less encapsulated or fibrotic due to increased collagen deposition (or inhibition of breakdown) by both cancer cells and/or surrounding normal cells. Increased encapsulation promoted by MI aids in clean tumor excision.

Other pathological conditions in which excessive collagen degradation may play a role and thus where MI can be applied, include emphysema, Paget's disease of bone, osteoporosis, scleroderma, pressure atrophy of bone or tissues as in bedsores, cholesteatoma, and abnormal wound healing. MI can additionally be applied as an adjunct to other wound healing promoters, e.g., to modulate the turnover of collagen during the healing process.

MI also plays a role in the hematopoietic processes based on its erythroid potentiating activity (i.e., stimulation of differentiation of early erythroid progenitors), and thus MI is useful in the treatment of various anemias.

In addition MI has application in the treatment of immunological disorders such as autoimmune diseases (e.g., rheumatoid arthritis, multiple sclerosis) based upon its ability to suppress B-cell differentiation as determined by the method of Pisko et al. [J. Immunol. 136, 2141–2150 (1986)].

Based on its ability to inhibit connective tissue degradation and to inhibit proliferation of capillary endothelial cells, MI and/or TIMP has application in cases where inhibition of angiogenesis is useful, e.g., in preventing or retarding tumor development.

The subject invention also relates to antibodies specifically binding metalloproteinase inhibitor. Example 6 below describes the production of polyclonal antibodies. A further embodiment of the invention is monoclonal antibodies specifically binding MI. In contrast to conventional antibody (polyclonal) preparations which typically include different antibodies directed against different determinants (epitopes), each monoclonal antibody is directed against a single determinant on the antigen. Monoclonal antibodies are useful to improve the selectivity and specificity of diagnostic and analytical assay methods using antigen-antibody binding. A second advantage of monoclonal antibodies is that they are synthesized by the hybridoma culture, uncontaminated by other immunoglobulins. Monoclonal antibodies may be prepared from supernatants of cultured hybridoma cells or from ascites induced by intra-peritoneal inoculation of hybridoma cells into mice. The hybridoma technique described originally by Köhler and Milstein [Eur. J. Immunol. 6, 511–519 (1976)] has been widely applied to produce hybrid cell lines that secrete high levels of monoclonal antibodies against many specific antigens.

The following examples are offered to more fully illustrate the invention, but are not to be construed as limiting the scope thereof.

EXAMPLE 1

Purification/Characterization of Metalloproteinase Inhibitors from Bovine Aortic Endothelial Cell Conditioned Medium.

1. Conditioned Medium.

Bovine aortic endothelial cells (cell line $NCACl_2$; De Clerck et al., Cancer Research, supra) were cultured in Eagle's Minimum Essential Medium (MEM) containing fetal bovine serum (2%, v/v) supplemented with MITO+ serum extender (2%, v/v; Collaborative Research, Inc., Bedford, Mass.), penicillin (100 U/ml) and streptomycin (100 µg/ml). Cells between passage 10 and 20 were grown in 800 $cm^2$ roller bottles (Costar). For conditioning, cultures at 80–90% confluence were washed 3 times with serum-free medium over 4 to 5 h and then incubated in the presence of fresh serum-free medium for 48 h. The medium was collected, centrifuged at 5,000×g for 10 min at 4° C. and kept at 4° C. after addition of sodium azide (0.02%, w/v). After the conditioning, cells were trypsinized, diluted 1:4 with medium, and grown to 80% confluence for reconditioning.

2. Inhibition Assays.

Purification work was monitored by inhibitory activity measured using a radiolabeled collagen film assay as described by Johnson-Wint [Anal. Biochem. 104, 175–181 (1980)]. The substrate used was $^{14}C$-acetylated rat skin collagen (about 300 cpm/µg) which was plated in a 96-well microtiter plate at 20 µl per well (about 6,000 cpm/well). The collagenase source was serum-free conditioned medium from 12-O-tetradecanoylphorbol-13-acetate (TPA)-treated rabbit synovial fibroblasts with a collagenase activity of approximately 8 units/ml (1 unit is the amount of enzyme that degrades 1 µg of collagen per min at 37° C.). Proenzyme was activated with trypsin (10 µg/ml) for 30 min at 22° C. and this was followed by inactivation of trypsin with a five-fold weight excess of soybean trypsin inhibitor. Various amounts of samples to be tested were incubated with the activated enzyme (40 mU) in a final volume of 200 µl also including Tris-HCl (50 mM) and $CaCl_2$ (10 mM) with pH of 7.5. These mixtures were then added to individual wells containing [$^{14}C$]collagen. After incubation at 37° C. for 3 h, supernatants were removed and counted in a beta scintillation counter. Percent inhibition was calculated by comparing the radioactivity released for cases containing samples tested with the radioactivity released for the case containing collagenase alone. Background cpm values (buffer alone cases) were substracted from all cpm values. In the absence of inhibitor, 60 to 70% of the total radiolabeled substrate was degraded. One unit of inhibitor is defined as the amount that inhibits two units of collagenase by 50%, as determined from dose-inhibition curves.

For antigelatinase activity assays, $^{14}C$-labeled collagen was heat-denatured at 60° C. for 20 min and assay was performed in test tubes [Murphy et al., Biochem. J. 192, 517–525 (1980)]. Anti type IV collagenase activity was determined as described (De Clerck et al., Cancer Res., supra; and De Clerck, Arch. Biochem. Biophys., supra) using [$^{14}C$]proline-labeled type IV collagen extracted from the mouse Englebreth-Holm-Swarm tumor.

3. Purification.

All purification work was done at 4° C. unless otherwise indicated.

a. Concentrating.

Twenty liters of medium was concentrated using a Millipore Pellicon tangential flow ultrafiltration apparatus with a 10,000 molecular weight cutoff polysulfone membrane cassette (5 ft² total membrane area), to a volume of 450 ml. The sample was then further concentrated, to 64 ml, using an Amicon TCF 10 tangential flow ultrafiltration unit with an Amicon YM10 membrane. The non-ionic detergent Brij-35 was then added from a 10% (w/v) stock, to give a final concentration of 0.05% (w/v), and the sample was dialyzed against TNC/Brij-35 buffer [50 mM Tris-HCl, 200 mM NaCl, 0.05% (w/v) Brij-35, 10 mM $CaCl_2$, pH 7.5].

b. Gel Filtration.

The dialyzed sample (60 ml) was divided into three 20 ml portions, each of which was applied to a Sephadex G-100 gel filtration column (5×91 cm) equilibrated with TNC/Brij-35 buffer at 4° C. Flow rate was 60 ml/h and fractions of 13 ml were collected. For each column run, a chromatographic profile (absorbance at 280 nm and metalloproteinase inhibitor activity) essentially like that described in De Clerck et al., Cancer Research, supra, was obtained, with two peaks of inhibitor activity corresponding to apparent molecular weights of 70,000–75,000 and 30,000–35,000. The active fractions from each of the gel filtration column runs were pooled to yield peak I material (higher molecular weight) and peak II material (lower molecular weight).

c. Peak I Purification.

1. Anion Exchange.

The peak I material from gel filtration (312 ml; 3b above) was dialyzed against 20 mM Tris-HCl, 1 mM $CaCl_2$, 0.05% (w/v) Brij-35, pH 7.5 and applied in two separate chromatographic runs to a Mono Q anion exchange column (Pharmacia; 1 ml) equilibrated in the same buffer. A gradient from 0 to 0.5 M NaCl in the same buffer (total gradient volume of 60 ml) was then applied for elution of bound material. Chromatography was done at room temperature. Flow rate was 1 ml/min and fraction size 1 ml. FIG. 3 represents the elution profiles obtained. Activity represents collagenase inhibition measured as described in section 2 above, using aliquots (15 $\mu$l) from the indicated fractions. Fractions collected during sample application are not shown; no inhibitor activity was present in these fractions.

2. Chromatofocusing.

Figure 4:
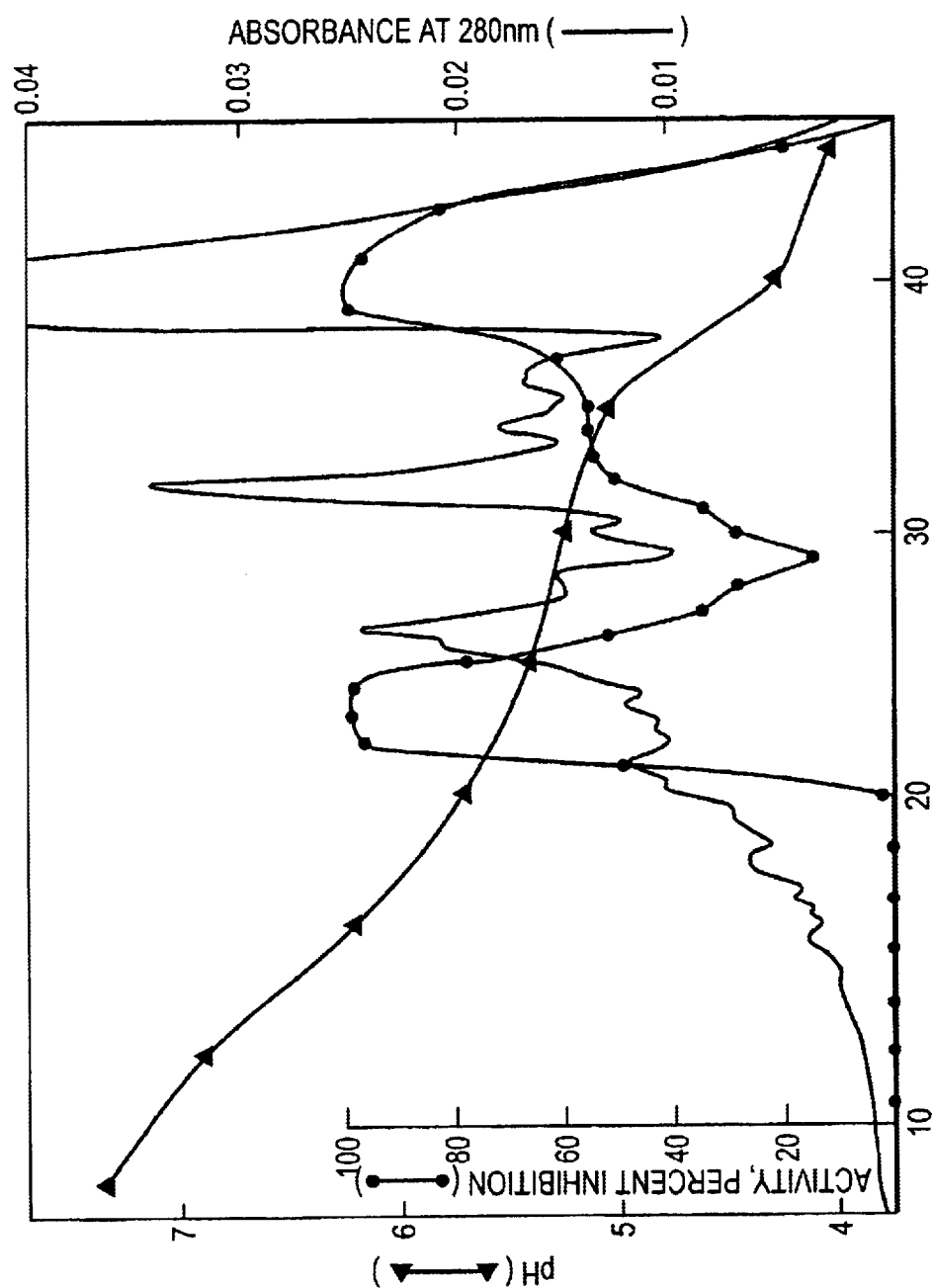
FIG. 4 shows chromatofocusing used in purification of bovine peak I-derived metalloproteinase inhibitor (MI).

The fractions from the Mono Q column runs that contained inhibitor activity were combined and the pool (12 ml) was dialyzed against 25 mM bis Tris-HCl, 1 mM $CaCl_2$, 0.05% (w/v) Brij-35, pH 7.4 and applied to a Mono P chromatofocusing column (Pharmacia; 4 ml) equilibrated in the same buffer, at room temperature. No inhibitor activity was present in fractions collected during sample application. Elution of bound material was accomplished with a pH gradient generated by applying a solution of polybuffer 74 (Pharmacia) diluted ten-fold and adjusted to pH 4 with HCl. Fractions of 1 ml were collected at a flow rate of 0.5 ml/min, immediately brought to 50 mM in Tris-HCl by addition of 50 $\mu$l of 1 M Tris-HCl, pH 7.5, and further titrated to pH 7.5 by addition of 2 M Tris base. The elution profile is shown in FIG. 4. Aliquots (5 $\mu$l) from the indicated fractions were measured for inhibitor activity as described in section 2 above. There is a peak of inhibitor activity eluting at about pH 5.5 (fractions 21–27), plus activity eluting later (fractions 30–45). These latter fractions were pooled, dialyzed against the Mono P starting buffer, and rechromatographed on the Mono P column as for the original sample. Recovered activity was redistributed between an earlier-eluting peak (about pH 5.5) and later-eluting region, with the early peak representing about one-third of the recovered activity. The later-eluting material from this second Mono P run was chromatographed again, with similar redistribution of the activity. The early-eluting fractions (pH 5.5 peak) from all three Mono P column runs were combined.

3. Gel Filtration.

The combined pool from the Mono P column runs (15 ml) was concentrated to 3 ml using Amicon Centricon 10 units centrifuged at 5000×g in a fixed-angle rotor. The concentrated sample was then applied to a Sephadex G-100 gel filtration column (1.5×94 cm) equilibrated with 50 mM Tris-HCl, 200 mM NaCl, 10 mM $CaCl_2$, pH 7.5. Fractions of 2.1 ml were collected, at a flow rate of 5 ml/h. A single peak of inhibitor activity was recovered, eluting with an apparent molecular weight of 24,000 relative to molecular weight markers used for column calibration (myoglobin, $M_r$ Of 17,000; ovalbumin, $M_r$ of 44,000; gamma-globulin, $M_r$ of 158,000), and having a specific activity of about 1,550 U/mg.

In the purification of peak I-derived inhibitor, it should be noted that the second Sephadex G-100 gel filtration step was useful because the material at this stage behaved with an apparent molecular weight of 24,000 rather than the 70,000–75,000 true for peak I activity on the initial Sephadex G-100 column.

A summary of the purification for peak I-derived material is shown in Table 1.

Table I.

(See following page.) Purification of two metalloproteinase inhibitors from bovine aortic endothelial cells. After steps 1 and 2, the inhibitors were separately purified as indicated. Recovery and degree of purification were calculated separately for the two inhibitor preparations, assigning values of 100% and 1, respectively, for each of the step 2 Sephadex G-100 peaks.

TABLE 1

| Step | Volume (ml) | Total protein (mg)[a] | Total activity (units) | Specific activity (units/mg) | Recovery (percent) | Purification (fold) |
|---|---|---|---|---|---|---|
| 1. Conditioned medium concentrated by ultrafiltration | 64 | 127 | 907 | 7.2 | — | — |
| 2. Sephadex G-100 | | | | | | |
| | | Peak I-derived Inhibitor | | | | |
| 2.1 Peak I | 312 | 22.5 | 202 | 9 | (100) | (1) |
| 2.1.1 Mono Q | 17 | 2.2 | 121 | 55 | 59 | 6 |

TABLE 1-continued

| Step | Volume (ml) | Total protein (mg)[a] | Total activity (units) | Specific activity (units/mg) | Recovery (percent) | Purification (fold) |
|---|---|---|---|---|---|---|
| 2.1.2 Mono P | 3 | ~0.1[b] | 62 | ~620 | 30 | 86 |
| 2.1.3 Sephadex G-100 | 12 | ~0.02[b] | 31 | ~1,550 | 15 | 172 |
| Peak II-derived Inhibitor | | | | | | |
| 2.2 Peak II | 470 | 16.4 | 695 | 42 | (100) | (1) |
| 2.2.1 Heparin-Sepharose | 7.5 | 2.6 | 330 | 126 | 47 | 3 |
| 2.2.2 Mono Q | 12 | 0.16 | 292 | 1,780 | 42 | 42 | d. Peak II purification.

Footnotes:
[a]Determined by the method of Bradford [Anal. Bioch. 72, 248–254 (1976)] using BSA as standard, except where indicated otherwise.
[b]Estimate, based on intensity of silver-stained bands after SDS-PAGE.

Peak II Purification.
1. Heparin-Sepharose.

The peak II material from gel filtration (465 ml; 3b above) was dialyzed against 25 mM sodium cacodylate-HCl, 10 mM $CaCl_2$, 0.05% (w/v) Brij-35, pH 7.5 and chromatographed on a heparin-Sepharose column equilibrated with this buffer. After column washing, elution of bound material was achieved with a linear gradient to 1 M NaCl in the same buffer [see De Clerck, Arch. Biochem. Biophys. 265, 28–37 (1988)].

2. Anion Exchange.

The active fractions from heparin-Sepharose were combined (total volume 7.5 ml) and dialyzed against 20 mM Tris-HCl, 1 mM $CaCl_2$, pH 7.5. The material was then divided and applied in two separate chromatographic runs to a Mono Q column as described above (c.1). Eighty to 90% of the recovered activity was present in fractions collected during sample application (unbound), and represented highly-purified peak II-derived inhibitor material with a specific activity of about 1,780 U/mg. The remainder of the activity eluted early (about 0.065 M NaCl) in the salt gradient.

A summary of the purification for peak II-derived material is shown in Table 1.

4. Characterization of Peak I-derived and Peak II-derived Inhibitors.

a. SDS-PAGE was carried out by the method of Laemmli [Nature 227, 680–685 (1970)]. Stacking gels contained 4% (w/v) acrylamide and separating gels contained 12.5% (w/v) acrylamide. Samples were prepared under reducing or non-reducing conditions, that is, with or without 2-mercaptoethanol present in the treatment buffer. After electrophoresis, gels were subjected to silver-staining [Morrissey, Anal. Biochem. 117, 307–310 (1981)] or immunoblotting [Burnette, Anal. Biochem. 112, 195–203 (1981)].

1. Peak I-derived Inhibitor.

The active fractions from the Sephadex G-100 column (c.3 above) all contained a fairly sharp major band evident upon SDS-PAGE with silver-staining, migrating with apparent molecular weight of 24,000–28,000 (reduced) and 19,000–22,000 (unreduced). This band was also evident in active fractions from the step that preceded (c.2 above; Mono P). Such co-elution of activity and material banding at this position is consistent with the conclusion that the band represents active protein. This band can be seen in FIG. 5A, lanes 1 and 2. For these gels, 100 µl of the final gel filtration pool (c.3 above; Table 1, step 2.1.3) was loaded; lane 1, reduced and lane 2, unreduced. Note that the difference in migration for the reduced and unreduced material probably reflects the presence of intrachain disulfide bonds in the unreduced case.

Figure 5A:
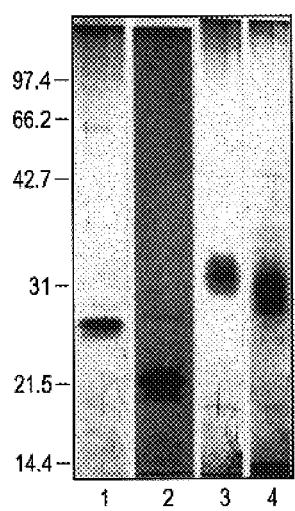
FIGS. 5A & 5B show SDS-PAGE of bovine peak I-derived metalloproteinase inhibitor (MI) and peak II-derived metalloproteinase inhibitor. A is SDS-PAGE with silver-staining, B is SDS-gelatin PAGE, and C is SDS-PAGE with immunoblotting.
Figure 5B:
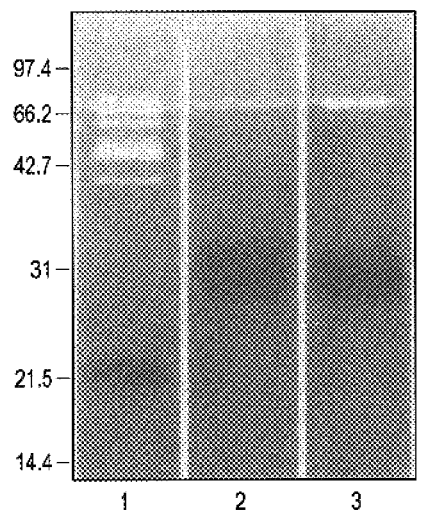
Figure 5C:
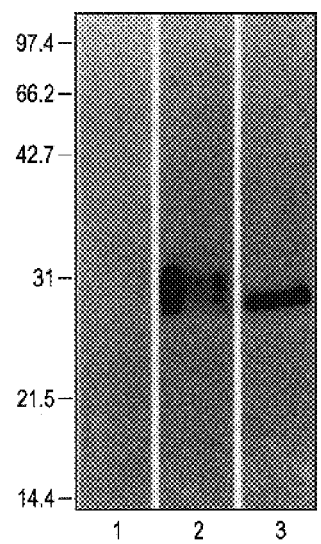

FIG. 5C, lane 1 shows the result of SDS-PAGE with immunoblotting for a similar sample (250 mU; unreduced). The primary antibody in the immunoblotting was a rabbit polyclonal antibody against TIMP from bovine vascular smooth muscle cells (De Clerck, Arch. Biochem. Biophys., supra) used at 1:500 dilution. (The secondary antibody used for detection was a goat anti-rabbit antibody conjugated with horseradish peroxidase.) No bands were visualized with the use of this primary antibody. Note that FIG. 5C, lane 3 shows that TIMP from bovine vascular smooth muscle cells (160 mU; unreduced) is visualized with the use of this antibody.

2. Peak II-derived Inhibitor.

SDS-PAGE with silver-staining is shown in FIG. 5A, lanes 3 (reduced) and 4 (unreduced) for the unbound material from Mono Q chromatography (d.2 above; Table 1, step 2.2.2; 75 µl loaded). The staining material migrates over a fairly broad region representing a molecular weight range of 30,000–34,000 (reduced) and 27,000–31,000 (unreduced).

FIG. 5C, lane 2 shows that the peak II-derived inhibitor (240 mU loaded; unreduced) is visualized by SDS-PAGE with immunoblotting using the antibody against bovine vascular smooth muscle cell TIMP.

b. SDS-gelatin PAGE.

The major bands on SDS-PAGE, as visualized by silver-staining, are also visualized, at the same molecular weight positions, with SDS-gelatin polyacrylamide gels, which identify proteins with inhibitory activity toward gelatinolytic enzymes [see Herron et al., J. Biol. Chem. 261, 2814–2818 (1986); De Clerck et al., Cancer Research, supra; and De Clerck, Arch. Biochem. Biophys., supra]. In this method, samples are subjected to SDS-PAGE, using gels with 10% (w/v) acrylamide and 0.1% (w/v) gelatin. The gels are then incubated in 2.5% (w/v) Triton X-100 for 1 h with two changes, to remove SDS, incubated for 3 h at 37° C. in 10 ml of p-aminophenylmercuric acetate (APMA)-activated conditioned medium from rabbit synovial fibroblasts to degrade gelatin, and then incubated overnight in 50 mM Tris-HCl, 10 mM $CaCl_2$, pH 7.5. The gels are then stained with Coomassie blue and destained with methanol:acetic acid:water (50:10:40). Bands having collagenase/gelatinase inhibitory activity show up as dark (blue) zones representing undegraded gelatin. The results of applying this method are shown in FIG. 5B for the following samples (all unreduced): lane 1, partially-purified peak I-derived inhibitor (50 mU loaded); lane 2, peak II-derived inhibitor (240 mU loaded); lane 3, bovine vascular smooth muscle cell TIMP (160 mU loaded). As mentioned, dark zones represent proteins with inhibitory activity toward gelatinolytic enzymes. The results further support the conclusion that the major silver-stained bands in the purified preparations represent the proteins with metalloproteinase inhibitor activity.

c. SDS-gelatin PAGE with Proteinase Samples.

Figure 6:
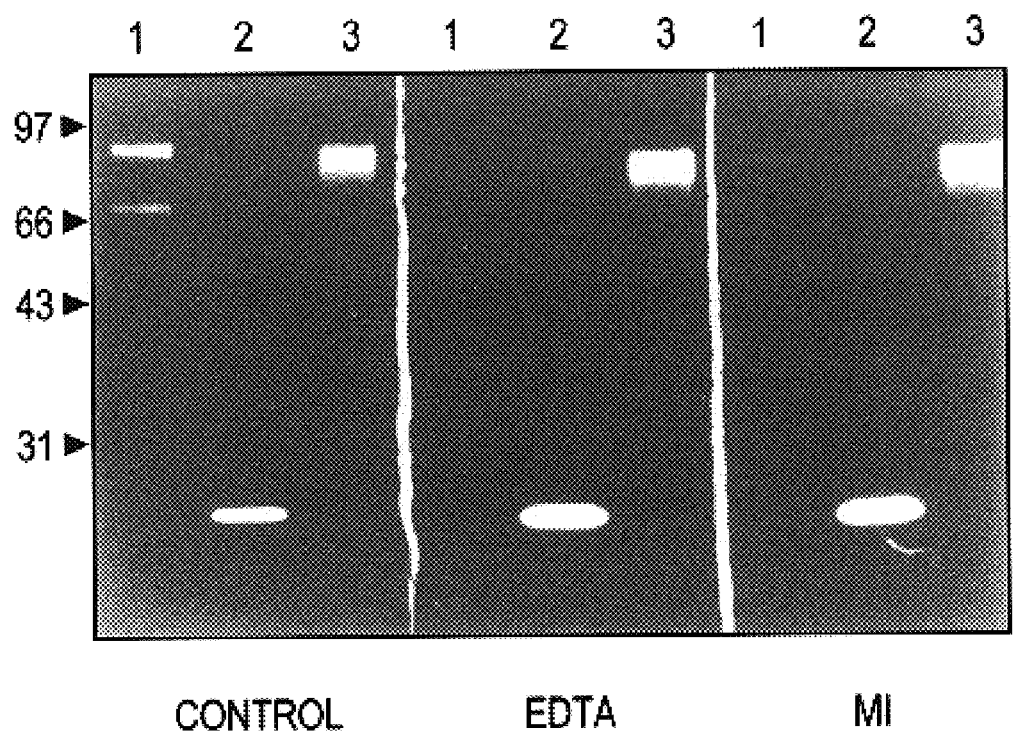
FIG. 6 shows effect of EDTA and of bovine peak I-derived metalloproteinase inhibitor (MI) on gelatinolytic proteinases run on SDS-gelatin PAGE.

To further test the preparations for inhibitory activity toward gelatinases, trypsin, or plasmin, samples containing the proteinases were electrophoresed on SDS-gelatin gels (supra). The gels were then incubated in 2.5% (w/v) Triton X-100 for 1 h with two changes, to remove SDS, and then incubated overnight in 50 mM Tris-HCl, 10 mM $CaCl_2$, pH 7.5 with or without the preparation being tested for inhibitory activity, stained with Coomassie blue, and destained (as in SDS-gelatin PAGE methods referred to, supra). See FIG. 6. For the lanes 1, 2 and 3 in this figure, electrophoresed samples were (respectively) APMA-activated conditioned medium from TPA-treated rabbit synovial fibroblasts (1.2 mU of collagenase activity; see section 2 of this Example), bovine trypsin (0.01 μg), and human plasmin (0.03 μg). In the case marked "MI", the overnight incubation of the gel included peak I-derived inhibitor (0.2 U/ml). Clear zones are indicative of gelatinolytic activity of the electrophoresed proteinase samples. Note by comparison to the "control" cases that "MI" inhibits the collagenases (clear zones at $M_r$ about 68,000 and 92,000 in "control" lane 1), but not trypsin or plasmin (which are not metalloproteinases). Similarly, it can be seen in FIG. 6 that the chelator "EDTA" (included at 20 mM) inhibited collagenases but not trypsin or plasmin, as expected.

d. Inhibition of Various Collagenases and Metalloproteinases.

Table 2 shows that peak I-derived material inhibited type I collagenase, gelatinase(s), and type IV collagenase, but did not inhibit bacterial collagenase.

TABLE 2

Effect of peak I-derived inhibitor on various collagenases

| Enzyme | Substrate | Peak I-derived inhibitor amount (mU) | Inhibition (%) |
|---|---|---|---|
| Type I collagenase[a] | $^{14}$C-labeled type I collagen[d] | 50 | 100 |
| Gelatinase[a] | $^{14}$C-labeled type I collagen, heat denatured[e] | 50 | 90 |
| Bacterial collagenase[b] | $^{14}$C-labeled type I collagen[d] | 200 | 0 |
| Type IV collagenase[c] | $^{14}$C-labeled type IV collagen[d] | 200 | 66 |

Figure 7:
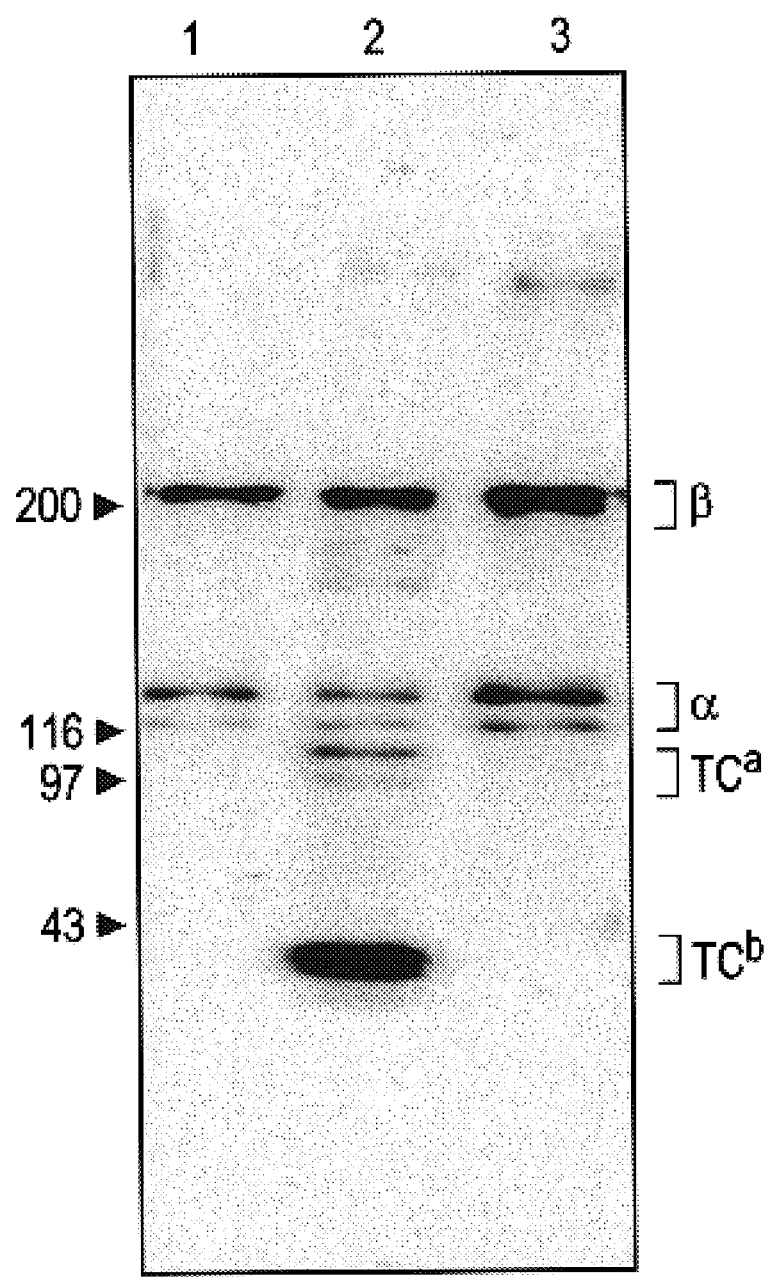
FIG. 7 shows autoradiography illustrating effect of bovine peak I-derived metalloproteinase inhibitor (MI) on specific collagen cleavage.

[a]Trypsin-activated conditioned medium from TPA-treated rabbit synovial fibroblasts (40 mU; see Example 1, section 2).
[b]Form III from *Clostridium histolyticum* (34 mU) (Advance Biofacture Corp., Lynbrook, NJ).
[c]Trypsin-activated conditioned medium from mouse reticulum cell sarcoma cell line (50 μl of 104-fold concentrated medium; see De Clerck, Arch. Biochem. Biophys., supra).
[d]See Example 1, section 2.
[e]Heat-denatured at 60° C. for 20 min.

e. SDS-PAGE of $^{14}$C-labeled collagen degradation products generated by type I (classical) collagenase in the absence and presence of the peak I-derived inhibitor is shown in FIG. 7. [14]C-Labeled type I collagen (30,000 cpm) was incubated under the conditions described for inhibition assays in Example 1, section 2, with various additions, at 22° C. for 16 h. EDTA (20 mM) was then added to block metalloproteinase reactions, and samples were subjected to SDS-PAGE using a gradient gel (5–15% acrylamide). The gel was incubated in Autofluor (National Diagnostics, Manville, N.J.), dried and subjected to autoradiography. For FIG. 7: lane 1, no additions; lane 2, APMA-activated conditioned medium from TPA-treated rabbit synovial fibroblasts (5 μl of medium containing 40 mU of collagenase activity prepared as described in Example 1, section 2); lane 3, as lane 2, plus partially-purified peak I-derived inhibitor (50 mU). In the Figure, $TC^a$ and $TC^b$ represent the ¾-length and ¼-length fragments derived from single specific cleavage of the full-length α collagen polypeptide chains [Gross et al., Biochemistry 54, 1197–1204 (1965)], and β represents dimeric β chains. The results indicate that the inhibitory activity of peak I-derived inhibitor can be directed against the single peptide bond cleavage located one quarter of the distance from the COOH-terminus and characteristic of mammalian collagenase.

f. The purified peak I-derived and peak II-derived materials have been characterized with regard to susceptibilities to heat, acid, reduction-alkylation, and trypsin treatment. The results are shown in Table 3.

Table 3

Stability of peak I-derived and peak II-derived inhibitors. Inhibitor samples (2 U/ml) were treated as indicated prior to being tested for residual anticollagenase activity determined from dose-inhibition curves.

TABLE 3

Stability of peak I-derived and peak II-derived inhibitors. Inhibitor samples (2 U/ml) were treated as indicated prior to being tested for residual anticollagenase activity determined from dose-inhibition curves.

| | | Loss of inhibitory activity (%) | |
|---|---|---|---|
| Treatment | Conditions | Peak I-derived inhibitor | Peak II-derived inhibitor |
| (A) Heat[a] | 37° C. | 0 | 11 |
| | 50° C. | 0 | 11 |
| | 80° C. | 9 | 30 |
| | 100° C. | 59 | 44 |
| (B) Trypsin[b] | | | |
| | 1:1 | 10 | 0 |
| | 10:1 | 28 | 21 |
| | 50:1 | 100 | 100 |
| (C) Acid | pH 4.5, 22° C., 1 h | 0 | 0 |
| (D) Reduction-alkylation[c] | | 100 | 100 |

[a]Inhibitor samples were incubated at indicated temperatures for 1 h. Loss of inhibitory activity was calculated in comparison with an untreated sample.
[b]Samples were incubated at indicated trypsin: inhibitor ratios (w:w) for 1 h at 37° C. The reaction was then blocked with five-fold weight excess of soybean trypsin inhibitor. Loss of activity was determined in comparison with a sample incubated at 37° C. for 1 h in the presence of a trypsin-soybean trypsin inhibitor mixture.
[c]Samples were reduced by the addition of 2-mercaptoethanol (20 mM) for 16 h at 4° C. and alkylated with iodoacetamide (20 mM) at 30° C. for 1 h. Loss of activity was determined by comparison with samples incubated at the same temperatures. 2-Mercaptoethanol and iodoacetamide did not affect collagenase activity.

EXAMPLE 2

Amino-Terminal Amino Acid Sequence Analysis of Peak I-derived Inhibitor and Peak II-derived Inhibitor; Amino Acid Composition Analysis of Peak I-derived Inhibitor.

Peak I-derived inhibitor (4.8 ml; Table 1, step 2.1.3) was concentrated and introduced into 50 mM ammonium bicarbonate, pH 7.8 using an Amicon Centricon 10 ultrafiltration unit. The sample was spotted onto a glass fiber disc on a sequencer cartridge, which had been pre-cycled with polybrene. The glass fiber disc containing sample was dried under a stream of N₂. Amino-terminal amino acid sequence analysis was performed according to published methods [Hewick et al., J. Biol. Chem. 256, 7990–7997 (1981)] with Applied Biosystems Model 477 protein sequencer using a standard program provided by Applied Biosystems (Foster City, Calif.). The released phenylthiohydantoin (PTH)-amino acids were analyzed by a Model 120 on-line PTH-amino acid analyzer using a Brownlee reverse phase C-18 column. The chromatograms obtained were analyzed by a Model 900 data module. An initial yield of approximately 158 pmol was obtained with an average repetitive yield of 94%. Amino acid assignments at 42 positions were made. In a repeat sequencing run, the assignments were completely identical to those of the first sequencing run except that three more amino acids (positions 43–45) were assigned. Table 4 shows the assigned amino-terminal amino acid sequence.

Table 4
Amino-terminal Sequence of Bovine Peak I-derived Inhibitor

The initial yield was approximately 280 pmol and the average repetitive yield was 92%. Residues 1, 3 and 13 were assigned as cysteines for the reasons described above. Residue 30 was also not recovered and was assigned as asparagine since the subsequent sequence

```
(Asn-Glu-Thr . . .)
 30   31  32
``` would be consistent with an Asn-linked glycosylation site. The assignments at positions 43 and 48 (in brackets) were made with less than full confidence.

Based on these various analyses (Examples 1 and 2), the peak II-derived material is almost certainly bovine TIMP. Human TIMP is very well characterized and has been cloned (Docherty et al., Nature, supra; Carmichael et al., Proc. Natl. Acad. Sci. USA, supra). Comparing the amino-terminal sequences of human TIMP and the peak II-derived material, the homology over the first 29 residues is 93% and the homology over the first 49 residues is 80% (see Table 6). In addition the isolated bovine peak II-derived material shares many of the biochemical properties of TIMP, i.e., behavior

TABLE 4

Amino-terminal sequence of bovine
peak I-derived inhibitor

```
 1    2    3    4   5   6   7   8   9  10  11  12   13     (SEQ ID NO: 10)
(Cys)-Ser-(Cys)-Ser-Pro-Val-His-Pro-Gln-Gln-Ala-Phe-(Cys)-

14  15  16  17  18  19  20  21  22  23  24  25  26
Asn-Ala-Asp-Ile-Val-Ile-Arg-Ala-Lys-Ala-Val-Asn-Lys- 27  28  29  30  31  32  33  34  35  36  37  38  39
Lys-Glu-Val-Asp-Ser-Gly-Asn-Asp-Ile-Tyr-Gly-Asn-Pro- 40  41  42  43  44  45
Ile-Lys-Arg-Ile-Gln-Tyr-----
```

Residues 1, 3 and 13 were assigned as cysteines since no other assignments could be made for these cycles and cysteine is undetectable by the sequencing methods used.

In order to compare sequence, a preparation of. purified peak II-derived inhibitor (2.25 ml; Table 1, step 2.2.2; prepared as described for peak I-derived inhibitor) was also subjected to amino-terminal sequence analysis. The sequence shown in Table 5 was obtained.

Table 5
Amino-terminal Sequence of Bovine Peak II-derived Inhibitor in various purification steps, mobility on SDS-PAGE, and recognition by antibody to bovine smooth muscle TIMP in SDS-PAGE with immunoblotting (Example 1).

The peak I-derived material (MI) is clearly distinct from TIMP (Table 6) in amino acid sequence, but does have homology to TIMP. Homology over the first 29 residues is 65%, and homology over the first 45 residues is 47%. The molecules have different chromatographic behaviors, different mobilities on SDS-PAGE, and antibody to bovine smooth muscle TIMP does not visualize the peak I-derived material in immunoblots after SDS-PAGE (Example 1). This novel peak I-derived inhibitor is designated metalloproteinase inhibitor (MI).

TABLE 5

Amino-terminal sequence of bovine
peak II-derived inhibitor

```
 1    2    3    4   5   6   7   8   9  10  11  12   13     (SEQ ID NO: 11)
(Cys)-Thr-(Cys)-Val-Pro-Pro-His-Pro-Gln-Thr-Ala-Phe-(Cys)-

14  15  16  17  18  19  20  21  22  23  24  25  26
Asn-Ser-Asp-Val-Val-Ile-Arg-Ala-Lys-Phe-Val-Gly-Thr- 27  28  29  30   31  32  33  34  35  36  37  38  39
Ala-Glu-Val-(Asn)-Glu-Thr-Ala-Leu-Leu-Tyr-Arg-Tyr-Leu- 40  41  42   43  44  45  46  47  48   49
Ile-Lys-Met-[Leu]-Lys-Met-Pro-Ser-[Gly]-Phe---
```

Over the first 45 residues, the peak I-derived and peak II-derived bovine inhibitors have 51% homology to each other.

TABLE 6

Comparison of the amino-terminal sequence of
(1) human TIMP[a], (2) bovine peak II-derived
inhibitor (TIMP)[b] and (3) bovine peak
I-derived inhibitor (MI)[c]

```
                1                   10                        20
1 HUMAN       C T C V P P H P Q T A F C N S D L V I R
  TIMP
2 BOVINE      C T C V P P H P Q T A F C N S D V V I R
  TIMP
3 BOVINE MI   C S C S P V H P Q Q A F C N A D I V I R 21                  30                        40
1 HUMAN       A K F V G T P E V N Q T T L Y Q R Y E I
  TIMP
2 BOVINE      A K F V G T A E V N E T A L L Y R Y L I
  TIMP
3 BOVINE MI   A K A V N K K E V D S G N D I Y G N P I 41              49
1 HUMAN       K M   T   K M Y K   G   F (SEQ ID NO: 12)
  TIMP
2 BOVINE      K M (L) K M P S (G) F (SEQ ID NO: 13)
  TIMP
3 BOVINE MI   K R   I   Q Y (SEQ ID NO: 14)
```

[a]From Docherty et al., Nature, supra; and Carmichael et al., Proc. Natl. Acad. Sci. USA, supra.
[b,c]From sequence analyses described in Example 2.

The amino acid composition of the bovine peak I-derived inhibitor (MI) is shown in Table 7. A sample of the peak I-derived inhibitor (1.2 ml; Table 1, stap 2.1.3) was concentrated and introduced into 50 mM ammonium bicarbonate, pH 7.8 using an Amicon Centricon 10 ultrafiltration unit. The sample was then dried and subject to amino acid composition analysis by the method described by Lu et al. (J. Chromatog. 368, 215–231 (1986)). This involved chromatograhic analysis of phenyltiocarbamyl-amino acids generated after acid hydrolysis (24 h) of the samples. Data from three seperate chromatograhic analysis were used to estimate average residuse per molecule values. For each of these analyses an amount of material derived from one-tenth of the starting sample was used. The value for total amino acid (178) used in calculataing residuse per molecule was taken from the gene-encoded sequence for the mature bovine MI (Example 3 FIG. 1 (SEQ ID NO: 7).

TABLE 7

Amino acid composition analysis of bovine peak I-derived inhibitor (MI)

| Amino acid | Residues per molecule | | |
|---|---|---|---|
| | Average value | Integral value | "Actual" value[c] |
| Lys | 15.5 | 16 | 17 |
| His | 3.6 | 4 | 4 |
| Arg + Thr[a] | 15.9 | 16 | 6 + 6 = 12 |
| Asx[1] | 22.9 | 23 | 22 |
| Ser | 10.9 | 11 | 10 |
| Glx[1] | 19.4 | 19 | 19 |
| Pro | 8.1 | 8 | 12 |
| Gly | 14.2 | 14 | 13 |
| Ala | 15 | 15 | 16 |
| Val | 9 | 9 | 8 |
| ½-Cys | nd[b] | | (12) |
| Met | 3.1 | 3 | 5 |
| Ile | 14.6 | 15 | 19 |
| Leu | 10.8 | 11 | 7 |
| Tyr | 7.1 | 7 | 7 |
| Phe | 7.7 | 8 | 7 |
| Trp | nd[b] | | (4) |
| | 178 | 179 | 178 + 12 + 4 = 194 |

[a]Arg and Thr were not separable by the method used.
[b]Not determined.
[c]Values from gene-encoded sequence of mature bovine MI polypeptide; see Example 3, FIG. 1.

EXAMPLE 3

Cloning of the Bovine and Human Metalloproteinase Inhibitor Genes.

The amino-terminal amino acid sequence for the bovine metalloproteinase inhibitor was determined as described above and 3 probes were designed and manufactured on DNA synthesizers (Applied Biosystems models 380A and 380B) for hybridization to the sense strand of DNA (or to the mRNA). The first probe was designed as a long nondegenerate probe by the method of Lathe [J. Mol. Biol. 183, 1–12 (1985)] to recognize the region corresponding to amino acids 4 to 19 and is as follows:

5' GAT CAC AAT GTC AGC ATT GCA GAA GGC CTG CTG GGG ATG CAC AGG 3' (SEQ ID NO: 15)

The second and third probes were designed as degenerate probes incorporating inosine bases at positions of 4-fold degeneracy. The second probe recognizes the region corresponding to amino acids 21 to 30 and is as follows:

```
                                              (SEQ ID NO: 16)
          (T)    (T)    (T)                          (T)
5' GTC IAC (C)TC (C)TT (C)TT GTT IAC IGC (C)TT

IGC 3'
```

The parentheses indicate the incorporation of two bases, leading to multiple oligonucleotides in the probe preparation. The third probe recognizes the region corresponding to amino acids 32 to 41 and is as follows:

```
                                              (SEQ ID NO: 17)
          (A)    (A)          (A)    (A)
5' CTT IAT IGG (G)TT ICC (G)TA IAT (G)TC (G)TT

ICC 3'
```

A λgtll CDNA library, made with mRNA isolated from bovine aorta endothelial cells, was purchased from CLONTECH Laboratories, Inc. (Palo Alto, Calif.). Approximately 10[6] phage were plated onto eight 23×23 cm square plates with the host bacterial strain, Y1090. Two lifts from each plate were made onto GeneScreen Plus (Dupont) hybridiza tion transfer membranes. One set of membranes was hybridized with $^{32}$P-phosphorylated probe 2 and the other set of membranes was hybridized with $^{32}$P-phosphorylated probe 3. Hybridizations were done overnight in 6×SSC, 5×Denhardts, 0.5% (w/v) SDS, 50 µg/ml sheared and denatured herring sperm DNA at 50–55° C. The filters were washed in 6×SSC, 0.5% (w/v) SDS at approximately 55° C. After autoradiography, three clones were identified which hybridized to both probes. These clones were rescreened until isolated plaques were obtained for each. Mini λ phage preps were made for each of the three clones using the LambdaSorb Phage Adsorbent from Promega. Restriction endonuclease digests of the three clones using several restriction enzymes indicated that all three clones were identical and were obtained due to amplification of the cDNA library by the supplier. By Southern blotting analysis, the same restriction fragments were found to hybridize not only to probes 2 and 3, but to probe 1 as well.

The restriction endonuclease analysis indicated that the rightward EcoRI site had been abolished during the cDNA cloning. Therefore, the cDNA-containing fragment from the leftward EcoRI site to an SstI site in λgtll approximately 1 kilobase (kb) from the abolished EcoRI site was cloned into pUC 19 to generate pUC BMI. Overlapping restriction fragments of both orientations were subsequently cloned from pUC BMI into M13 mp vectors to obtain the sequence of the gene using the dideoxy method of Sanger et al. [Proc. Natl. Acad. Sci. USA 74, 5463–5467 (1977)]. As shown in FIG. 1, the gene codes for a mature protein of 194 amino acids with a leader sequence of 26 amino acids. The first 45 amino acids of the mature protein exactly match the amino-terminal sequence determined for the purified protein (Example 2). In addition, the amino acid composition as determined from the gene-encoded sequence of the mature bovine MI polypeptide is in agreement with that obtained experimentally for the bovine peak I-derived inhibitor (see Example 2, Table 7), providing further evidence that the cloned gene corresponds to the purified MI polypeptide of Example 1. The molecular weight of the mature bovine MI polypeptide chain, based on the gene-encoded sequence in FIG. 1, is 21,693.

Four long oligonucleotide probes (51-mers), which exactly match the sequences of the antisense strand of the bovine metalloproteinase inhibitor coding region, were manufactured on DNA synthesizers (Applied Biosystems models 380A and 380B) in order to screen human cDNA libraries for the human MI gene sequences. The 4 sequences were as follows:

plated onto eight 23×23 cm square plates with the host bacterial strain, Y1090. Two lifts from each plate were made onto GeneScreen Plus hybridization transfer membranes. One set of membranes was hybridized with a mixture of $^{32}$P-phosphorylated probes 1 and 2, and the second set of membranes was hybridized with a mixture of $^{32}$P-phosphorylated probes 3 and 4, using the hybridization and wash conditions described above. Three clones hybridized to both sets of probes and these clones were rescreened until isolated plaques were obtained. Mini λ phage DNA preps were made as described above and restriction endonuclease digests were performed on the DNAs. The three clones were of similar but different lengths so one of the clones was subcloned from λgtll into M13 mp9 from EcoRI to EcoRI in both orientations. This EcoRI fragment was subsequently cloned from M13 mp9 into pUC 19 to generate pUC HMI. The original clones in M13 mp9 and additional overlapping restriction fragments cloned from pUC HMI into M13 mp vectors in both orientations were sequenced using the dideoxy method of Sanger (Proc. Natl. Acad. Sci. USA, supra). The sequence of the human metalloproteinase inhibitor gene is shown in FIG. 2. It, like the bovine metalloproteinase inhibitor gene, codes for a protein of 194 amino acids with a leader sequence of an additional 26 amino acids. The two genes code for different amino acids at 11 of the 194 residues corresponding to the mature protein. The molecular weight of the mature human MI polypeptide, based on the gene-encoded sequence in FIG. 2, is 21,730.

EXAMPLE 4

Expression of Recombinant Human Metalloproteinase Inhibitor in E. coli.

Figure 8:
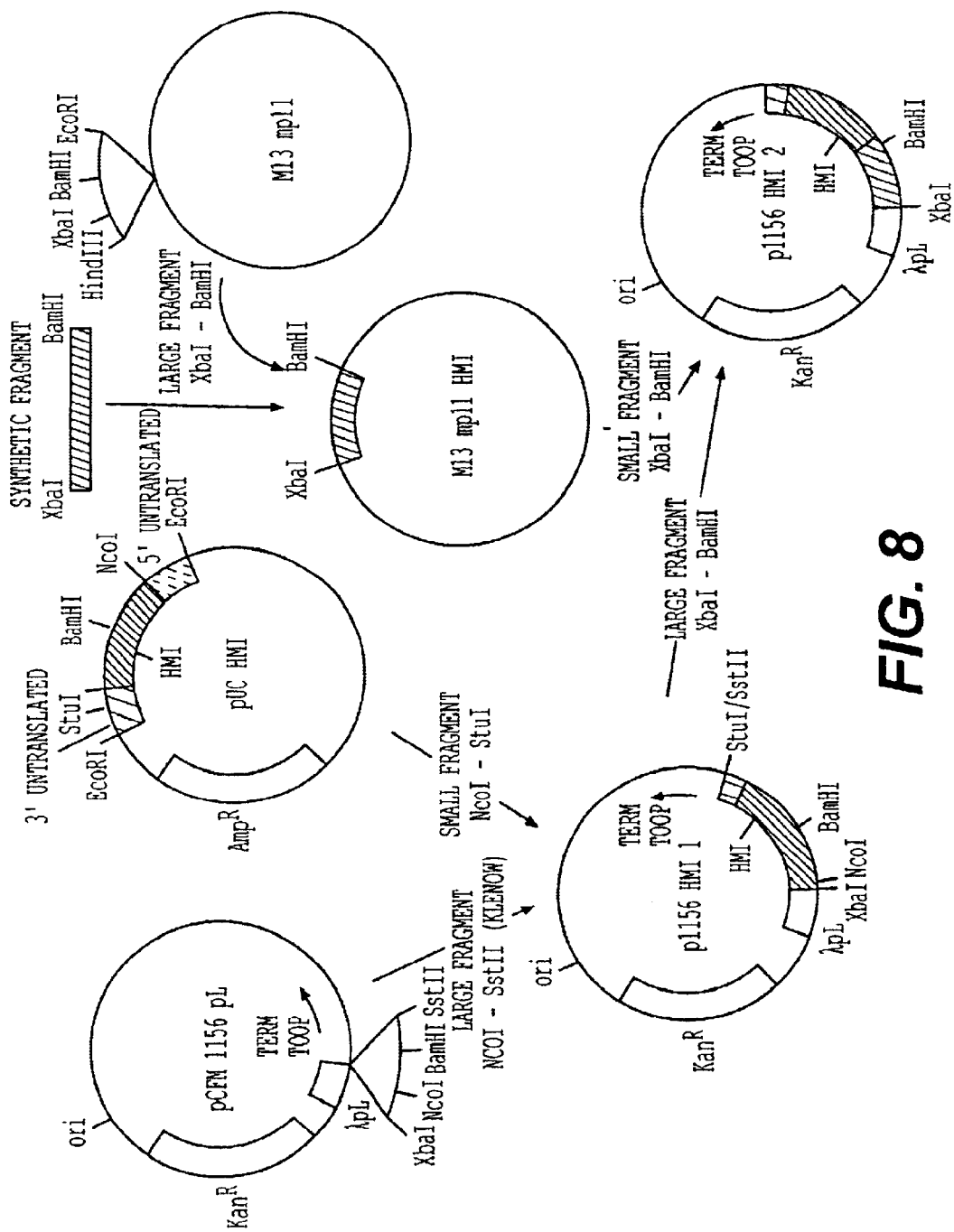
FIG. 8 shows a diagram of plasmid constructions made for expression of recombinant human metalloproteinase inhibitor in *Escherichia coli*.

The mature human metalloproteinase inhibitor protein was expressed in E. coli by utilizing an NcoI site at amino acid 1 of the leader sequence, a BamHI site at amino acid 42 of the mature protein, and a StuI site 3 nucleotides downstream from the termination codon. The fragment from NcoI to StuI was first cloned into an expression vector, pCFM 1156 pL, from NcoI to SstII (which had been blunted at the SstII site using the Klenow fragment of DNA polymerase I) to generate p1156HMI1 (FIG. 8). The plasmid PCFM 1156 pL can be derived from plasmid PCFM 836 (see U.S. Pat. No. 4,710,473 hereby incorporated by reference), by destroying the two endogenous NdeI restriction sites by end filling with T4 polymerase enzyme followed by blunt end ligation, replacing the DNA sequence between the unique AatII and ClaI restriction sites containing the synthetic pL promoter with a similar fragment obtained from pCFM 636 (see U.S. Pat. No. 4,710,473) containing the pL promoter,

```
probe 1                                         (SEQ ID NO: 18)
5' CGG GTC CTC GAT GTC CAG AAA CTC CTG CTT GGG GGG TGC TGC
   TCC GCG GTA 3' probe 2                                         (SEQ ID NO: 19)
5' GAA CTT GGC CTG GTG TCC GTT GAT GTT CTT CTC CGT GAC CCA
   GTC CAT CCA 3' probe 3                                         (SEQ ID NO: 20)
5' GCA CTC ACA GCC CAT CTG GTA CCT GTG GTT CAG GCT CTT CTT
   CTG GGT GGC 3' probe 4                                         (SEQ ID NO: 21)
5' GGG GTT GCC GTA GAT GTC GTT GCC AGA GTC CAC CTC CTT CTT
   ATT GAC TGC 3'
```

A λgtll cDNA library made with mRNA isolated from human heart tissue (fetal aorta) was purchased from CLONTECH Laboratories, Inc. Approximately 10$^6$ phage were and substituting the small DNA sequence between the unique ClaI and KpnI restriction sites with the following oligonucleotide:

```
       ClaI                                              KpnI
5'    CGATTTGATTCTAGAAGGAGGAATAACATATGGTTAACGCGTTGGAATTCGGTAC 3' (SEQ ID
NO: 22)

3'       TAAACTAAGATCTTCCTCCTTATTGTATACCAATTGCGCAACCTTAAGC     5' (SEQ ID
NO: 23)
```

The pL DNA sequence inserted is as follows:

```
       AatII

5'         CTAATTCCGCTCTCACCTACCAAACAATGCCCCCCTGCAAAAAATAAATTCATAT

3'    TGCAGATTAAGGCGAGAGTGGATGGTTTGTTACGGGGGACGTTTTTTATTTAAGTATA

AAAAAACATACAGATAACCATCTGCGGTGATAAATTATCTCTGGCGGTGTTGACATAAA

TTTTTTGTATGTCTATTGGTAGACGCCACTATTTAATAGAGACCGCCACAACTGTATTT

TACCACTGGCGGTGATACTGAGCACAT    3' (SEQ ID NO: 24)
ATGGTGACCGCCACTATGACTCGTGTAGC 5' (SEQ ID NO: 25)
                  ClaI
```

A synthetic DNA fragment was constructed which contained a ribosome binding site, an initiation methionine codon, and codons for the first 42 amino acids of the mature human MI (FIG. 9). This fragment was first cloned into M13 mp11 from XbaI to BamHI to confirm the sequence by the dideoxy method of Sanger (Proc. Natl. Acad. Sci. USA, supra). This XbaI to BamHI fragment was then cloned from M13 mp11 into p1156HMIL to generate p1156 HMI2 (FIG. 8).

This plasmid was transformed into E. coli strain FM5 (ATCC deposit no. 53911) which contains a temperature-sensitive λCI repressor on the chromosome. The plasmid contains the λpL promoter/operator region and has a temperature sensitive replicon. When E. coli strain FM5 harboring p1156HMI2 is cultured at 28° C., the plasmid copy number is maintained at 10–20 copies/cell, and transcription from the λpL promoter is regulated by a temperature-sensitive repressor. Growth at 42° C. results in an increased copy number and a release of repression at the λpL promoter. Recombinant human metalloproteinase inhibitor begins to accumulate at elevated temperatures as a result of promoter activation and plasmid amplification. The λpL promoter lies just upstream from the ribosome binding site and the methionine initiation codon of human metalloproteinase inhibitor. The transcription terminator, t-oop, lies just downstream from the two translational stop codons near the 3' end of the gene. Strain FM5 harboring the plasmid p1156HMI2 was grown using the dual-feed media described by Tsai et al. [J. Indust. Microbiol. 2, 181–187 (1987)]. Induction was accomplished by a temperature shift to 42° C. when the optical density at 600 nm ($OD_{600}$) had reached about 30. The final $OD_{600}$ reached approximately 60. Recombinant human MI was expressed up to a level of 15 mg/OD-liter. The human MI was evident after SDS-PAGE with Coomassie blue staining (load equivalent to 0.4 mg wet weight of cells; reduced) as a prominent band with $M_r$ 24,000–28,000 which co-migrated with the band for purified bovine MI (Example 1). Other E. coli host cells can be used for expression as will be apparent to those skilled in the art.

EXAMPLE 5
Purification of E. coli-Expressed Recombinant Human Metalloproteinase Inhibitor.

The human MI is expressed in E. coli in insoluble, inactive form (so-called inclusion bodies). Isolation of active MI requires procedures for solubilization, purification, folding, and oxidation (disulfide formation) of the inclusion body MI. An example of such procedures is given below.

About 400 grams (wet weight) of cell paste of E. coli strain FM5 harboring plasmid p1156HMI2, grown as indicated in Example 4, was suspended in 1.5 liters of $H_2O$. The material was passed through a Manton-Gaulin homogenizer three times and then centrifuged for 45 min at about 4,000×g at 4° C. The supernatant was poured off and discarded. The pellets were resuspended in 1.5 liters $H_2O$ (4° C.) and centrifuged as above. The supernatant was poured off and discarded. The pellets were resuspended in 120 ml $H_2O$ and then diluted ten-fold with 20 mM Tris-HCl, pH 9.5. The pH was adjusted to 11.5 (using 1 N NaOH), and the mixture was left on ice for 15 min, and then centrifuged for 30 min at 11,300×g at 4° C. The supernatant was diluted four-fold with 20 mM Tris-HCl, pH 9.5. The pH was adjusted to 10–10.5 (with 1 N NaOH) and the mixture was stirred overnight at room temperature.

The pH of the mixture was lowered to 8.5 (using 1 N HCl) and the mixture was then loaded onto a DEAE-Sepharose Fast Flow (Pharmacia) ion exchange column (150 ml column volume) equilibrated in 20 mM Tris-HCl, pH 8.5. Bound material was eluted with a 2 liter gradient from 0 to 0.3 M NaCl in the Tris-HCl buffer. Fractions of 12 ml were collected at a flow rate of 8 ml/min. Aliquots (25 μl) of collected fractions were subjected to SDS-PAGE (15%, w/v, acrylamide; unreduced) with Coomassie blue staining. Fractions 38–54, which contained a fairly sharp band ($M_r$ about 22,000–23,000) corresponding to the MI polypeptide, were pooled (202 ml). Material thought to also represent the MI polypeptide, but having a slightly lower mobility and banding less sharply on SDS-PAGE, eluted later in the gradient and was not included in the pool.

The pooled material from DEAE-Sepharose Fast Flow was concentrated to 30 ml using an Amicon stirred cell (with YM5 membrane). The pH was adjusted to 5.4 (using 50% acetic acid) and the mixture was dialysed against 20 mM sodium acetate, pH 5.4. The material was then diluted with $H_2O$ to a final volume of 45 ml and applied to a CM-Sepharose Fast Flow (Pharmacia) ion exchange column (1 ml column volume) equilibrated in 20 mM sodium acetate, pH 5.4. Bound material was eluted using a 20 ml gradient from 0 to 0.4 M NaCl in the sodium acetate buffer. Fractions of 1 ml were collected at a flow rate of 0.1 ml/min. Aliquots (10 μl) of the fractions were analyzed by SDS-PAGE as above and those containing MI [fractions 11–18 (8 ml)] were pooled and then loaded directly onto a Sephacryl S-200HR gel filtration column (300 ml column volume) equilibrated in phosphate-buffered saline (PBS). Fractions of 4 ml were collected at a flow rate of 20 ml/h. Aliquots (20 μl) of the fractions were again analyzed by SDS-PAGE as above. Fractions 54–60 contained MI; to maximize purity, only fractions 56–59 were pooled (16 ml). Purity of MI in the pool, estimated by SDS-PAGE, was greater than 90% as judged by visual inspection of gels after SDS-PAGE with Coomassie blue staining. Total protein in the pool, measured by the method of Bradford (Anal. Biochem., supra) using BSA as standard, was about 8 mg. Inhibitory activity of this material was about 424 U/ml (specific activity about 865 U/mg) measured by the type I collagenase inhibition assay described in Example 1, section 2. Inhibitory activity of *E. coli*-derived human MI was also demonstrated in several other ways (Example 11).

A sample of the human MI preparation described (about 6.5 μg) was subjected to amino-terminal amino acid sequencing through 18 cycles, using the methods described in Example 2. The initial yield was 135 pmol and the repetitive yield was 94%. The major sequence obtained exactly matched that predicted from the nucleotide sequence for the mature human MI gene (Example 3; FIG. 2).

The material is purified to apparent homogeneity using methods such as that described in Example 1 for bovine MI or other methods evident to those skilled in the art.

EXAMPLE 6
Generation of Rabbit Polyclonal Antisera to Human Metalloproteinase Inhibitor.

Two types of preparation of metalloproteinase inhibitor were used for generation of rabbit polyclonal antisera. The first (used for injections on days 1, 7 and 21) was prepared as follows. About 14 g (wet weight) of cell paste from *E. coli* strain FM5 harboring plasmid p1156HMI2 (Example 3) was suspended in 50 ml H$_2$O and passed twice through a French Press device. The pellet fraction obtained by centrifugation was resuspended in a final volume of 10 ml containing sodium sarkosyl (2%, w/v), Tris-HCl (50 mM), dithiothreitol (50 mM) with pH of 8.5, and incubated at 50° C. for 10–15 min and room temperature for 2 h, for solubilization of MI. After centrifugation of this mixture, a supernatant fraction (7.2 ml) containing MI was obtained and subjected to gel filtration on a Sephacryl S-200 column (265 ml column volume) equilibrated in 20 mM Tris-HCl, 1% (w/v) sodium N-lauroyl sarcosine, pH 8. Fractions of 2.9 ml were collected at a flow rate of 14 ml/h. Fractions 65–75 (31 ml) containing MI [as judged by SDS-PAGE with silver-staining; aliquots (0.5 μl; reduced) of fractions were run on gels containing 12.5% (w/v) acrylamide], were pooled, dialyzed thoroughly against 20 mM Tris-HCl, pH 8, concentrated to 6.5 ml using an Amicon stirred cell (with YM10 membrane), and filtered through a 0.45μ filter. The MI concentration in this preparation was about 1 mg/ml. The second type of preparation (used for injections on days 35 and 56) was that of Example 4, with MI at a concentration of 0.4–0.5 mg/ml.

The MI preparations were injected into 3 New Zealand white rabbits (5–8 lb. initial weight). Each rabbit was immunized on day 1 with 0.2 mg MI emulsified in an equal volume of Freund's complete adjuvant. A total volume of not more than 2 ml (1:1, MI:adjuvant) per rabbit was injected subcutaneously in at least 6 sites along the hindquarters. Further boosts (days 7, 21, 35 and 56) were performed by the same procedure, with the substitution of Freund's incomplete adjuvant.

Rabbits were bled by ear vein puncture on the day before the first injection (preimmune serum) and on days 28 and 63. Blood was collected into vacuum tubes and allowed to clot for 16 hours at room temperature. The clot was removed and the serum spun for 10 minutes at 2200 rpm to remove any remaining red blood cells. Serum, with sodium azide added to a final concentration of 0.01% (w/v), was stored at −20° C.

Serum was titered using a solid-phase radioimmunoassay; see Tsu et al., "Solid Phase Radioimmunoassays", pp. 373–397 in *Selected Methods in Cellular Immunology*, B. B. Mishel and S. M. Shiigi, eds., Freeman, San Francisco (1980), and *Hybridoma Technology in the Biosciences and Medicine*, Timothy A. Springer, ed., Plenum Press (1985), pp. 29–36. Metalloproteinase inhibitor was diluted to 0.5 μg/50 ul in carbonate-bicarbonate buffer, pH 9.2 and incubated for 2 h at room temperature in polystyrene wells (50 ul/well). Antigen solution was decanted; wells were then filled with 5% (w/v) BSA for 30 minutes at room temperature to block remaining binding sites on plastic. Dilutions of rabbit serum in PBS containing 1% (w/v) BSA were added to wells (50 ul/well) after the 5% (w/v) BSA was decanted. Incubations were carried out for 2 h at room temperature, then wells were washed with an imidazole-buffered saline containing 0.02% (w/v) Tween 20. $^{125}$I-Labeled protein A (100,000 cpm/50 ul) was added to wells and incubation was carried out for 30 min at room temperature, followed by a second wash. Wells were snapped apart and counted in a gamma counter. Cpm values were graphed against antiserum dilution to determine 50% titer (the dilution at which the antiserum binds half of the maximum counts bound). Sera obtained from the day 28 bleeds had titers ranging from 1:200 to 1:2500. Sera obtained from the day 63 bleeds had titers ranging from 1:800 to 1:4500.

These antisera were also used for SDS-PAGE with immunoblotting. As indicated in Examples 8 and 9, the antibody recognized a protein band of the expected $M_r$ in preparations of bovine MI, *E. coli*-expressed recombinant human MI, and CHO cell-expressed recombinant human MI.

EXAMPLE 7
Expression of Recombinant Human Metalloproteinase Inhibitor by Yeast Cells.

The human MI gene was from pUC HMI (Example 3). The MI gene was isolated from pUC HMI as a 586 base pair (bp) PstI to StuI DNA fragment. A synthetic DNA linker with HindIII and PstI sticky ends was used to fuse the MI gene to the yeast MFα1 in the vector pUC119αG4 (FIG. 10A).

The synthetic DNA linker was:
AGCTTGGACAAGAGATGCA
(HindIII) ACCTGTTCTCT (PstI)
The vector pUC119αG4 contains a yeast glyceraldehyde-3-phosphate dehydrogenase promoter (GPD-P) followed by the pre-pro sequence (αF-s) and the transcription termination sequence (αF-t) of yeast mating factor α.

The vector pUC119αG4, in detail, consists of the following (see FIG. 10A):
I. pUC119 with deletion of HindIII, SalI, SstI and SmaI sites: pUC119 was digested with HindIII plus SalI, followed by S1 nuclease treatment to generate blunt ends, then ligation. The resulting plasmid was further digested with SstI plus SmaI, followed by S1 nuclease treatment, then ligation, resulting in deletion of HindIII, SalI, SstI and SmaI sites. An expression casette was then introduced into the remaining unique BamHI site.

II. The expression casette consists of the following:

(i) a 675 bp HindIII to BamHI fragment containing the yeast glyceraldehyde-3-phosphate dehydrogenase promoter (GPD-P) [Bitter et al., Gene 32, 263–278 (1984)], where the HindIII site was removed and a BamHI site was added. This was accomplished by digestion with HindIII followed by end-filling with the Klenow fragment of DNA polymerase I. The DNA fragment containing the end-filled HindIII site was blunt-end ligated into the SmaI site of pUC19.

(ii) A GPD-α-factor linker (Sau3A)           met arg phe pro ser ile phe thr ala (SEQ ID NO: 26)

GATCACACATAAATAAACAAAATG AGA TTT CCT TCA ATT TTT ACT GCA (SEQ ID NO: 27)

TGTGTATTTATTTGTTTTAC TCT AAA GGA AGT TAA AAA TG (PstI) (SEQ ID NO: 28)

(iii) A 218 bp PstI to HindIII fragment containing the α-factor pre-pro leader sequence from pαC3 [Zsebo et al., J. Biol. Chem. 261, 5858–5865 (1986); Bitter et al., Methods in Enzymol. 153, 516–544 (1987)].

(iv) A linker for joining the α-factor pre-pro leader to the α-factor terminator sequence such as:

HindIII SphI SstI SmaI XhoI BglII            (SalI)

AGCTTGCATGCGAGCTCCCCGGGCTCGAGATCTGATAACAACAGTGTAGATGTAACAAAA (SEQ ID NO: 29)

ACGTACGCTCGAGGGGCCCGAGCTCTAGACTATTGTTGTCACATCTACATTGTTTTAGCT (SEQ ID NO: 30)

(v) An α-factor terminator sequence on an approximately 250 bp SalI to BamHI fragment from pαC3, with the SalI site being destroyed after joining to the linker in (iv).

The α-factor-MI gene fusion was accomplished by digesting pUC119αG4 with HindIII and SmaI followed by ligation with the synthetic DNA linker and the MI DNA fragment. The resultant plasmid pUC119αG4-HMI depicted in FIG. 10A contains a yeast glyceraldehyde phosphate dehydrogenase promoter (GPD-P) followed successively by the α-factor pre-pro leader from the yeast MFαl gene, the synthetic DNA linker above, the human metalloproteinase inhibitor gene DNA segment and α-factor transcription terminator. The 1800 bp BamHI DNA fragment containing the elements above was isolated from pUC119αG4 by a partial digest with BamHI and inserted into the BamHI site of the yeast-E. coli shuttle vector pYE3 resulting in the plasmid pYE3αG4-HMI (FIG. 10C).

The plasmid pYe3 is shown in FIG. 10B and consists of the following:

I. Yeast 2μ (B form) plasmid in pGT41 [Tschumper et al., Gene 23, 221–232 (1983)] where the 2500 bp BamHI to SalI LEU 2 gene segment was deleted by digestion with BamHI plus SalI, and this treatment was followed by mungbean nuclease treatment to generate blunt ends, followed by ligation.

II. A polylinker, whose sequence is shown below, was inserted into a EcoRI site of the modified 2μ plasmid in (I) as shown in FIG. 10B.

AATTC GATATC GAT GGTACC CGG GATCC GTCGAC AGATCT G (SEQ ID NO: 31)

G CTATAG CTA CCATGG GCC CTAGG CAGCTG TCTAGA CTTAA (SEQ ID NO: 32)

EcoRI EcoRV ClaI KpnI SmaI BamHI SalI    BglII   EcoRI

III. A 852 bp BglII to EcoRI fragment containing the TRP 1 gene [Tschumper et al. Gene 10, 157–166 (1980)] inserted into the BglII and EcoRI sites of the polylinker in (II).

The plasmid pYE3αG4-HMI was grown in E. coli strain DH5α, the plasmid DNA was isolated and the DNA was transformed into the S. cerevisiae yeast strain EG45°. Other yeast host cells can also be used as will be apparent to those skilled in the art.

The strain EG45° (supra) was a mutant of the yeast strain SE7-6. The strain SE7-6 (Matα, trp1 deletion, pep4-3, GAL, cup1) was constructed using standard yeast genetic techniques. It was derived from crosses of several yeast strains including: (1) YSDP4 (ATCC 20734) which contains a mutation in the PEP4 gene; (2) a strain with an ability to grow on galactose [BWG1-7A obtained from L. Guarente, see Guarente et al., Proc. Natl. Acad. Sci. USA 79, 7410–7414 (1982) and Cell 36, 503–511 (1984)]; (3) a strain with a deletion of the TRP1 gene (YNN282 Yeast Genetic Stock Center, Berkeley, Calif.); and (4) a strain with sensitivity to copper (x36567D Yeast Genetic Stock Center, Berkeley, Calif.). The selection of SE7-6 was made based on its ability to grow on galactose and to secrete heterologous proteins efficiently.

Figure 11:
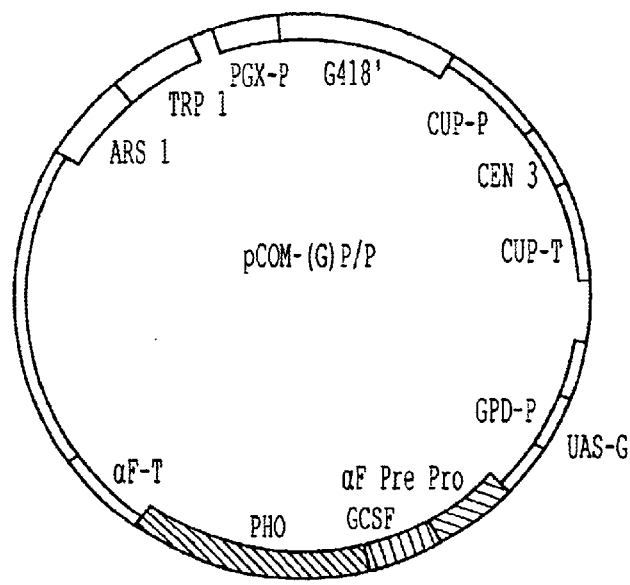
FIG. 11 shows vectors used for isolation of yeast secretion mutants.

To isolate EG45°, the strain SE7-6 was transformed with the plasmid pCOM(G)P/P. The plasmid pCOM(G)P/P contains an amplifiable copy number system (FIG. 11). It can be transformed into yeast trp1 cells by selection for tryptophan prototrophy via the TRP1 ARS1 yeast DNA segment (see Bitter et al., Methods Enzymol., supra). Under normal conditions the plasmid is stable at a copy number of one per cell. Growth on copper-containing medium induces transcription from the CUP promoter (CUP-P) which inhibits centromere (CEN3) function. CUP-T is the CUP terminator region. Therefore copy number increases and plasmid stability decreases. Following removal of copper the plasmids stabilize. Normally the copy number returns to one per cell; however selection for G418 resistance via the Tn5 gene [Jiminez et al. Nature 287, 869–871 (1980)] [controlled by the yeast PGK promoter.(PGK-P)] results in cells containing 5–10 copies of plasmid per cell which are stably maintained.

Transformation of EG45° was done by electroporation of plasmid DNA into yeast cells at 900 volts for 5 milliseconds at 25 microfarads in a Bio-Rad gene pulser. Electroporated cells were plated on SD-CAA agar which contains 6.7 g/L yeast nitrogen base without amino acids (Difco), 2% (w/v) glucose, 0.5% (w/v) casamino acids (Difco) and 2% (w/v) agar, and transformed cells were obtained by growth at 30° C.

The transformed cells were grown in a 15 L fermentor using fed-batch fermentation. The medium composition is shown below:

| Chemicals | Batch medium | Feed medium |
|---|---|---|
| Casamino acids | 25 g/L | 125 g/L |
| Yeast extract | 5 g/L | 10 g/L |
| $(NH_4)_2PO_4$ | 3.8 g/L | 5 g/L |
| $KH_2PO_4$ | 13.5 g/L | 2.8 g/L |
| Glucose | 2 g/L | 533 g/L |
| Inositol | 0.02 g/L | 0.03 g/L |
| $MgSO_4 \cdot 7H_2O$ (1M) | 4 ml/L | 15 ml/L |
| Trace metal solution[a] | 3 ml/L | 6.6 ml/L |
| Vitamin solution[a] | 3 ml/L | 6.6 ml/L |
| Streptomycin sulfate | 0.23 g/L | |
| Thiamine (10 g/100 ml) | 0.6 ml/L | 1.6 ml/L |

[a]Trace metal solution and vitamin solution were the same as described by Tsai et al., J. Industrial. Microbiol. 2, 181–187 (1987).

The pH of the medium was maintained at 6.0 and the temperature at 25° C. Dissolved oxygen was controlled by aeration, back pressure and agitation. Cells were grown to $OD_{600}$ of 85–95.

EXAMPLE 8
Characterization of Yeast-secreted Recombinant Human Metalloproteinase Inhibitor.

Culture medium containing yeast-expressed recombinant human MI was harvested by centrifugation to remove the cell paste. The supernatant fraction was subjected to SDS-PAGE (reducing conditions) with silver-staining. A band migrating with $M_r$ of about 26,000 (24,000–28,000) was observed for supernatants produced by yeast (strain EG45°) transformants containing pYE3αG4-HMI. The polypeptide represented by this band was present at about 25 to 50 mg per liter of supernatant. The $M_r$ 26,000 band was not observed in control fermentor supernatants. The $M_r$ 26,000 band had the same mobility on SDS-PAGE as MI purified from bovine endothelial cell conditioned medium (Example 1). By SDS-PAGE with silver-staining performed on aliquots (10 μl) of MI-containing yeast supernatants in unreduced conditions, the Mr 26,000 band was absent, and there was instead an $M_r$ 22,000–23,000 band. Material represented by the $M_r$ 22,000–23,000 band was present at about 2–5 mg per liter of supernatant, and was not seen in control supernatants. To demonstrate that the $M_r$ 26,000 (reduced) and $M_r$ 22,000–23,000 (unreduced) bands represented human MI, a polyclonal antibody raised in rabbits against human MI produced in E. coli (Example 6) was used. SDS-PAGE with immunoblotting (Burnette, Anal. Biochem., supra) was performed using this antibody preparation and a Vectastain ABC kit (Vector laboratories) containing biotinylated anti-rabbit immunoglobulin, avidin, and biotinylated horseradish peroxidase. Immunoreactive bands were seen for supernatants from the yeast strain transfected with the MI gene-containing plasmid (10 μl loaded) and not for control supernatants. [$M_r$ 26,000 and $M_r$ 18,000 bands were present for reduced samples and $M_r$ 22,000–23,000 band for unreduced samples. The $M_r$ 18,000 (reduced) band is presumed to be a proteolytic breakdown fragment of MI.] The antibody also reacted in immunoblots with MI purified from bovine enthothelial cell conditioned medium (350 mU) and with E. coli-produced human MI (0.3 μg) which indicates that the bands observed in yeast supernatants did in fact represent human MI.

EXAMPLE 9
Expression of Human Metalloproteinase Inhibitor in Chinese Hamster Ovary Cells.

1. Construction of an Expression Vector.

To generate expression plasmids, the NcoI to EcoRI fragment of pUC HMI (Example 3) containing the intact coding sequence of human MI [including the sequence coding for the 26-amino acid leader FIG. 2)] was first subcloned into PCFM 1156, from the NcoI to the EcoRI restriction site to give plasmid p1156HMINR. The plasmid PCFM 1156 was derived from plasmid PCFM 836 (see U.S. Pat. No. 4,710,473 hereby incorporated by reference), by destroying the two endogenous NdeI restriction sites, end filling with T4 DNA polymerase followed by blunt end ligation and substituting the small DNA sequence between the unique ClaI and KpnI restriction sites with the following oligonucleotide:

```
         ClaI                                                    KpnI
    5'   CGATTTGATTCTAGAAGGAGGAATAACATATGGTTAACGCGTTGGAATTCGGTAC    3'  (SEQ ID NO: 33)

3'       TAAACTAAGATCTTCCTCCTTATTGTATACCAATTGCGCAACCTTAAGC      5'  (SEQ ID NO: 34)
```

The human MI cDNA was retrieved from plasmid p1156HMINR as a 0.65 kb HindIII to StuI fragment. This fragment was then cloned into the expression vector pDSRα2 to generate plasmid pDSFα2-MI.

Figure 12:
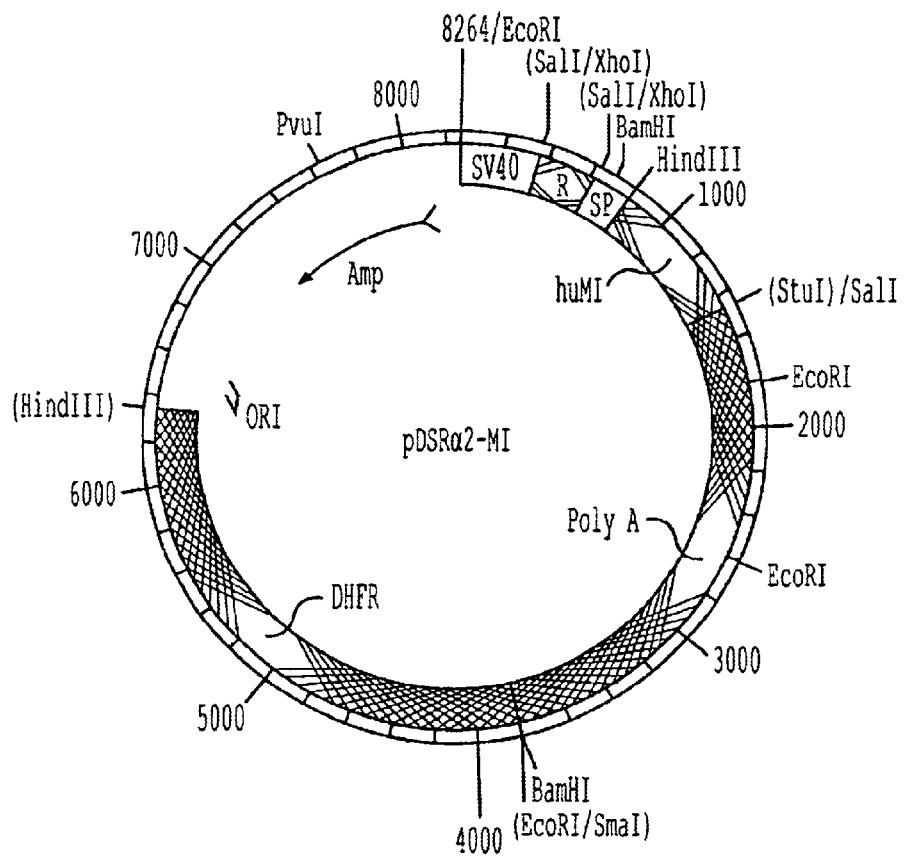
FIG. 12 shows the structure of mammalian cell expression vector pDSRα2-MI.

Plasmid pDSRα2 has the following important features (following the map in FIG. 12 in a clockwise direction):

(a) SV40 early promoter/enhancer and origin of replication; composed of SV40 sequences between PvuII (SV40 nucleotide map coordinate #272) and HindIII (map coordinate #5172) sites. [*DNA Tumor Viruses*, J. Tooze, ed., Cold Spring Harbor Laboratories, Cold Spring Harbor, N.Y. (1981), pp. 801–804].

(b) A 267 bp fragment containing the "R" element and part of the "U5" sequences of the long terminal repeat (LTR) of human T-cell leukemia virus type 1 (HTLV-1). This fragment maps at the exact 5' end of "R" (position 354) to the Sau3A site in the U5 sequences (position 620) [Seiki et al. Proc. Natl. Acad. Sci. USA 80, 3618–3622 (1983)].

(c) A fragment composed of SV40 16S, 19S splice donor/acceptor signals (map coordinates #502–560 and #1410–1498 joined by an BamHI linker).

The structural organization of the above three segments (a), (b) and (c) is identical to the published vector pCD-SRα [Takebe et al., Mol. Cell. Biol. 8, 466–472 (1988)] with the following modifications: (1) at the 5' end of segment (a), the HindIII site has been destroyed by end-filled ligation done with the Klenow fragment of DNA polymerase I; (2) the original XhoI site between segments (a) and (c) has been destroyed through the insertion of segment (b); (3) at the 3' end of the (c) segment, the original PstI site was changed into a HindIII site.

(d) A transcription termination/polydenylation signal residing on a SalI to BamHI fragment of 2.4 kb. This fragment was obtained from the 3' portion of the α-subunit of bovine pituitary glycoprotein hormone α-FSH (follicle stimulating hormone). A BstXI site at the beginning of the last exon was mutagenized to a SalI site. The 3' end of the fragment continued to the nearest downstream BamHI site. This 2.4 kb fragment was subcloned into a pUC vector and then retrieved as a SalI to SmaI fragment for further construction of the expression vector.

(e) A mouse dihydrofolate reductase (DHFR) minigene containing the endogenous mouse DHFR promoter, the cDNA coding sequences, and the DHFR transcription termination/polyadenylation signals all as an EcoRI to HindIII fragment of 2.5 kb, retrieved initially from plasmid pMg 1 [Gasser et al., Proc. Natl. Acad. Sci. USA 79, 6522–6526 (1982)]. Both of the terminal restriction endonuclease sites, i.e., the 5' EcoRI and the 3' HindIII, were destroyed upon construction of the expression vector.

(f) The "poisonless" pBR322 sequences extending from the HindII site (map coordinate #2448) to EcoRI site (map coordinate #4362) and containing the ampicillin resistance marker gene and the origin for replication of the plasmid in *E. coli*.

Through multiple steps of subcloning, these six segments of DNA [(a)–(f)] were finally ligated to generate the expression vector pDSRα2; several of the original restriction endonuclease cleavage sites were destroyed or altered during the process. The final structure of the plasmid pDSRα2-MI is thus illustrated in FIG. 12 in its circular configuration with these changes clearly depicted.

2. Transfection Conditions.

DHFR-deficient (DHFR⁻) Chinese hamster ovary (CHO) cells [Chasin & Urlaub, Proc. Natl. Acad. Sci. USA 77, 4216–4280 (1980)] were maintained routinely in Dulbecco Modified Eagle's Medium supplemented with 5% (v/v) fetal bovine serum (FBS), L-glutamine (292 μg/ml), non-essential amino acids (100 μM), hypoxanthine (13.6 pg/ml), thymidine (7.6 μg/ml), penicillin (100 U/ml) and streptomycin sulfate (100 μg/ml).

One million cells (plated on a 60 mm dish one day prior to transfection) were transfected separately with 20 μg of pDSRα2-MI11 or pDSRα2-MI14 (two independently isolated plasmids) plasmid DNA by a modified calcium phosphate precipitation method [Chen et al., Mol. Cell. Biol. 7, 2745–2752 (1987)]. Three days post-transfection, the cells were split to eight 100 mm dishes. At this point, medium lacking hypoxanthine and thymidine, and containing 10% (v/v) dialyzed FBS, was used for the selection of transfectants. Medium was changed every 2–3 days to ensure the selection. At the end of the second week after transfection, twenty-four stable transfectants were selected from each set of dishes for analysis for transcription and translation of the MI gene.

3. Analysis for mRNA Transcribed from the Recombinant Human MI Gene.

Total cytoplasmic RNA from transfected CHO cells was prepared as described in Resendez et al. [J. Cell Biol. 103, 2145–2152 (1986)]. Cellular RNA (7.5 μg) was separated by 1% formaldehyde-formamide denaturing agarose gel electrophoresis and transferred onto a GeneScreen Plus membrane. Radiolabeled HindIII to PvuI fragment of pDSRα2-MI11 was used to identify the human MI transcript using the hybridization conditions described by Lin et al. [Gene 44, 201–209 (1986)]. A single RNA band was observed in four of the seven individual stable clones analyzed. The size of the message was 1.5 kb as expected from the construct.

4. Protein Analysis and Quantitation.

Recombinant human MI was identified and quantitated by SDS-PAGE with immuno-blotting with antibody against human MI as described in Example 8. Conditioned media from stable transfected clones (serum-free; 10–50 μl aliquots) were analyzed. Results indicated that transfected CHO cells secrete a $M_r$ 26,000 (24,000–28,000) (reduced) protein which can be recognized by the antibody. This protein co-migrates with the *E. coli*-produced recombinant human MI. The transfectant with highest MI expression produced about 1 mg/liter/day on a confluent 100 mm tissue culture dish without amplification.

5. Amplification of Expression.

MI expression by transfected CHO cell clones was amplified by the use of methotrexate [Kaufman and Sharp, J. Mol. Biol. 159, 601–621 (1982)] in stages of increased concentration (stages of 10 nM, 30 nM, 100 nM, and 300 nM methotrexate). Transfected clones subjected to the 10 nM methotrexate amplification stage when grown in roller bottles as described in Example 10, led to conditioned medium containing MI at levels as high as 20–30 mg/liter at the time of the 6–7 day harvesting. After the 300 nM amplification stage, MI levels as high as 50–60 mg/liter could be obtained upon culturing in the roller bottles.

6. Bioactivity Assay.

Activity could be detected in transfected CHO cell supernatants by the type I collagenase inhibition assay described in Example 1. Results are given in Example 10 (Table 8).

EXAMPLE 10

Purification of Chinese Hamster Ovary Cell-expressed Recombinant Human Metalloproteinase Inhibitor.

CHO cells, transfected with the expression vector carrying the human MI gene as described in Example 9 and subjected to the 10 nM methotrexate amplification stage (Example 9), were grown in roller bottles in serum-free medium, as follows. Initially, the cells were grown in spinner flasks in medium containing Dulbecco's modified MEM supplemented with dialyzed fetal calf serum (5%, v/v), glutamine, and non-essential amino acids, plus F12 nutrient medium; the MEM and F12 medium were present at 50:50 (v:v). Cells were then transferred to 850 cm² roller bottles ($2 \times 10^7$ cells/bottle) containing the same medium.

After three to four days at 37° C., the cell monolayers were washed with PBS and fresh medium (150–200 ml/bottle; as above, but lacking serum) was added. Conditioned medium was harvested 6–7 days later, and replaced with fresh medium again. Six to 7 days later, the additional conditioned medium was harvested.

All subsequent work was done at 4° C. unless otherwise indicated. To 20 liters of conditioned medium, sodium azide (final concentration 0.02%, w/v) and the protease inhibitors pepstatin A (final concentration 1 µg/ml) and phenyl-methanesulfonyl chloride (PMSF; final concentration 0.6 mM) were added. The medium was concentrated and diafiltered against 1 mM imidazole, 1 M NaCl, pH 7.5 (adjusted with HCl), using a Millipore Pellicon tangential flow ultrafiltration apparatus with 10,000 molecular weight cutoff polysulfone membrane cassette (5 ft$^2$ membrane area). Pump rate was about 500 ml/min and filtration rate about 100 ml/min. The final volume of recovered sample was 1 liter. This sample was applied to a Chelating Sepharose Fast Flow (Pharmacia) column (400 ml column volume) which had been saturated with $Cu^{2+}$ by passing a solution of $CuSO_4$ over the column, and then equilibrated with the 1 mM imidazole, 1 M NaCl, pH 7.5 buffer. Flow rate was 800 ml/h. After sample application, the column was washed with about 1 liter of the imidazole starting buffer. The MI, which was bound to the column, was then eluted with a linear gradient (20 liters total volume) from the starting buffer to 20 mM imidazole, 1 M NaCl, pH 7.5. Fractions of 420–600 ml were collected and aliquots (0.00033% of fraction volume) were subjected to SDS-PAGE (12.5%, w/v, acrylamide; reduced) with silver-staining. A fraction of 600 ml, representing elution volume 1810–2410 ml in the gradient, contained most of the MI polypeptide (visualized as a band of $M_r$ about 26,000). This fraction was concentrated to about 100 ml using an Amicon stirred cell with an Amicon YM10 membrane, dialyzed against 20 mM Tris-HCl, 1 mM $CaCl_2$, pH 8.5, and applied to a Q-Sepharose Fast Flow (Pharmacia) ion exchange column (40 ml column volume) equilibrated in the same buffer. Flow rate was 120 ml/h. After sample application, the column was washed with about 100 ml of the starting Tris-HCl buffer. The MI, which was bound to the column, was then eluted with a linear gradient of 0 to 0.5 M NaCl in the starting Tris-HCl buffer (total gradient volume 1200 ml). Fractions of 12.6 ml were collected. Aliquots (1 µl) of the fractions were again analyzed by SDS-PAGE as above, and those containing MI (fractions 25–32 of the gradient) were pooled (100 ml total volume), concentrated to 40 ml using an Amicon stirred cell as above, and applied to a Sephacryl S-200 HR (Pharmacia) gel filtration column (5×146 cm) equilibrated with PBS. Fractions of 13 ml were collected, at a flow rate of 80 ml/h. Aliquots (2 µl) of the fractions were again analyzed by SDS-PAGE as above, and those containing MI (fractions 81–94) were pooled (180 ml). Purity of the MI in the pool, as judged by SDS-PAGE with silver-staining was greater than 95%. The purification scheme is summarized in Table 8.

TABLE 8

Purification of human recombinant MI from CHO-cell conditioned medium

| Step | Volume (ml) | Total protein (mg)$^a$ | Total activity (units)$^c$ | Specific activity (units/mg) |
| --- | --- | --- | --- | --- |
| Conditioned medium | 20,000 | 2870 | 520,000 | 180 |
| Chelating Sepharose | 600 | 380 | 334,000 | 880 |
| Q-Sepharose | 100 | 310 | 630,000 | 2030 |
| Sephacryl S-200 HR | 180 | 260$^b$ | 264,000 | 1015 |

$^a$Determined by the method of Bradford (Anal. Bioch., supra) using BSA as standard, except where indicated otherwise.
$^b$Determined by $A_{280\ nm}$, using a value of 1.82 for the absorbance at 280 nm of a 1 mg/ml solution.
$^c$Activity was determined by the collagen film assay (Example 1, section 2).

Inhibitory activity of the purified material was demonstrated by the type I collagenase inhibition assay (Table 8), and by several other in vitro (Example 11) and in vivo (Example 12) methods.

The recovery of in vitro inhibitory activity was approximately 50%, and 5.6-fold purification was required. The final preparation had a specific activity of 1015 units/mg, which is similar to that observed for purified natural bovine MI [DeClerck, Y. A. et al. (1989) J. Biol. Chem. 264:17445–17453]. By SDS-polyacrylamide gel electrophoresis, the expected protein band with apparent molecular weight of 21,500 (unreduced) and 25,000 (reduced) was present, purity was judged as greater than 95%. As mentioned above, the mobility shift observed upon SDS-polyacrylamide gel electrophoresis after reduction corresponds to that observed for natural bovine MI [DeClerck, Y. A. et al. (1989) J. Biol. Chem. 264:17445–17453] and is characteristic of proteins with intrachain disulfide bonds. This result indicates that the disulfide structure of the recombinant-derived material matches that of the natural protein. Using Ellman's reagent [Ellman, G. L. (1984) Arch. Biochem. Biophys. 82:70–77] in the presence of denaturing agents, no reactivity was found with the rMI, suggesting that all 12 cysteine residues are in disulfide linkage. The 12 cysteine residues of TIMP align precisely with those of rMI [Boone et al., Proc. Natl. Acad. Sci. USA 87:2800–2804 (1990)], and assignments for the 6 disulfide bonds in TIMP have recently been reported [Williamson, R. A., et al. (1990) Biochem. J. 268:267–274]. By automated amino terminal amino acid sequencing carried out through 20 cycles [DeClerck et al., J. Biol. Chem. 264:17445–17453 (1989)], the purified material showed the sequence expected for the mature protein [Boone, T. et al. (1990) Proc. Natl. Acad. Sci. USA 87:2800–2804]. Thus the 26-amino acid leader sequence encoded by the plasmid pDSRα2MI is efficiently removed during synthesis and secretion of the rMI by CHO cells. From absorbance at 280 nm and quantitative amino acid composition analysis, a value of 1.82 for $$\varepsilon\frac{0.1\%}{280}$$

was obtained and used to determine concentrations of working rMI solutions.

Like natural bovine MI [DeClerck, Y. A. et al. (1989) J. Biol. Chem. 264:17445–17453], the human rMI appears to be unglycosylated (note that the bovine and human MI cDNAs both encode polypeptides lacking N-linked glycosylation sites [Boone, T. et al. (1990) *Proc. Natl. Acad. Sci. USA* 87:2800–2804] and elutes from gel filtration columns with apparent molecular weight of about 20,000–25,000 relative to proteins used as molecular weight.

A sample of this human MI preparation (about 27 μg) was subjected to amino-terminal amino acid sequencing through 20 cycles, using the methods described in Example 2. The initial yield was 923 pmol and the repetitive yield was 90–93%. The major sequence obtained exactly matched that predicted for mature human MI based on the nucleotide sequence of the human MI gene (Example 3; FIG. 2).

Additional methods that are of utility in the purification of the human MI from CHO cell conditioned medium include cation exchange chromatography [e.g. using CM-Sepharose Fast Flow (Pharmacia) at pH 4.5], hydrophobic interaction chromatography [e.g. using phenyl-Sepharose CL-4B (Pharmacia)], and other methods evident to those skilled in the art.

EXAMPLE 11

Demonstration of in vitro Inhibitory Activities in Recombinant Human MI Preparations.

The data described in this Example were obtained using *E. coli*-derived recombinant human MI [prepared as in Example 5, where so indicated; otherwise, the *E. coli*-derived material used was prepared essentially as in Example 5 except that dithioerythritol (5 mM) was present during the pH 11.5 treatment described in Example 5, and the material was held at pH 11 overnight and then made 2 mM in CaCl$_2$ and clarified by centrifugation prior to the DEAE-Sepharose chromatography; this latter material had inhibitory activity of about 369 U/ml (specific activity about 355 U/mg) measured by the type 1 collagenase inhibition assay described in Example 1, section 2] or CHO-derived recombinant human MI prepared as in Example 10.

1. Type I Collagenase Inhibition; SDS-gelatin PAGE; SDS-gelatin PAGE with Proteinases as Samples; Inhibition of Specific Collagen Cleavage.

Figure 13:
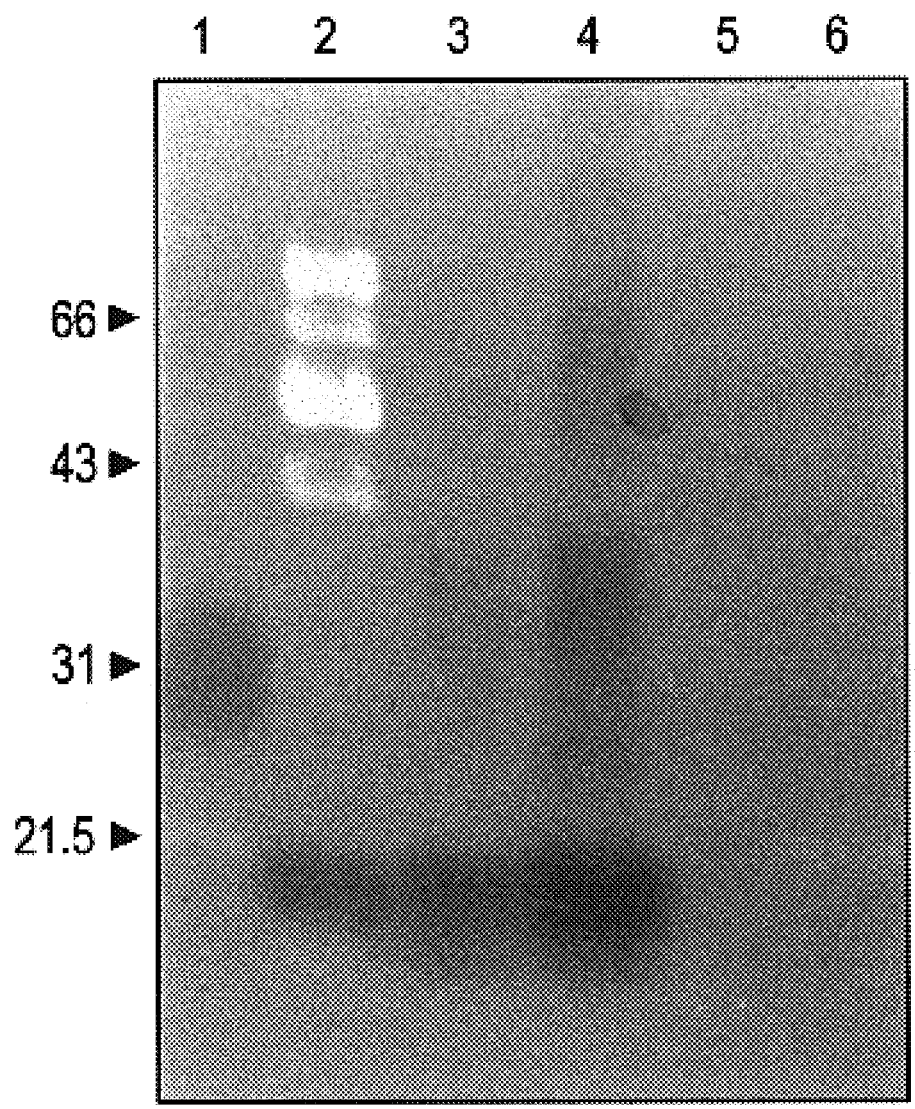
FIG. 13 shows SDS-gelatin PAGE for bovine metalloproteinase inhibitors and for recombinant human metalloproteinase inhibitor (MI) produced in *E. coli*.

*E. coli*-derived human MI was also analyzed by SDS-gelatin PAGE (FIG. 13; method as described in Example 1, section 4b). The legend to FIG. 13 is as follows (all samples were unreduced):

Lane 1, peak II-derived inhibitor from bovine endothelial cells (24 mU);

Lane 2, peak I-derived inhibitor (MI) from bovine endothelial cells (50 mU);

Lane 3, human MI prepared from *E. coli* (Example 5; 92 mU);

Lane 4, human MI preparation from *E. coli* (Example 5; 420 mU);

Lane 5 and 6, buffer only lanes. Noting the dark zones in lanes 1–4, it is apparent that all of the indicated inhibitor preparations, including the recombinant preparations from *E. coli*, have proteins of the expected molecular weights with inhibitory activity as judged by this method.

Figure 14:
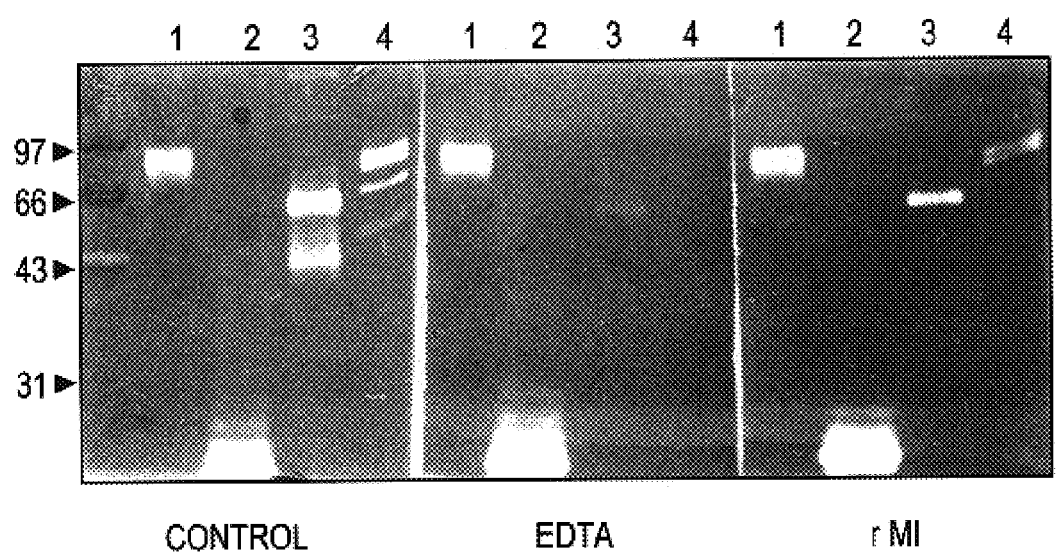
FIG. 14 shows effect of EDTA and of *E. coli*-produced recombinant human metalloproteinase inhibitor (MI) on gelatinolytic proteinase run on SDS-gelatin PAGE.

The method of SDS-gelatin PAGE with proteinases as samples (Example 1, section 4c) was also used to analyze the *E. coli*-produced recombinant human MI (FIG. 14). In FIG. 14, lanes marked "control" were incubated overnight with no inhibitor additions; lanes marked "EDTA" were incubated with 20 mM EDTA present; lanes marked "rMI" were incubated with *E. coli*-produced human MI (preparation of Example 4, 423 mU/ml). The samples electrophoresed prior to the overnight incubations were: lanes 1, human plasmin, 50 μg; lanes 2, bovine trypsin, 0.3 μg; lanes 3, 5 μl of 100-fold concentrated and APMA-activated conditioned medium from metastatic tumor cells [c-Ha-ras-transfected rat embryo fibroblasts, as source of type IV collagenase; conditioned medium prepared according to Garbisa et al., Canc. Res. 47, 1523–1528 (1987)]; lanes 4, APMA-activated conditioned medium from TPA-treated rabbit synovial fibroblasts (4 mU of collagenase I activity loaded; see Example 1, section 2). It is apparent that the recombinant MI inhibits the type I and type IV collagenases, but does not inhibit plasmin and trypsin (which are not metalloproteinases). EDTA also inhibits the collagenases, as expected.

The recombinant human MI from *E. coli* also inhibited the specific collagen cleavage characteristic of mammalian collagenases (see Example 1 and FIG. 7). Experiments showing this were done essentially as described for FIG. 7 in Example 1, using the recombinant human MI (Example 5) at about 2 μg/ml in the incubations. Results were equivalent to those shown in FIG. 7 for the bovine MI from endothelial cells.

Human MI from CHO cells had inhibitory activity of about 1537 U/ml (specific activity about 1067 U/mg measured by the type I collagenase inhibition assay described in Example 1, section 2). It is noted that this specific activity, and specific activity in other assays described below, is higher for the recombinant human MI from CHO cells than for that from *E. coli*. It is expected that this difference is due to the fact that some portion of the polypeptide chains in the *E. coli*-derived preparation are not in the native conformation and may also have incorrect disulfide bonds; and that one skilled in the art can arrive at procedures for solubilization, folding, oxidation (disulfide bond formation), and purification of *E. coli* derived human MI such that *E. coli*-derived human MI would have specific activities comparable to those of CHO cell-derived human MI.

Recombinant human MI from CHO cells also had inhibitory activity as judged by SDS-gelatin PAGE, and by inhibition of the specific collagen cleavage characteristic of mammalian collagenases. In each case the results obtained were similar to those described in the preceding paragraphs for recombinant human MI from *E. coli*.

2. Inhibition of Metalloproteinases Secreted by Metastatic Cells.

Figure 15A:
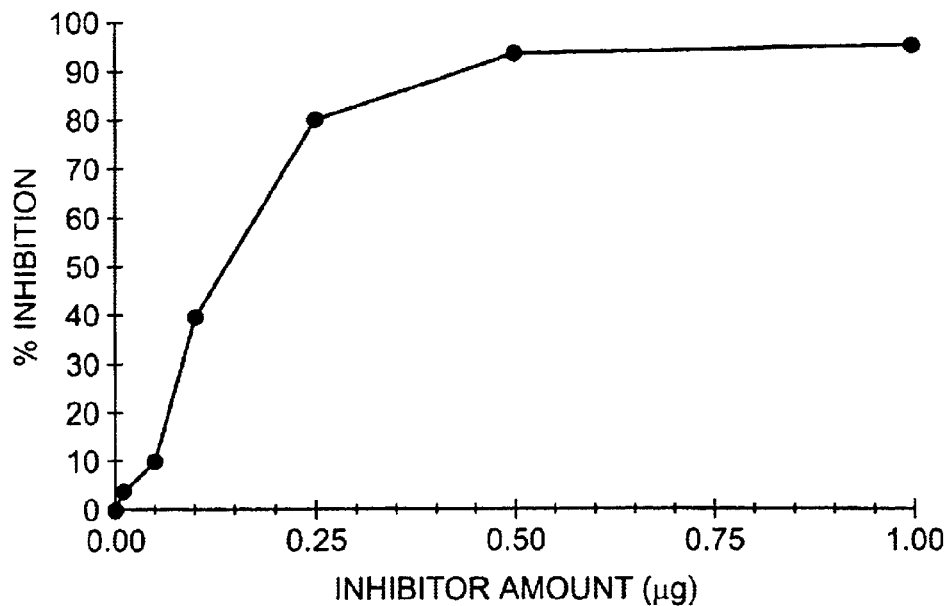
FIGS. 15A and 15B show that recombinant human metalloproteinase inhibitor from Chinese hamster ovary (CHO) cells inhibits the degradation of type I collagen and type IV collagen by metalloproteinases secreted by metastatic cells.
Figure 15B:
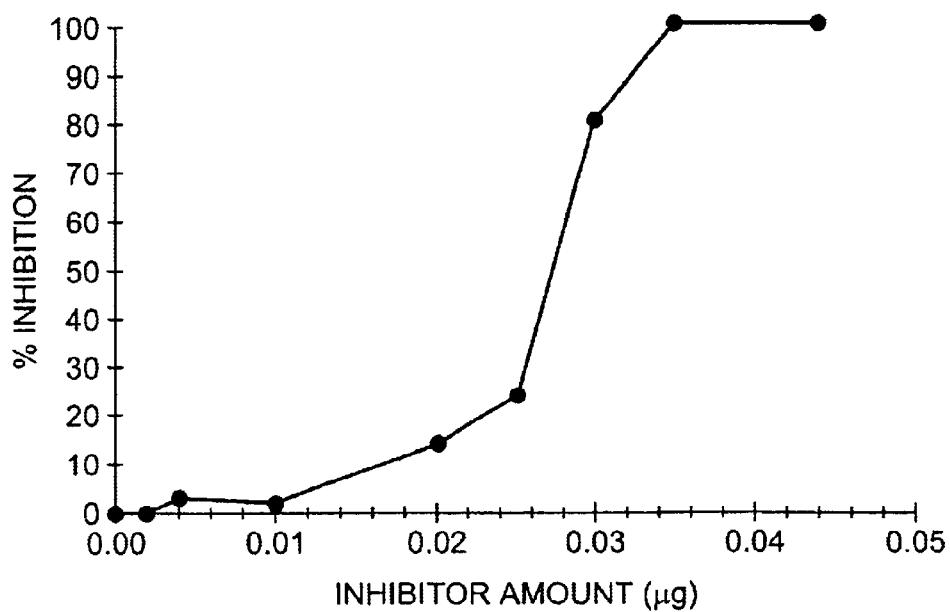

Serum-free conditioned medium from c-Ha-ras transfected rat embryo cells (4R), which are highly metastatic [Pozzatti et al., Science 243, 947–950 (1986)], was used as a source of metalloproteinases. The experiments in FIG. 15 show that recombinant human MI from CHO cells completely inhibits the degradation of type I and type IV collagen by metalloproteinases secreted by 4R cells. The legend to FIG. 15 is as follows. The 4R cells were grown in MEM with penicillin (100 U/ml) and streptomycin (100 μg/ml). The medium was harvested after 24 h of incubation, concentrated 100-fold using an Amicon stirred cell with YM10 membrane, and treated with APMA (1 mM, 37° C., 30 min) to activate metalloproteinases. Aliquots of the activated medium were then added to microtiter wells coated with $^{14}$C-labeled rat skin type I collagen [6,000 cpm/well (specific radioactivity 300 cpm/μg); 50 μl of medium added per well; FIG. 15A] or $^{14}$C-labeled type IV collagen [2,100 cpm/well (specific radioactivity 30,000 cpm/μg); 100 μl of medium added per well; FIG. 15B] in the presence of increasing amounts of the recombinant human MI. Incubations were done at 37° C. for 3 h (type I collagen) or 16 h (type IV collagen) in a total volume of 200 μl including 50 mM Tris-HCl, 200 mM NaCl, 10 mM CaCl$_2$, pH 7.5 and 10 mM N-ethylmaleimide plus 2 mM PMSF. Radioactivity released to the supernatants was determined, and results are expressed as percentages of the radioactivity released in the absence of inhibitor (% inhibition).

3. *E. coli*-derived recombinant human MI (Table 9) and CHO cell-derived recombinant human MI (Table 10) both inhibited the degradation of type I collagen which occurs in the presence of tumor cells. The tumor cells used were c-Ha-ras transfected rat embryo fibroblasts (4R cells), since they secrete large amounts of metalloproteinases and actively degrade collagen and connective tissue (Alvarez et al., J. National Cancer Inst., in press, 1990).

TABLE 9

Effect of *E. coil*-derived recombinant human MI on the degradation of type I collagen by 4R cells

| Inhibitor concentration (μg/ml) | $^{14}$C-labeled type I collagen degraded (μg/24 h) | Inhibition (%) |
| --- | --- | --- |
| 0 | 26.4 ± 0.8 | 0 |
| 0.5 | 27.9 ± 1.9 | 0 |
| 5.0 | 21.5 ± 2.8 | 19 |
| 25.0 | 12.3 ± 3.1 | 53 |
| 50.0 | 12.5 ± 5.2 | 53 |

Tumor cells were plated at $10^5$ per microtiter well on $^{14}$C-labeled rat skin type I collagen (15,000 cpm/well; specific radioactivity 300 cpm/μg) in the presence of 200 μl of Eagle minimal essential medium supplemented with 10% (v/v) FBS (acid-treated to inactivate serum proteinase inhibitors), penicillin (100 U/ml), and streptomycin (100 μg/ml).
After 24 h at 37° C., the degradation of type I collagen was determined by measuring the radioactivity released to the supernatant. The μg/24 h values represent the mean ± standard deviation for triplicate wells.

TABLE 10

Effect of CHO cell-derived recombinant human MI on the degradation of type I collagen by 4R cells

| Inhibitor concentration (μg/ml) | $^{14}$C-labeled type I collagen degraded (μg/24 h) | Inhibition (%) |
| --- | --- | --- |
| 0 | 26.4 ± 0.8 | 0 |
| 0.5 | 28.5 ± 1.8 | 15 |
| 5.0 | 12.9 ± 1.1 | 51 |
| 25.0 | 4.3 ± 1.6 | 84 |
| 50.0 | 1.9 ± 1.7 | 93 |

Experimental details as for Table 9.

Figure 16:
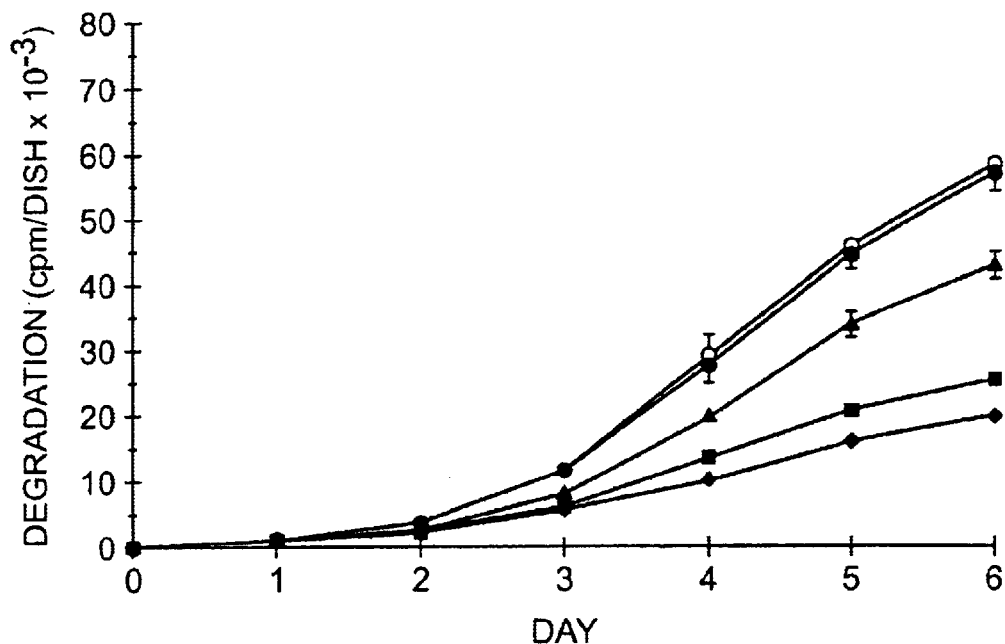
FIG. 16 shows the effect of recombinant human metalloproteinase inhibitor from *E. coli* on the degradation of connective tissue matrices deposited by smooth muscle cells which occurs in the presence of tumor cells.
Figure 17:
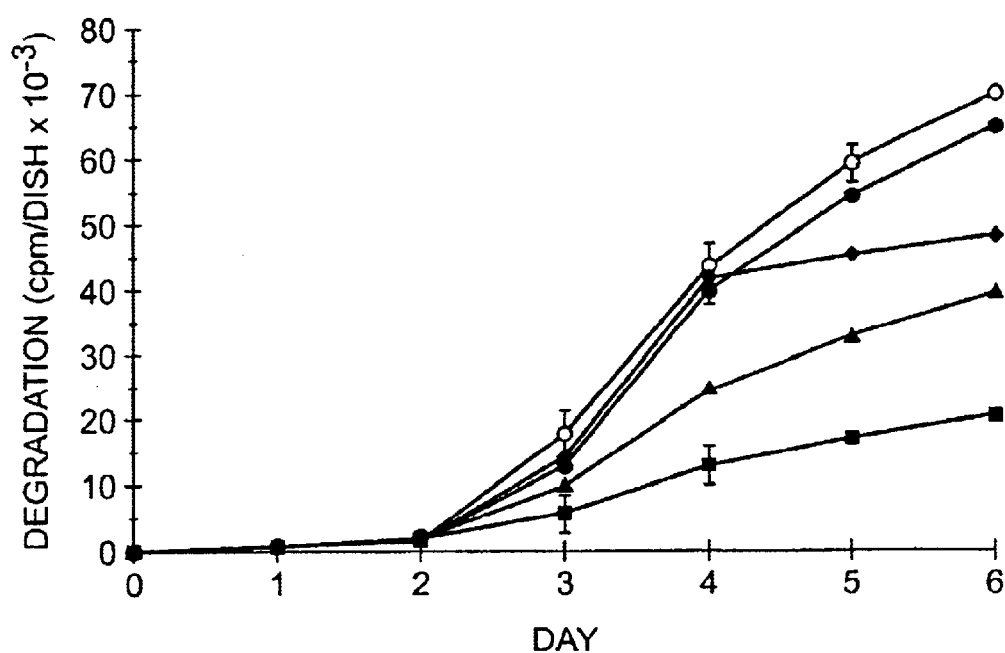
FIG. 17 shows the effect of recombinant human metalloproteinase inhibitor from Chinese hamster ovary (CHO) cells on the degradation of connective tissue matrices deposited by smooth muscle cells which occurs in the presence of tumor cells.

4. *E. coli*-derived Recombinant Human MI (Table 11; FIG. 16) and CHO cell-derived recombinant human MI (Table 12; FIG. 17) both inhibited the degradation of connective tissue matrices deposited by rat smooth muscle cells which occurs in the presence of tumor cells. The 4R cells were again used.

The matrices contain glycoprotein and types I and III collagens in a highly cross-linked and native form [Jones and De Clerck, Cancer Res. 40, 3220–3227 (1980)].

TABLE 11

Effect of *E. coli*-derived recombinant human MI on the degradation of connective tissue matrices by 4R cells

| Inhibitor concentration (μg/ml) | Matrix degradation | | Inhibition (%) |
| --- | --- | --- | --- |
| | cpm/dish | % of total matrix | |
| 0 | 57,590 | 35.9 | 0 |
| 0.1 | 56,540 | 33.2 | 1.8 |
| 1.0 | 42,550 | 25.5 | 26.2 |
| 10.0 | 25,320 | 14.1 | 56.1 |
| 25.0 | 19,740 | 11.2 | 65.8 |

TABLE 11-continued

Effect of *E. coli*-derived recombinant human MI on the degradation of connective tissue matrices by 4R cells

[$^3$H]Proline-labeled matrices produced by rat smooth muscle cells in culture were prepared as described (Jones and De Clerck, Cancer Res., supra). They contained 15% of [$^3$H]proline in the form of glycoproteins and 85% in the form of type I and type III collagens. 4R cells were plated on the matrices at 2 × $10^5$ cells/35 mm dish with 2 ml of the medium described in Table 9. Medium was changed daily with the indicated concentrations of MIalso included daily with the fresh medium. Degradation of matrices was determined by measuring radioactivity released to the supernatants. The cpm/dish results represent the means of cumulative [$^3$H] proline release (above release for background cases with no cells) after 6 days for quadruplicate dishes.

FIG. 16 shows the cumulative degradation on a daily basis for the experiment described in Table 11. In FIG. 16, the symbols correspond to MI concentrations used, as follows: open circles, 0 μg/ml; closed circles, 0.1 μg/ml; triangles, 1 μg/ml; boxes, 10 μg/ml; diamonds, 25 μg/ml.

TABLE 12

Effect of CHO cell-derived recombinant human MI on the degradation of connective tissue matrices by 4R cells

| Inhibitor concentration (μg/ml) | Matrix degradation | | Inhibition (%) | Cell Number at day 6 (×$10^{-6}$/dish) |
| --- | --- | --- | --- | --- |
| | cpm/dish | % of total matrix | | |
| 0 | 69,330 | 62 | 0 | 4.12 ± 0.18 |
| 0.05 | 64,220 | 57 | 8 | 4.50 ± 0.07 |
| 0.5 | 39,154 | 35 | 44 | 4.36 ± 0.21 |
| 5.0 | 20,314 | 18 | 71 | 4.56 ± 0.07 |
| 5.0 added only on days 4, 5 | 47,920 | 43 | 31 | 4.57 ± 0.07 |

Experimental details as for Table 11. In this experiment, it was demonstrated that the presence of inhibitor had no effect on the growth of cells, as judged by counting the number of cells present after trypsinization at day 6 (see column titled 'cell number at day 6').

FIG. 17 shows the cumulative degradation on a daily basis for the experiment described in Table 12. In FIG. 17, the symbols correspond to MI concentrations used, as follows: open circles, 0 μg/ml; closed circles, 0.1 μg/ml; diamonds, 1.0 μg/ml; triangles, 10 μg/ml; boxes, 10 μg/ml (but added only on days 4 and 5).

5. Effects of Recombinant Human MI on Tumor Cell Growth and Attachment.

Figure 18A:
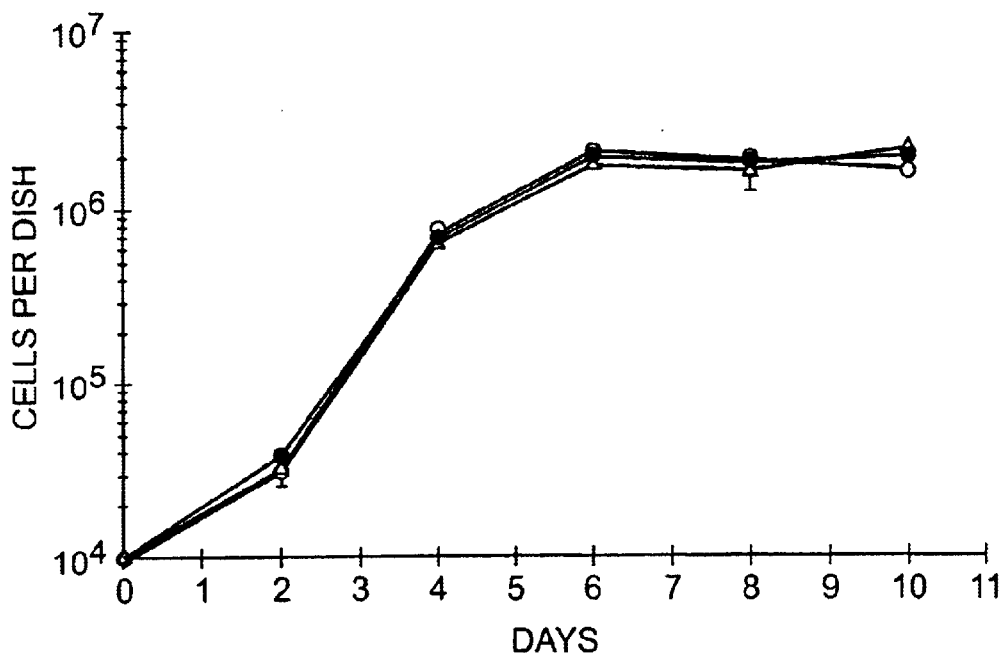
FIGS. 18A and 18B show the effects of recombinant human metalloproteinase inhibitor on tumor cell growth and attachment.

An effect of MI on tumor cell growth or attachment as an explanation of the results in sections 3 and 4 above is further ruled out by the following experiments. 4R cells were plated at $10^4$ cells per 35 mm dish in 2 ml of MEM supplemented with 10% (v/v) FBS. *E. coli*-derived recombinant human MI was added daily to the culture. Cell numbers were measured by trypsinzation and counting with a Coulter counter. Results are shown in FIG. 18A, where 'cells per dish' values represent the means±standard deviations for duplicate dishes and the symbols represent different MI concentrations used (open circles, 0 μg/ml; closed circles, 1 μg/ml, open triangles, 10 μg/ml). The MI clearly had no effect on the growth of the tumor cells.

Figure 18B:
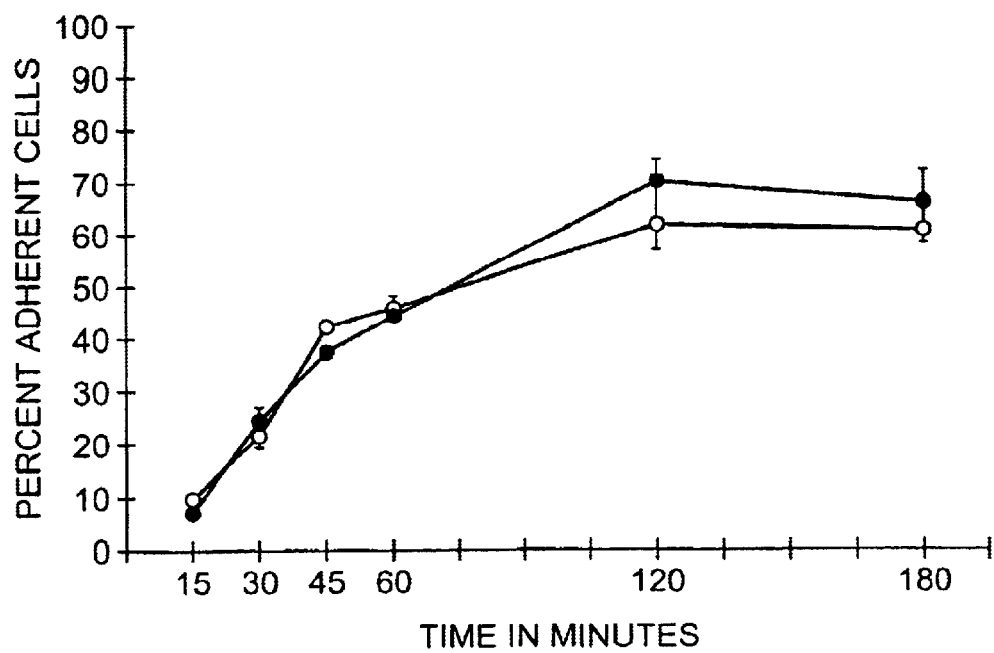

It was also demonstrated that CHO cell-derived human recombinant MI does not inhibit the attachment of 4R cells to a reconstituted basement membrane preparation [Matrigel™ (Collaborative Research, Bedford, Mass.)]. Microtiter wells were coated with 50 μg Matrigel and 50,000 cells per well were added in 200 µl MEM supplemented with 0.1% (w/v) BSA, penicillin (100 U/ml), and streptomycin (100 µg/ml). At the times indicated (FIG. 18B), non-adherent cells were removed by gentle pipetting/washing using PBS and counted. The remaining adherent cells were removed by trypsinization and counted. 'Percent adherent cells' (FIG. 18) values represent the percentage of total cells which were adherent and are the means±standard deviations for triplicate wells. The symbols represent the absence of MI (open circles) and the presence of MI at 10 µg/ml (closed circles).

6. Inhibition of the Invasion by Tumor Cells of a Smooth Muscle Cell Layer.

Figure 19A:
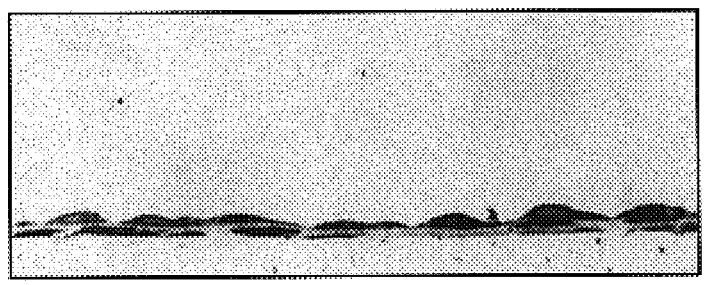
FIGS. 19A, B, and C show the effect of recombinant human metalloproteinase inhibitor on the invasion by tumor cells of a smooth muscle cell layer.
Figure 19B:
Figure 19C:
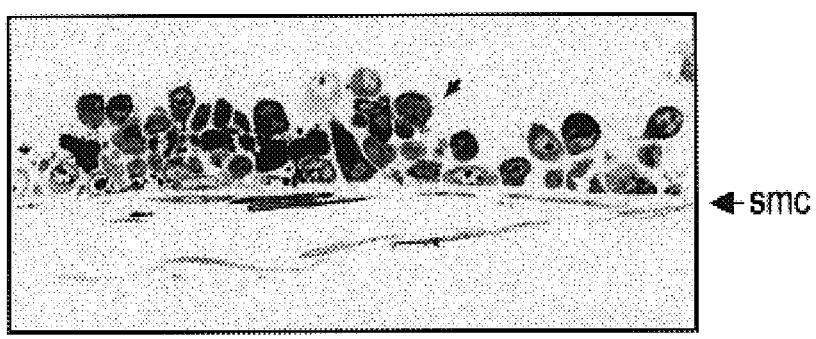

For this work, methods described by Jones et al. [Cancer Res. 41, 4613–4620 (1981)] were followed. Rat smooth muscle cells (R22 clone F) were plated at $2 \times 10^5$ cells per 35 mm dish (2 ml medium) and grown for two weeks with daily additions of ascorbic acid (50 µg/ml). 4R cells were then added ($2 \times 10^5$ cells per dish) and cocultured with the smooth muscle cells in the presence of MEM supplemented with 10% (w/v) FBS (acid-treated). After 21 days of coculture, the cultures were washed with 0.15 M NaCl and fixed in situ with 2% (w/v) glutaraldehyde in 0.1 M phosphate buffer, pH 7.3. The fixed cultures were then dehydrated by a graded series of ethanol washes and embedded in Epon:Araldite (50:50). Thick sections were cut at right angles to the surface, stained with toluidine blue, and examined by light microscopy. Results are illustrated in FIG. 19, where A represents smooth muscle cells above, B represents smooth muscle cells plus 4R cells, and C is similar to B except that CHO cell-derived recombinant human MI was added every 2 days at a concentration of 10 µg/ml. Note in B that tumor cells (arrows) are present on both sides of the smooth muscle cell layer, while in C they are present only on top of the smooth muscle cell layer. Thus the MI inhibits invasion of the smooth muscle cell layer by the tumor cells.

From the data of sections 1–6 of this Example, and from the SDS-PAGE with immunoblot analyses done on bovine MI, yeast-expressed recombinant human MI, and CHO cell-expressed recombinant human MI using polyclonal antibody against E. coli-produced human MI (see Examples 6, 8 and 9), it is definitively proved that the isolated/cloned bovine and human genes described in Example 3 do in fact represent genes for MI.

7. Inhibition of Autoproteolytic Activation of Interstitial Procollagenase by Recombinant Human MI.

The materials and methods used in these experiments are outlined in the following paragraphs.

CHO cell-derived recombinant human MI was iodinated with $^{125}$I using the method of Hunter and Greenwood [Nature 194,95–496 (1982)]. The reaction mixture was passed through a Sephadex G-100 column to remove free label.

Rabbit fibroblast interstitial procollagenase was purified from serum-free conditioned medium obtained from TPA-treated rabbit synovial cells [Aggeler et al., J. Cell. Biol. 98,1662–1671 (1984)], using the procedure of Birkedal-Hansen [Methods Enzymol. 144,140–171 (1987)]. The final preparation consisted mainly of the 52 kDa proenzyme and of a small amount (less than 10% of the amount of procollagenase) of the 42 kDa activated enzyme. When examined by a gelatin-containing SDS-polyacrylamide gel electrophoresis procedure designed to test for the presence of MI (Example 1, Section 4), the preparation was found to be essentially inhibitor-free. The preparation had a collagenase concentration of 0.42 mg/ml as determined by quantitative amino acid composition analysis and by calorimetric assay using the method of Bradford [Anal. Biochem. 72,248–254 (1976)] with bovine serum albumin as standard. The concentration value incorporates an adjustment for purity made on the basis of densitometric scanning of Coomassie blue-stained SDS-polyacrylamide gels run on aliquots of the preparation.

Activation of procollagenase was accomplished by treatment with either organomercurial or plasmin. Activation with organomercurial was performed by incubation with freshly prepared APMA (final concentration 5 mM) at 37° C. for 30 min. Activation with plasmin was performed by incubating 0.8 µg of procollagenase with 0.6 µg of plasmin (American Diagnostic Inc., New York) for 30 min at 4 or 37° C. The reaction was then blocked by the addition of a 5-fold excess (3 µg) of soybean trypsin inhibitor.

Inhibition of collagenase activity was determined by the film assay described in Example 1, section 2.

SDS-polyacrylamide gel electrophoresis was carried out by the method of Laemmli [Nature 227,680–685 (1970)] using separating gels of 12.5% (w/v) acrylamide or gradient gels (5–15%, w/v, acrylamide). The gels contained 0.1% (w/v) SDS. Sample preparation included dithiothreitol (50 mM) or 2-mercaptoethanol (0.7 M) for reduced cases and no thiol for nonreduced cases. Samples were either boiled 5 min or heated at 68° C. for 10 min as indicated. After electrophoresis, gels were silver-stained (Morrissey, Anal. Biochem., 1981, supra) stained with Coomassie blue, subjected to autoradiography after soaking in Autofluor (National Diagnostics), or immunoblotted. Immunoblotting was performed by the method of Burnette (Anal. Biochem., 1981, supra), using a rabbit polyclonal antibody raised against E. coli-derived recombinant human MI [Boone, et al. Proc. Natl. Acad. Sci. USA 87,2800–2804 (1990); Examples 4 and 5; antibody dilution 1:200]. Immunocomplexes were visualized with a goat anti-rabbit IgG serum conjugated with horseradish peroxidase (Bio-Rad). Molecular masses were estimated from plots of log $M_r$ versus mobility for the reduced molecular mass markers used.

Figure 20:
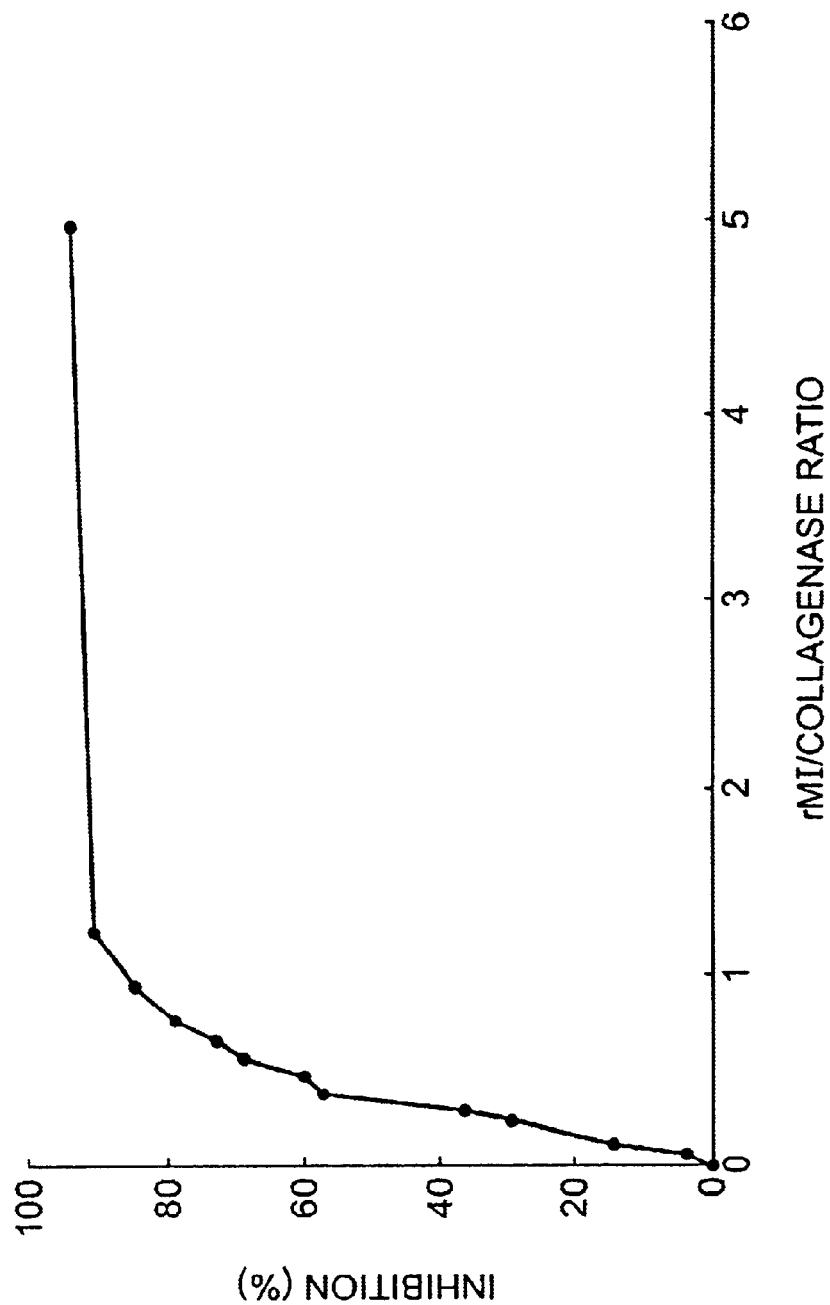
FIG. 20 shows inhibition of fibroblast interstitial collagenase by CHO-derived recombinant human MI.

Experiments carried out, and conclusions reached, are outlined in the following paragraphs. Inhibition (by increasing amounts of MI) of the degradation of $^{14}$C-labeled type I collagen by interstitial collagenase is shown in FIG. 20. APMA-activated fibroblast interstitial collagenase (0.42 µg=8 pmol) was incubated with increasing amounts of CHO cell-derived recombinant human MI in final volumes of 200 µl of 50 mM Tris-HCl, 10 mM CaCl$_2$, 20 mM NaCl, pH 7.5, for 15 min at 22° C. The samples were then placed into $^{14}$C-labeled type I collagen-coated wells of a 96-well microtiter plate for 3 h at 37° C. The collagenase activity was calculated from the amount of radioactivity released into the supernatant. Percent inhibition was calculated relative to the activity of samples that received no MI. Values are means of quadruplicate determinations. The MI/collagenase values represent molar ratios. The inhibition observed in FIG. 20 is dose-dependent with a near complete suppression of enzyme activity achieved as the molar inhibitor:enzyme ratio approaches 1. This observation is consistent with a stoichiometric inhibition and the formation of a 1:1 molar complex between the enzyme and the inhibitor.

Figure 21:
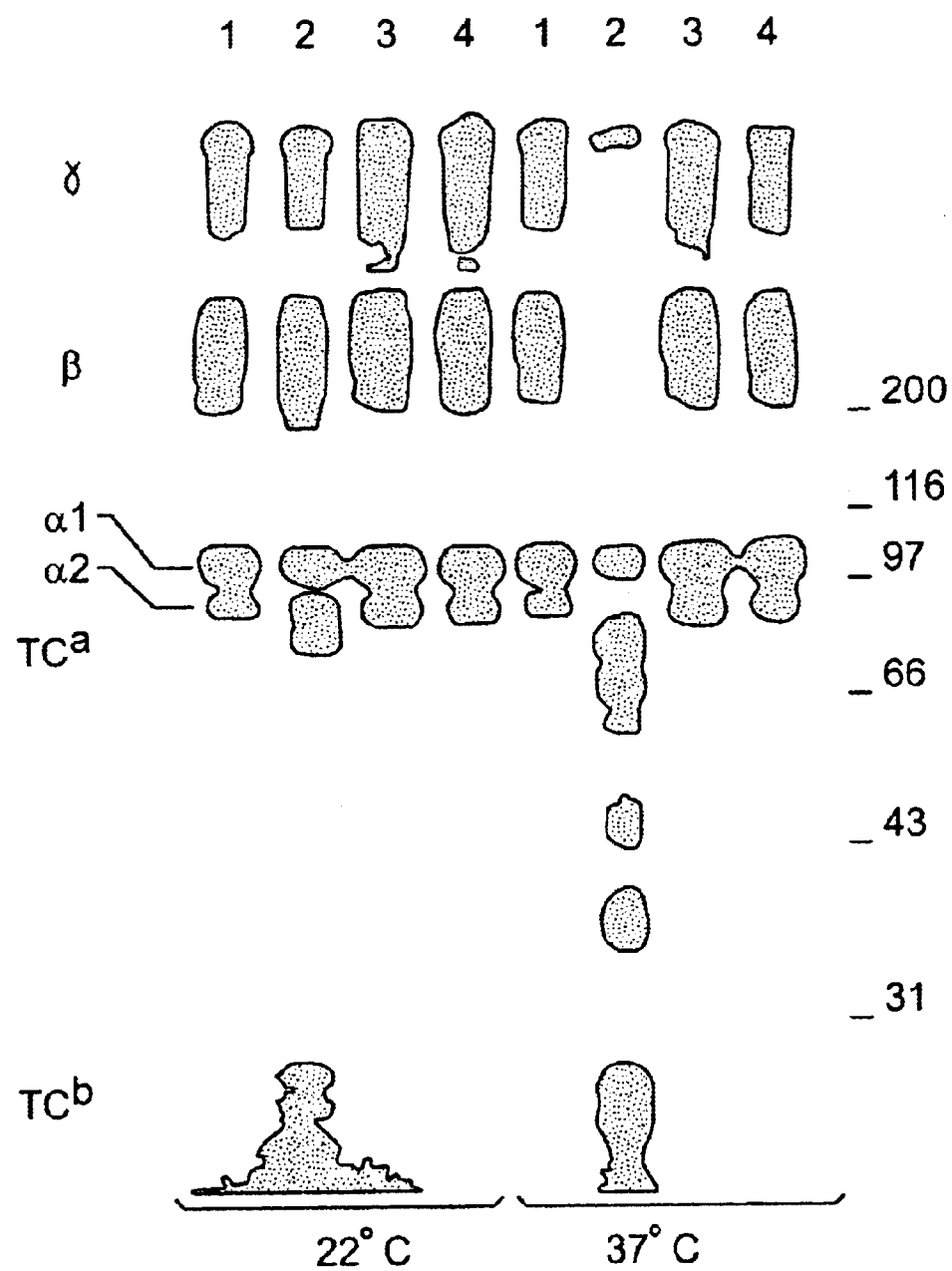
FIG. 21 shows that CHO-derived recombinant human MI inhibits the specific cleavage of type I collagen by fibroblast interstitial collagenase.

The specificity of the inhibition of type I collagen degradation by fibroblast collagenase in the presence of recombinant human MI was verified by SDS-polyacrylamide gel electrophoresis of the collagen degradation products as shown in FIG. 21. For this experiment, $^{14}$C-labeled type I rat skin collagen (10,000 cpm) was incubated for 5 h at either 22° C. or 37° C. with APMA-activated fibroblast interstitial collagenase (0.11 µg=2.1 pmol) plus various other additions, in a total volume of 100 μl of 50 mM Tris-HCl, 10 mM CaCl$_2$, 200 mM NaCl, 10 mM N-ethylmaleimide, pH 7.5. After incubation, the reactions were terminated by addition of EDTA to 20 mM. Samples were frozen, lyophilized and run (unreduced) on a 5–15% (w/v) acrylamide gradient SDS gel. After electrophoresis, the gel was soaked in Autofluor, dried, and subjected to autoradiography for 48 hours at −80° C. Lanes 1: $^{14}$C-labeled type I collagen; lanes 2: as lanes 1 plus APMA-activated fibroblast interstitial collagenase; lanes 3: as lanes 2, plus MI (0.1 μg=4.6 pmol) added prior to incubation; lanes 4: as lanes 2 plus EDTA (20 mM) added prior to incubation. $α_1$ and $α_2$ indicate positions of the $α_1(I)$ and $α_2(I)$ collagen chains. β and γ indicate the position of the dimeric and trimeric molecules respectively. $TC^a$ and $TC^b$ indicate positions of the three-quarter length and one-quarter length collagen chain fragments, respectively. Migration positions of reduced molecular weight markers are indicated on the right; values represent molecular mass in kDa. Interstitial collagenase typically generates the ¾ and ¼ length fragments ($TC^a$ and $TC^b$) of collagen (FIG. 21, Lane 2). These were not seen when MI or EDTA was added to the incubation mixtures (FIG. 21, lanes 3 and 4, respectively). At 37° C., further degradation of the collagen chains was observed, possibly due to minor contamination of the preparation with gelatinase. The initial cleavage of the collagen as well as its further degradation were completely blocked by recombinant human MI.

Figure 22:
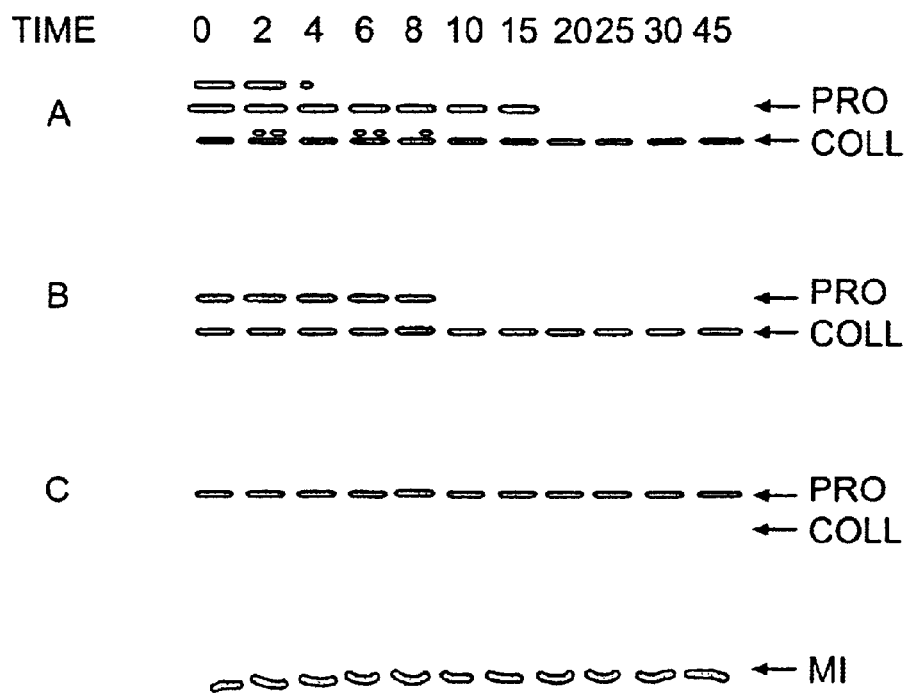
FIGS. 22A, B, and C show that CHO-derived recombinant human MI inhibits APMA-induced activation of fibroblast interstitial procollagenase.

Next to be investigated was whether MI could interfere with the activation of procollagenase initiated by organomercurials. This activation is autocatalytic. For the experiment of FIG. 22, interstitial fibroblast procollagenase (0.84 μg=16 pmol) in 5 μl of 50 mM Tris-HCl, 200 mM NaCl, 10 mM CaCl$_2$, pH 7.5 was incubated at 37° C. in the presence of APMA (5 mM). At the indicated times, the reactions were terminated by addition of EDTA to 20 mM. Samples were then heated at 68° C. for 10 min, in the presence of 50 mM dithiothreitol and run on 12.5% (w/v) SDS-polyacrylamide gels. Gels were stained with Coomassie blue. Gel A, fibroblast interstitial procollagenase activated with APMA; gel B, same as A, but trypsin activated fibroblast interstitial collagenase (0.84 μg) was added prior to APMA addition; gel C, same as A, but MI (0.57 μg=27 pmol) was added prior to APMA addition. The time at which the reaction was terminated with EDTA is indicated across the top of the figure (in minutes). The arrows at the right indicate migration positions of procollagenase (PRO), collagenase (COLL) and MI. Treatment of procollagenase with APMA resulted in the conversion of the 52 kDa proenzyme to the 42-kDa activated enzyme, as visualized by the SDS-polyacrylamide gel electrophoresis in FIG. 22. This conversion was completed over 30 minutes (FIG. 22A). Its rate was unaffected by the addition of trypsin-activated collagenase (FIG. 22B). This observation is consistent with the initiation by organomercurials of an intramolecular autoproteolytic process rather than an intermolecular process that would have been accelerated by the addition of activated collagenase [Grant et al., J. Biol. Chem. 262,5886–5889 (1987)]. In the presence of MI at a molar inhibitor:enzyme ratio of 1.7:1 conversion of the 52-kDa procollagenase to the 42-kDa enzyme was completely inhibited (FIG. 22C). These experiments show that MI blocks the autocatalytic activation of procollagenase initiated by organomercurials.

Figure 23:
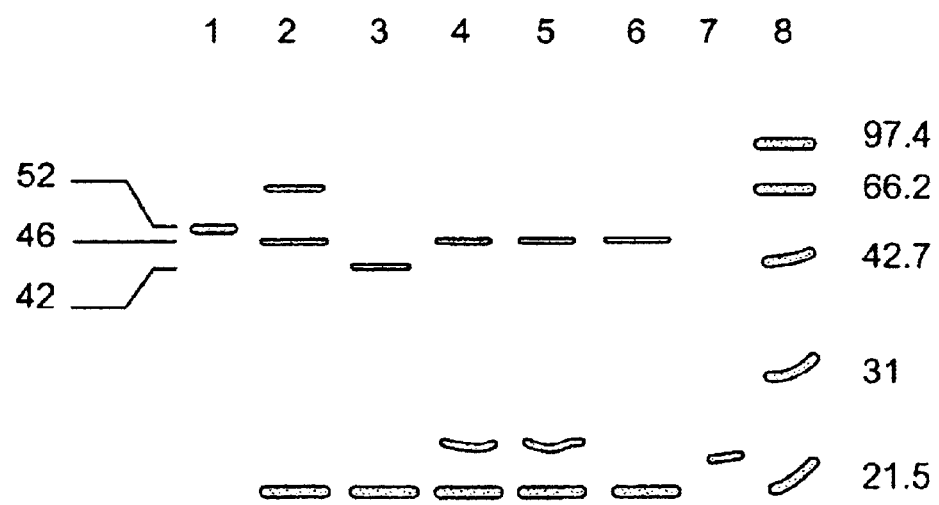
FIG. 23 shows that CHO-derived recombinant human MI inhibits plasmin-induced activation of fibroblast interstitial procollagenase.

Autocatalytic activation of procollagenase can also be initiated by plasmin. Inhibition of this process by recombinant human MI was examined in the experiment of FIG. 23. Interstitial fibroblast procollagenase (0.84 μg=16 pmol) in 5 μl of 50 mM Tris-HCl, 200 mM NaCl, 10 mM CaCl$_2$, pH 7.5 was incubated alone or with the additions indicated below. After incubation, samples were reduced in the presence of 50 mM dithiothreitol, heated at 68° C. for 10 min and subjected to SDS-polyacrylamide gel electrophoresis. Lane 1, procollagenase; lane 2, procollagenase incubated with plasmin (0.6 μg) at 4° C. for 30 minutes followed by addition of soybean trypsin inhibitor (3 μg) to inactivate plasmin; note the presence of plasmin (70-kDa band) and soybean trypsin inhibitor (21.5-kDa band) on the gel; lane 3, same as lane 2 but sample was further incubated at 37° C. for 30 minutes after addition of soybean trypsin inhibitor; note the conversion of the 46-kDa intermediate to 42-kDa activated collagenase; lane 4, same as lane 2, but MI (0.57 μg=27 pmol) was added along with the plasmin; note the presence of 25-kDa MI (reduced); lane 5, same as lane 3, but MI was added prior to incubation at 37° C.; lane 6, same as lane 3, but EDTA was added to 20 mM prior to incubation at 37° C.; lane 7, MI (27 pmol) alone; lane 8, reduced molecular weight markers with molecular mass values indicated on the right (in kDA). Positions of the 52-kDa procollagenase, 46-kDa intermediate and 42-kDa activated collagenase are indicated on the left. It can be seen that in the presence of plasmin at 4° C., procollagenase was converted from the 52-kDa proenzyme to a 46-kDa intermediate clearly identified on SDS-polyacrylamide gels in FIG. 23 (lane 2). Activation of this intermediate by the autocatalytic reaction was then initiated by incubating the sample at 37° C. (Grant et al., J. Biol. Chem., 1987, supra) (lane 3). The addition of MI had no effect on the conversion of the 52-kDa proenzyme to the 46-kDa intermediate (lane 4), as expected since MI has no antiplasmin activity (Example 1, section 4). In contrast, the conversion of the 46-kDa intermediate to the 42-kDa active enzyme which should have occurred at 37° C. was completely blocked by MI and also by EDTA (lanes 5 and 6, respectively). This experiment further indicates that the inhibitory activity of MI toward the activation of procollagenase is mediated by inhibition of the intra-molecular autoproteolysis.

Figure 24A:
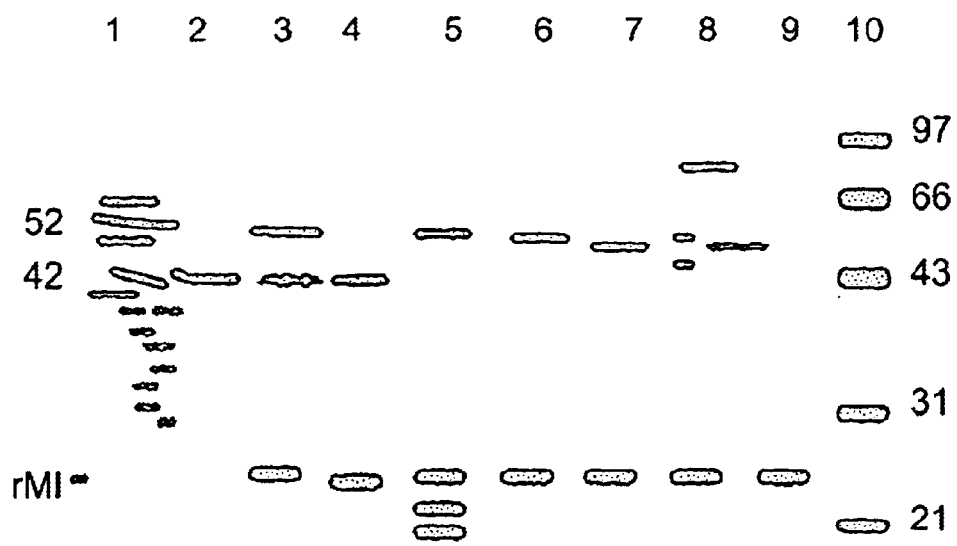
FIGS. 24A & 24B shows that CHO-derived recombinant human MI forms complexes with procollagenase and collagenase that are stable to SDS.
Figure 24B:
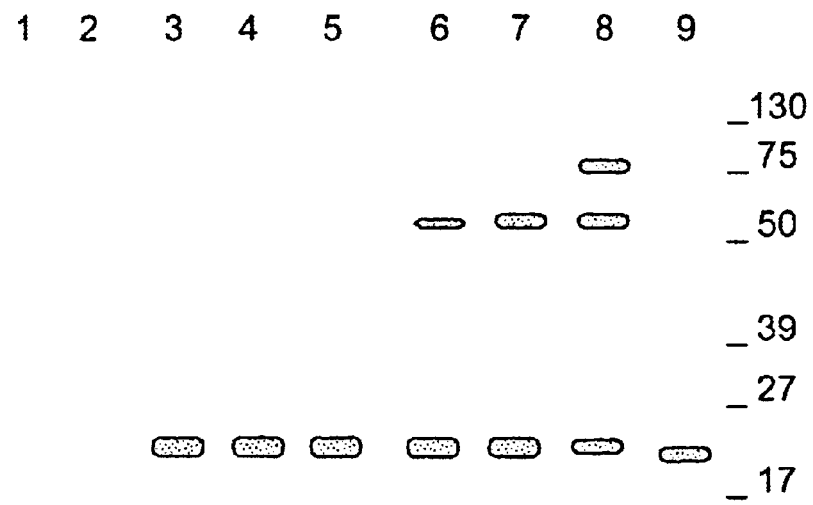
Figure 25:
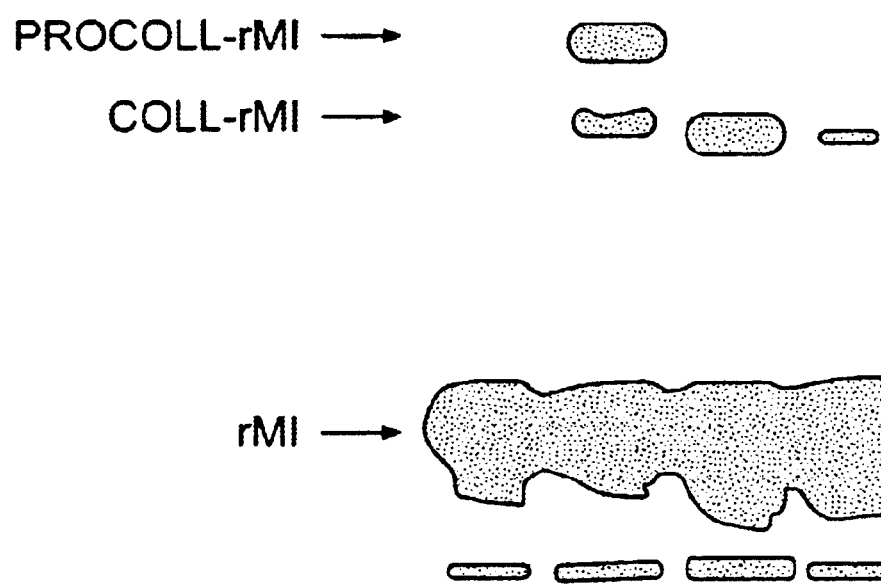
FIG. 25 shows SDS-polyacrylamide gel demonstrating the formation of SDS-stable complexes between $^{125}$I-labeled MI and procollagenase and collagenase.

Next, it was demonstrated that MI forms complexes with both procollagenase and collagenase. Such complexes could be visualized after SDS-polyacrylamide gel electrophoresis, provided that the samples were not heated prior to loading onto the gels as shown in FIG. 24. The results of FIG. 24 were obtained as follows. Fibroblast interstitial procollagenase (0.84 μg=16 pmol) in 5 μl of 50 mM Tris-HCl 200 mM NaCl, 10 mM CaCl$_2$ pH 7.5 was incubated as indicated below, in duplicate for each case. After incubations, samples were prepared for SDS-polyacrylamide gel electrophoresis as usual with dithiothreitol. Samples in lanes 3 to 5 were not heat-treated prior to electrophoresis. After electrophoresis (12.5%, w/v, acrylamide), gel A was stained with Coomassie blue and gel B was immunoblotted using a rabbit anti MI antiserum. Migration positions of reduced molecular weight markers are indicated on the right (gel A, same as in FIG. 23; gel B, prestained markers); values represent molecular mass in kDa. Lanes 1, interstitial procollagenase; lanes 2, interstitial procollagenase activated with APMA (5 mM) at 37° C. for 30 min; lanes 3, interstitial procollagenase incubated with MI (0.57 μg =27 pmol) for 15 min at 22° C.; lanes 4, as lanes 3 followed by incubation with APMA for 30 min at 37° C.; lanes 5, as lanes 2 followed by incubation with MI for 15 min at 22° C.; lanes 6, MI alone. As seen in FIG. 24A, when a procollagenase-MI mixture was treated with APMA and then subjected to electrophoresis without heat treatment, a band with apparent molecular mass of 81 kDa was observed instead of the expected 52-kDa procollagenase band (lanes 4 and 1, respectively). The presence of such a band was not detected in the absence of the APMA treatment (lane 3). Similarly, for APMA-activated collagenase incubated with MI, a band with molecular mass of 50 kDa was observed (lane 5) instead of the expected 42-kDa band (lane 2). Concomitant decreases in the amount of free MI occurred. When plasmin-treated procollagenase was incubated with MI, a 55-kDa band could be detected (not shown). The results suggest that the molecular weight shifts referred to reflect formation of SDS-stable complexes of MI with procollagenase and collagenase. The complexes are dissociated if the gel samples are heated prior to electrophoresis (not shown), and the formation of a procollagenase-MI complex seemed to require an initial conformational change of the procollagenase brought about by organomercurials (compare lanes 3 and 4). Since samples were electrophoresed after reduction with dithiothreitol, such complexes do not appear to involve intermolecular disulfide bonds. Confirmation that the bands representing putative complexes truly contain MI was obtained by immunoblot analysis using antiserum against MI (FIG. 24B) and by the use of $^{125}$I-labeled MI and autoradiography (FIG. 25). The results in FIG. 25 were obtained as follows. Interstitial procollagenase (0.84 $\mu$g=16 pmol) in 5$\mu$l of 50 mM Tris-HCl, 200 mM NaCl, 10 mM $CaCl_2$, pH 7.5 was incubated as indicated below with $^{125}$I-labeled MI (20,900 cpm; specific radioactivity 29,400 cpm/$\mu$g). Samples were treated with dithiothreital but not heat-treated before being electrophoresed on SDS-polyacrylamide gels. The gel was subjected to autoradiography after soaking in Autofluor. Lane 4, procollagenase plus $^{125}$I-labeled MI incubated for 15 min at 22° C.; lane 3, APMA activated collagenase plus $^{125}$I-labeled MI incubated for 15 min at 22° C.; lane 3, same as lane 4, followed by addition of APMA (5 mM) and incubation for 30 min at 37° C.; lane 1, $^{125}$I-labeled MI alone. The arrows at the left indicate migration positions of complex between procollagenase and MI (procoll-rMI), complex between collagenase and MI (coll-rMI), and MI alone (rMI).

EXAMPLE 12
Inhibition of Metastasis by Recombinant Human MI in an in vivo Murine Model.
1. Coinjection of Tumor Cells and Recombinant MI.

A mouse model involving metastasis to the lung after injection of B16 mouse melanoma tumor cells [Fidler, Nature 242, 148–149 (1973)] was used. The B16 cells (clone F10) were obtained from Dr. J. Fidler (Houston, Tex.) and were first grown subcutaneously in C57BL6 mice and cultured in vitro from the primary tumor nodules. Cells after a second in vitro passage were stored as frozen stocks. Cells from frozen stock were cultured for two days in MEM supplemented with sodium pyruvate (1 mM), non-essential amino acids (0.1 mM), L-glutamine (1 mM), penicillin (200 U/ml), streptomycin (200 $\mu$g/ml), MEM vitamin solution (1%, v/v), and 10% (v/v) FBS. Subconfluent cultures were briefly trypsinized (1–2 min), collected in serum-containing medium, and suspended in PBS at a final concentration of $5 \times 10^5$ cells/ml. Cell viability was 97% as determined by trypan blue exclusion.

The animals used for the model were C57BL6 J mice, obtained from Jackson Laboratories (Maine), and observed for 1 week in the animal facility prior to the start of experiments. MI-treated animals (9) were injected with CHO cell-derived recombinant human MI (prepared as described in Example 10; 4.45 mg/ml in sterile PBS) into the peritoneal cavity (0.25 ml per injection=1.1 mg per injection). Control animals were injected with 0.25 ml sterile PBS. The injections were done 13 h and 1 h prior to injection of tumor cells (7 animals) or at the time of tumor cell injection (2 animals). All animals then received additional injections of MI (treated animals) or vehicle (control animals) at 12 h intervals for a total of 4.5 days after injection of tumor cells. The B16 melanoma cells were injected into the lateral tail vein of each mouse ($1.25 \times 10^5$ cells in 0.25 ml). All injections were alternated between MI-treated and control animals. Two weeks after injection of tumor cells, animals were sacrificed by $CO_2$ euthanasia and lungs were examined for the presence of surface tumor colonies after intratracheal injection of Bouin's solution. Each lung was dissected into 5 separate lobes and colonies on each lobe were counted under a dissecting microscope. Results are given in Table 13.

TABLE 13

Formation of lung nodules after injection of B16 tumor cells into MI-treated vs. control mice

| Group | Number of animals | Number of lung nodules in each animal | Mean number of lung nodules (± standard error) |
| --- | --- | --- | --- |
| MI-treated | 9 | 1, 3, 5, 6, 6, 8, 107, 10*, 80* | 25.9 ± 4.1 |
| Control | 9 | 7, 37, 45, 67, 82, 111, 127, 132, 264 | 96.9 ± 7.9 |

*The 2 animals that were not treated with MI 13 h and 1 h prior to injection of tumor cells.

The results of Table 13 indicate a substantial and highly significant ($0.01 < p < 0.05$ by the Wilcoxon rank sum test) reduction in the appearance of lung tumor nodules as a result of the MI treatment.

2. Transfection of Tumor Cells with Gene for MI.

Figure 26:
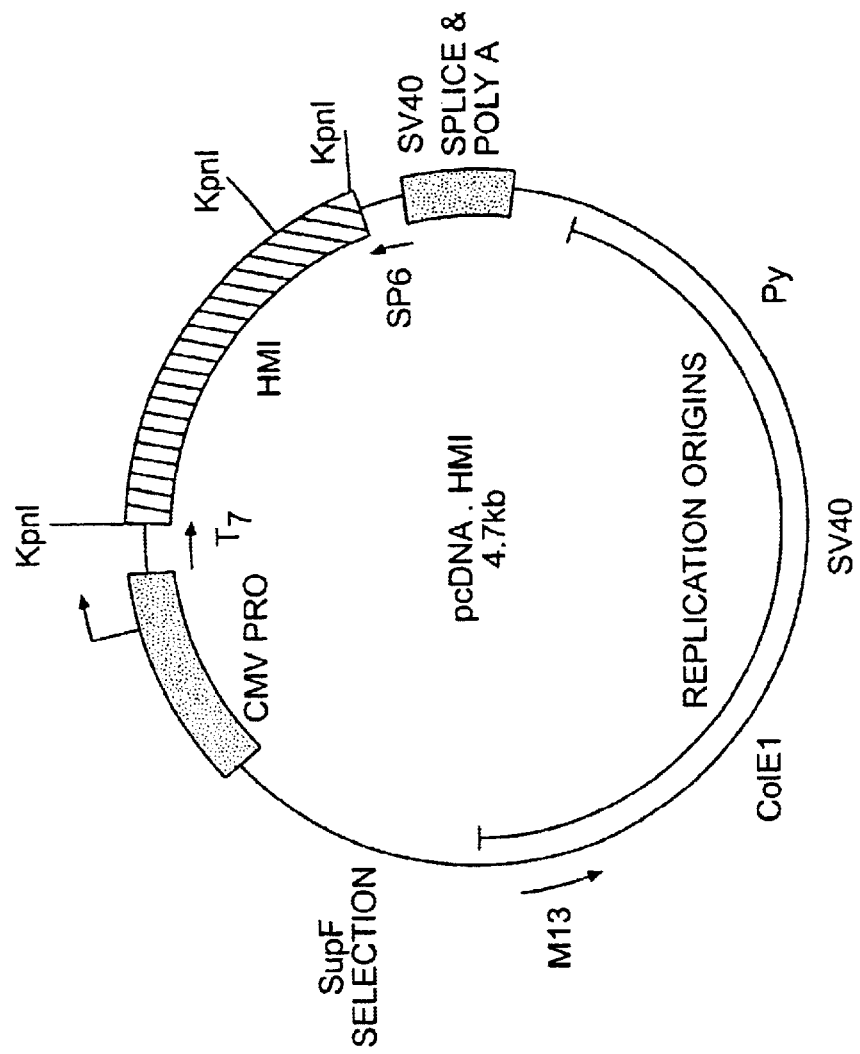
FIG. 26 shows construction of pcDNA HMI. Plasmid pcDNA HMI was made by inserting the NcoI-StuI fragment of plasmid pUC HMI into plasmid pcDNA by blunt end ligation.

First a suitable expression vector containing human MI CDNA was constructed by methods similar to those described in Example 9. Human MI cDNA was obtained from plasmid pUC HMI (Example 3) using NcoI and StuI [Boone et al., Proc. Natl. Acad. Sci. USA 81, 2800 (1990)]. This fragment extends from the first codon of the 26 amino acid leader-sequence to ten base pairs after the termination codon. Restriction site overhangs were filled in with the Klenow fragment of E. coli DNA polymerase and the fragment was inserted by blunt-end ligation into pcDNA (Invitrogen), a plasmid vector containing the CMV promoter and enhancer, splice segment and a polyadenylation signal. The resulting vector (pcDNA HMI) is shown in FIG. 26.

c-Ha-ras transfected rat embryo cells [4R cells; R. Pozzatti et al. Science 232, 223 (1986)] were used for transfection. These cells are highly invasive and metastatic in nude mice and secrete a large amount of metalloproteinases with no measurable secretion of inhibitors. It has also been shown that recombinant MI inhibits the invasion of artificial tissue substrates by these cells (Example 11, section 2).

Cells were cotransfected by calcium phosphate precipitation with the pcDNA HMI plasmid and a pY3 plasmid containing the hygromycin B phosphotransferase gene as a selectable marker. The transfection efficiency was $10^{-3}$. Fifty-two clones cotransfected with pcDNA HMI and pY3 plasmids were established in the presence of 0.4 mg/ml of hygromycin B and screened for the secretion of MI by immunodotblot analysis of aliquots of serum-free conditioned media. Twenty clones transfected with pY3 plasmid alone were established as controls and were found negative for the production of MI. Untransfected cells were also negative. Five clones transfected with pcDNA HMI and pY3 plasmids (4 positive and 1 negative) and two clones transfected with pY3 plasmid alone were then chosen for a more detailed analysis.

Figure 27A:
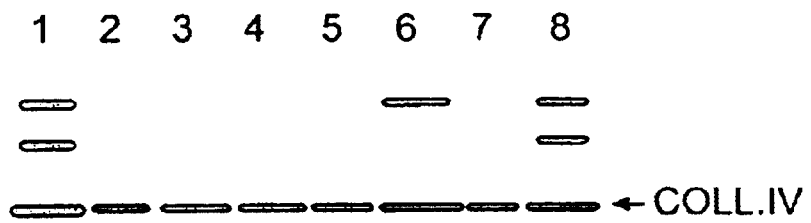
FIGS. 27A, B, and C show SDS-PAGE analysis of concentrated serum-free conditioned media.
Figure 27B:
Figure 27C:
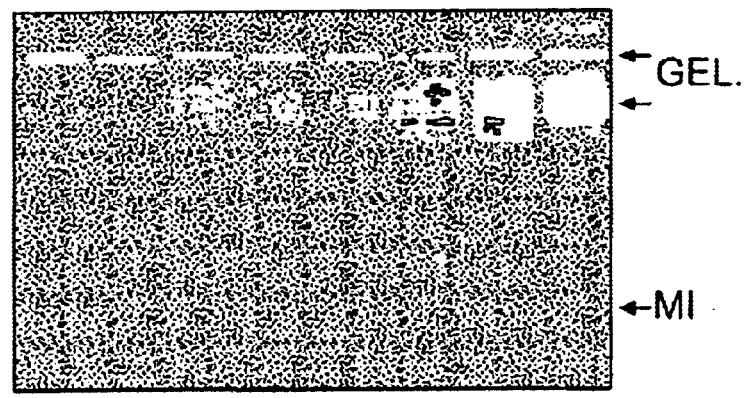

First the secretion of type IV collagenase (72-kDa gelatinase) and MI in serum-free conditioned medium of these clones was analyzed by SDS-PAGE (FIG. 27). Samples (unreduced) corresponding to $8.5 \times 10^4$ cells were electrophoresed. The gels were immunoblotted with polyclonal rabbit antiserum against human type IV collagenase (A; Coll.IV) or with antiserum against recombinant human MI (B) using the methods described in Example 1, Section 4. C shows substrate gel analysis of concentrated conditioned media. Samples (unreduced and not heated) corresponding to $4.2 \times 10^4$ cells were electrophoresed on gelatin-containing SDS-polyacrylamide gels as described in Example 1, Sections 4b and 4c. Positions of 92-kD and 72-kD gelatinases (Gel.) and MI are indicated on the right. As described in Example 1, sections 4b and 4c, the clear bands represent proteins with gelatinolytic activity and dark bands represent proteins with inhibitory activity. For all gels (A to C): lane 1, 4R parental cells; lane 2, clone 4.6; lane 3, clone 4.17; lane 4, clone 8.27; lane 5, clone 8.39; lane 6, clone 8.60; lane 7, clone 8.68, and lane 8, clone 8.71. Clones 4.6 and 4.17 were transfected with the pY3 plasmid alone. Clones 8.27, 8.39, 8.60, 8.68 and 8.71 were cotransfected with pcDNA HMI and pY3 plasmid. It is apparent in A and B that all clones including the parental cells secreted detectable amounts of type IV collagenase (FIG. 27A), but secretion of MI was only detected in the four clones transfected with pcDNA HMI (clones 8.27, 8.39, 8.60 and 8.68; FIG. 27A, lanes 4 to 7 respectively) that were originally positive by immunodotblot analysis (FIG. 27B). By the substrate gel analysis in C, the secretion of two gelatinases (92-kDa and 72-kDa gelatinases) by all clones selected and the presence of functional MI in clones 8.27, 8.39, 8.60 and 8.68 was demonstrated.

Figure 28:
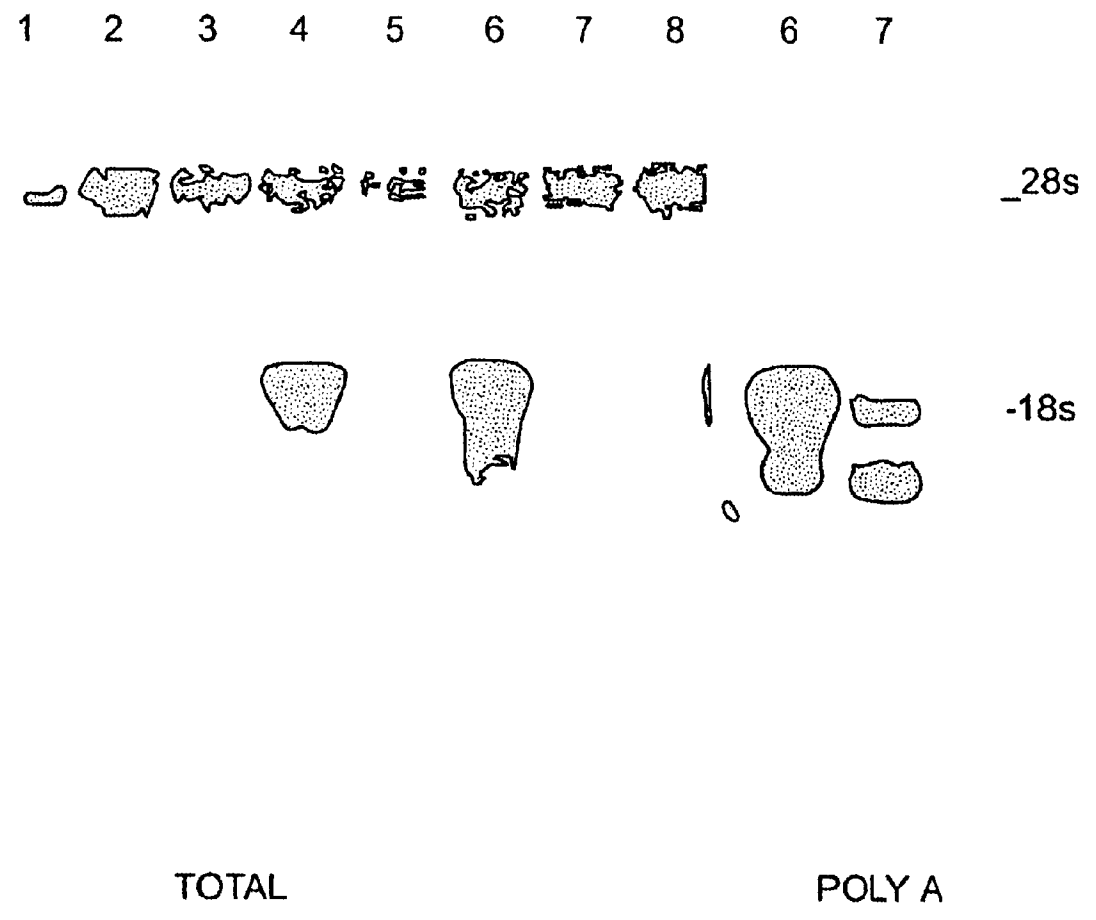

Northern blot analysis of 4R cells and 4R cells transfected with pY3 and pcDNA HMI is shown in FIG. 28 and was conducted as follows. Total cellular RNA was extracted from subconfluent cultures of cells growing in 100 mm dishes using the method of Chirgwin et al., Biochem. 18,5294–5299 (1979). Total RNA samples (20 μg) and poly A+ RNA (5 μg) were then electrophoresed on a 1% agarose gel, blotted onto a nylon membrane and hybridized with a $^{32}$P-labeled MI oligonucleotide probe which does not cross hybridize with TIMP (probe 2 in Example 3, corresponding to amino acids 148 to 164). Hybridization was carried out in 5×SSC at 42° C., and blots were washed with 3×SSC and 0.3×SSC at room temperature. Positions of ribosomal RNA markers are indicated by arrows on the right in FIG. 28. Lanes in FIG. 28 correspond to cells and clones as indicated in FIG. 27. As seen in FIG. 28, a 1.85 kb message was detected in the 4 clones that secreted MI; this message size is consistent with the position of the polyadenylation signal in the pcDNA HMI vector. A 1.3 kb message was also detected in parental cells and in all transfected clones, indicating a low level of endogenous expression of inhibitor in 4R cells. The amount of c-Ha-ras-1 transcript was detected using the HRAS Protoncogene (American Tissue Culture Collection) as probe and was generally unchanged in all clones investigated.

The effect of MI production and secretion by transfected 4R cells on proteolytic activity, growth in vitro, and tumorigenic potential in nude mice was then examined (Table 13A). As anticipated, the level of inhibitor activity detected in serum-free conditioned media inversely correlated with the level of proteolytic activity toward type I and type IV collagen. Secretion of MI had no significant effect on the cell growth (doubling time ranging between 15 h and 19 h).

The secretion of MI by one clone, 8.60, which secreted the largest amount of inhibitor, significantly affected the ability of this clone to form lung colonies after intravenous injection in athymic (nude) mice. The formation of lung nodules is a measure of metastatic potential of injected cells (see this Example, section 1). Relative to the case with untransfected cells, a 65% decrease in the number of lung nodules was seen when clone 8.60 cells were injected intravenously in the tail vein of nude mice, as shown in Table 13A. In these experiments, Swiss nu/nu mice (6–8 weeks old) were injected intravenously with $2 \times 10^4$ cells in 0.2 ml of sterile phosphate buffered saline. Cell viability as estimated by trypan blue was equal to or higher than 90%. After 14 days, animals were sacrificed and tumor nodules at the surface of lungs were counted following endotracheal injection of the lungs with India ink (15%; v/v).

Furthermore, the nodules present in mice injected with clone 8.60 cells appeared to be generally smaller in size than those seen in mice injected with parental 4R cells. This raised the question of whether the lung nodules from clone 8.60 cells were derived from cells that had lost the ability to express MI. Analyses of several nodules grown in vitro indicated that these metastatic cells contained unchanged levels of MI transcript and had retained the ability to secrete a functional inhibitor. The analyses were conducted as follows. Individual lung nodules were obtained 14 days after the intravenous injection of nude mice with clone 8.60 cells and either cultured in Eagle's MEM medium containing 10% fetal bovine serum, penicillin (200 μg/ml), streptomycin (200 μg/ml) and hygromycin B (0.4 μg/ml) or quick frozen in liquid nitrogen. Five cultured nodules were analyzed for MI RNA by Northern blotting, and for secretion of MI in the serum-free conditioned medium by immunoblotting and gelatin substrate gel analysis, all described above in this section. Total RNA from five individual frozen nodules was also extracted and analyzed for MI RNA and ras RNA by Northern blotting.

The results of these analyses are given in FIG. 29. A and B is cytoplasmic RNA (20 μg) from 4R cells, clone 8.60 cells, and from five cultured metastastic lesions (ml to m5) analyzed by Northern blotting with MI (A) and ras (B) probes. C is northern blotting of RNA from five frozen metastatic nodules (nl to n5) using MI probe. Positions of endogenous (1.3) and transfected (1.85) MI transcripts are indicated on the right (in kb). D is analysis of conditioned media from clone 8.60 cells and from cultured nodules ml to m5, by SDS-PAGE with immunoblotting using antiserum against MI. Samples of concentrated (50×) medium corresponding to $8.5 \times 10^4$ cells were analyzed; MI, 0.2 μg of recombinant MI as control; positions of prestained molecular weight standards are indicated on the right (in kD). E is gelatin substrate gel of samples described in D, corresponding to $4.2 \times 10^4$ cells; Gel refers to gelatinases (92 kD and 72 kD). The various analyses in FIG. 29 make it clear that the tumor nodules were expressing MI (both MI message and functional MI protein) at essentially the same level as parental clone 8.60. The presence of these metastatic nodules therefore did not appear to be the result of clone 8.60 variants that expressed reduced amounts of MI.

Figure 30A:
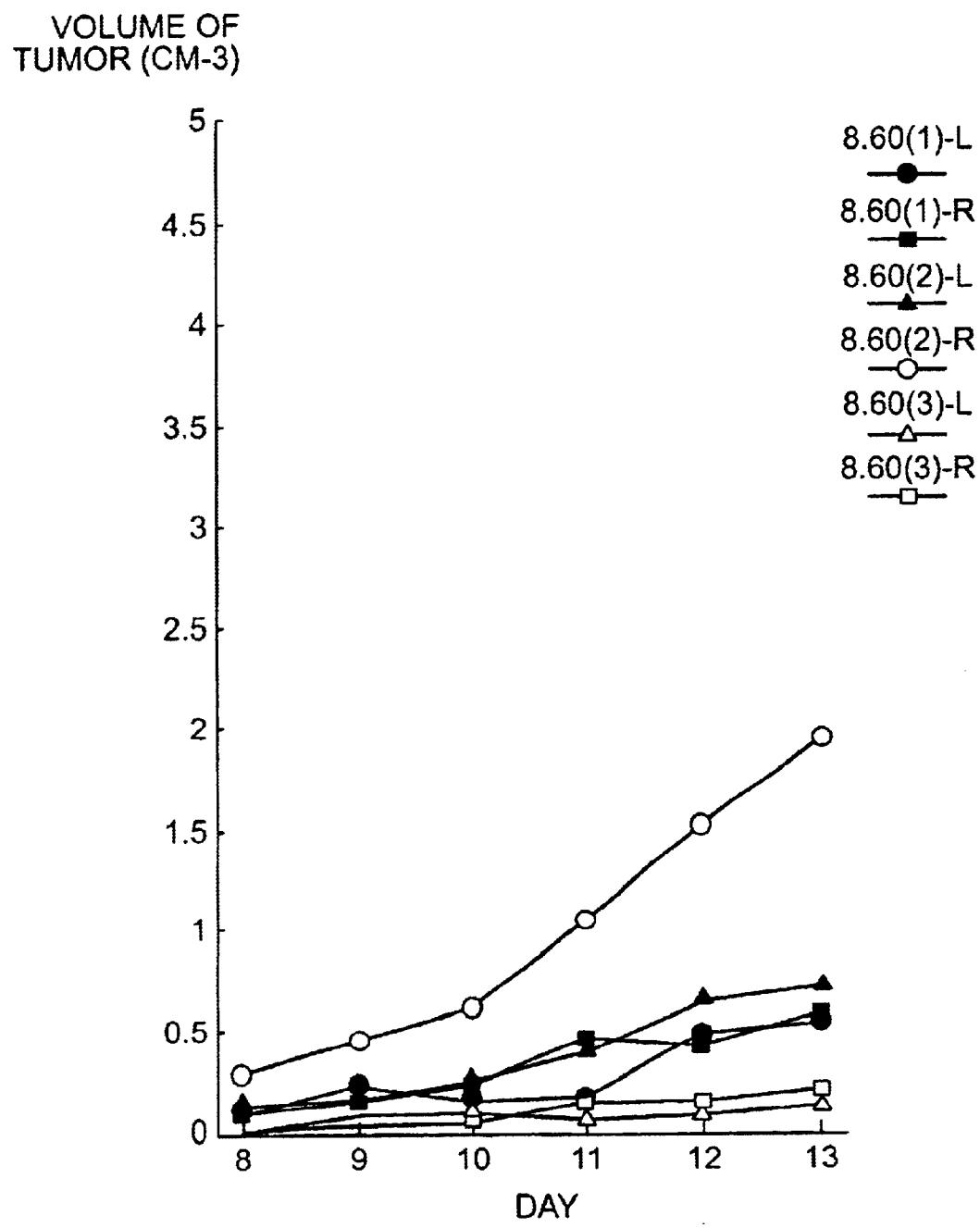
FIGS. 30A & 30B show in vivo growth of 4R tumor cells (A) and clone 8.60 (B) cells injected subcutaneously in nude mice.
Figure 30B:
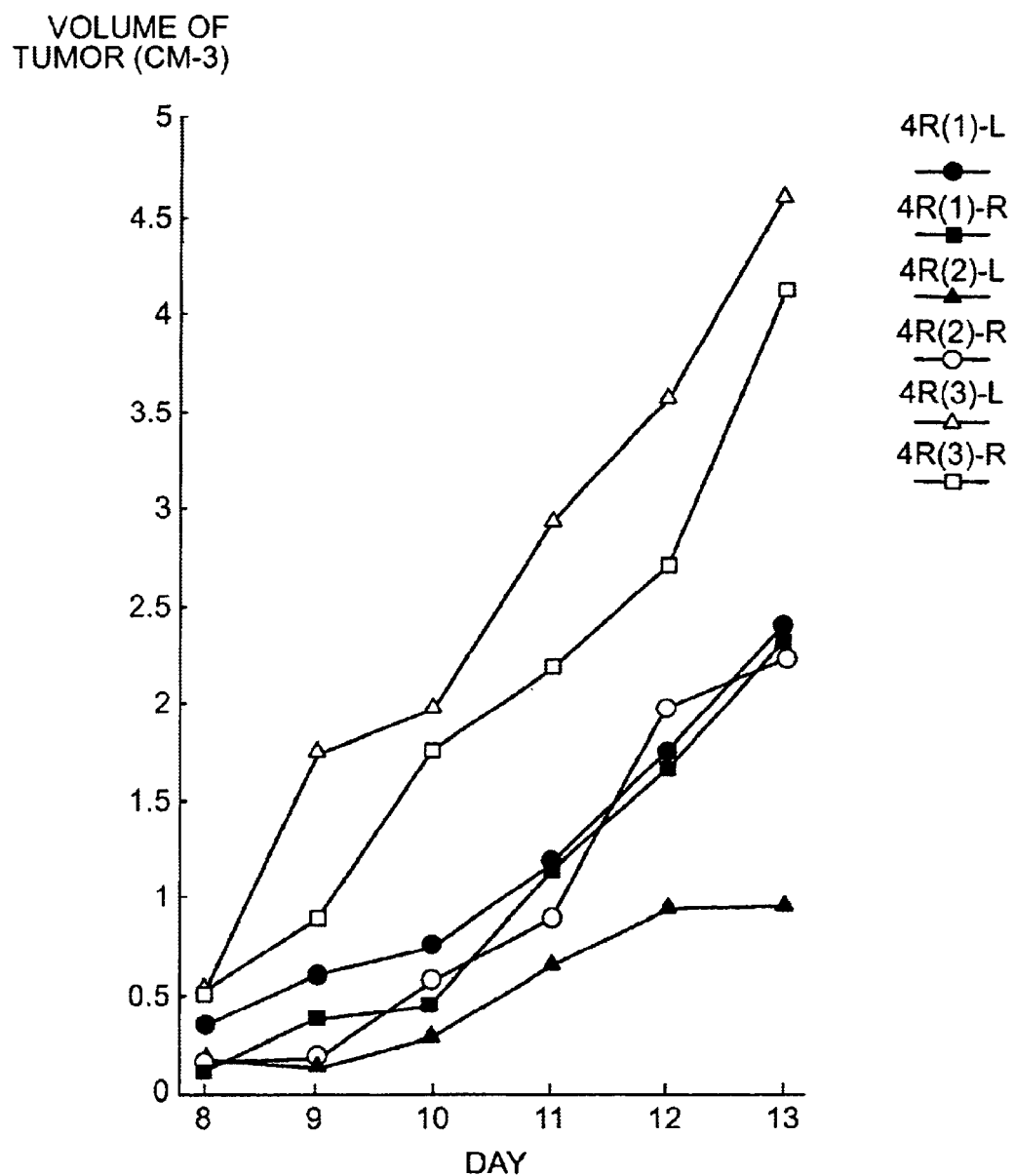

The ability of clone 8.60 cells to form tumor after subcutaneous injection in nude mice was also examined (Table 13A). The clone 8.60 cells were tumorigenic, but in comparison to the parental 4R cells, a marked reduction in tumor growth rate and in the histological aspect of the tumors was observed. Primary tumors derived from clone 8.60 cells appeared as small nodules (0.1 to 0.5 cm$^3$) at the same time as nodules derived from 4R cells (8 days), but had significantly slower growth rates (FIG. 30A) than the rates of the parental 4R cells (FIG. 30B) as measured by tumor volume. Tumor volume was determined as follows. Parent 4R cells and clone 8.60 cells were injected ($10^5$ cells in 0.05 ml of phosphate buffered saline) subcutaneously in each flank of nu/nu mice. After appearance of a small nodule (0.1 to 0.5 $cm^3$) on day 8 the size of the tumor was measured daily with a caliper and the tumor volumes were calculated from 3 dimensions [Tomayko and Reynolds, Cancer Chemother. Pharmacol. 24, 148 (1990)]. As seen in FIG. 30, thirteen days after injection the average tumor size was 2.72 $cm^3 \pm 1.3$ for tumors derived from 4R cells and 0.68 $cm^3 \pm 0.65$ for tumors derived from 8.60 cells. At this time the animals were sacrificed and the tumors were resected and analyzed microscopically. The 4R-derived and clone 8.60-derived tumors showed a striking difference in their invasiveness in vivo. The 4R-derived tumors had invaded the muscle of the abdominal wall and the peritoneal cavity of the animals. However, clone 8.60-derived tumors were completely confined to the subcutaneous tissue and were circumscribed by a capsule of dense connective tissue and collagen fibers so that they were easily resected and separated from the muscle layer. Thus the clone 8.60-derived tumors were much less invasive than the 4R-derived tumors.

BFU-E (burst forming units-erythroid) [Dukes et al., Experimental Hematology 13, 59–66 (1985)]. Peripheral blood was obtained from a normal volunteer donor and heparinized. Mononuclear cells were removed by centrifugation on Ficoll-Hypaque (Pharmacia) at 400×g for 30 min. Cells were cultured at $4.1 \times 10^5$ cells per 35 mm dish in Iscove's modification of Dulbecco's medium, containing 0.8% (w/v) methyl cellulose, 30% (v/v) fetal calf serum, and 1.27 U/ml erythropoietin (AM-EPO, PC grade recombinant; Amgen Inc.). The recombinant human MI (derived from CHO cells; prepared as described in Example 10) was added at the indicated concentrations (Table 14) prior to plating the cells. After 10 days of incubation in a humidified atmosphere of 95% air-5% $CO_2$ at 37° C., colonies consisting of 3 or more subcolonies of erythroid cells or large single accumulations of erythroid cells (>300 cells) were scored as BFU-derived colonies. For each BFU-E determination, the colonies in the central 20% of the volume of 5 replicate dishes were counted. Results are given in Table 14.

TABLE 13A

In vitro and in vivo characteristics of 4R cells and 4R cells transfected with pcDNA HMI and pY3

| Clone | Secreted Inhibitory Activity (a) mU/$10^6$ cells | Secreted Collagenase Activity (b) | | Doubling Time (c) h | Tumor (d) | Metastatic Potential (e) Mean ± SEM |
|---|---|---|---|---|---|---|
| | | Type I μg/$10^6$ cells | Type IV ng/$10^6$ cells | | | |
| Parent cells | none | 189 ± 1.6 | 158 ± 10.6 | 19.2 | 8/8 | 234 ± 11 (10) |
| 4.6 | none | 112.2 ± 9.5 | 597 ± 12.1 | 18.0 | 8/8 | 175 ± 16(11) |
| 4.17 | none | 70.5 ± 22 | 123 ± 14.6 | 15.6 | 8/8 | 483 ± 32(11) |
| 8.27 | 1,103 | 7.42 ± 52 | 19.5 ± 0 | 16.8 | 8/8 | 391 ± 19(11) |
| 8.39 | 518 | 2.16 ± 03 | 8.7 ± 4.2 | 19.2 | 8/8 | 150 ± 14(11) |
| 8.60 | 6,285 | 3.54 ± 2.8 | 4.5 ± 6.4 | 15.6 | 8/8 | 80 ± 20(11) |
| 8.68 | 719 | 6.12 ± 1.8 | 25.2 ± 5.9 | 18.0 | 8/8 | 295 ± 33(10) |
| 8.71 | none | 24.8 ± 9.7 | 119.7 ± 3.3 | 19.2 | 8/8 | 351 ± 37(10) |

Table 13A (continued). In vitro and in vivo characteristics of 4R cells and 4R cells transfected with pcDNA HMI and pY3.
a. Free inhibitory activity in serum-free conditioned medium was determined toward rabbit fibroblast interstitial collagenase (Example 1, section 2).
b. Values represent amount of collagen degraded over 24 h at 37° C. Data points represent mean±SD of triplicate samples, and were corrected for cell numbers.
c. Doubling time was calculated from growth curves obtained from cultures of cells plated at $10^4$ cells per dish in 35 mm tissue culture dishes. Values represent the doubling time measured during the exponential phase of growth.
d. Tumor cells were injected at $5 \times 10^5$ (4 injections) and $1.2 \times 10^5$ (4 injections) subcutaneously in athymic (nude) mice and animals were observed for the formation of tumors. Data represent number of tumors formed per number of injections. In all animals tumors were detected within 10 days.
e. Data represent mean number of lung nodules±SE. Numbers in parentheses represent total number of animals injected during two separate experiments.

EXAMPLE 13
Hematopoietic Activity of Recombinant Human Metalloproteinase Inhibitor.

Erythroid potentiating activity of recombinant human MI was demonstrated using a one-stage in vitro assay for

TABLE 14

BFU-E potentiating activity of CHO cell-derived recombinant human MI

| | MI concentration (nM) | Number of BFU-E colonies | Mean number of colonies (± standard error) |
|---|---|---|---|
| Experiment 1 | 0 | 10, 6, 5, 6, 5 | 6.4 ± 0.94 |
| | 0.001 | 7, 4, 4, 9, 5 | 5.8 ± 0.98 |
| | 0.01 | 10, 8, 8, 4, 9 | 7.8 ± 1.03 |
| | 0.1 | 4, 8, 5, 5, 5 | 5.4 ± 0.68 |
| | 1.0 | 14, 11, 11, 8, 9 | 10.6 ± 1.04 |
| | 10.0 | 5, 12, 12, 17, 11 | 11.4 ± 1.94 |
| Experiment 2 | 0 | 4, 3, 2, 4, 3 | 3.2 ± 0.38 |
| | 0.01 | 4, 3, 3, 3, 3 | 3.2 ± 0.2 |
| | 0.1 | 3, 3, 2, 4, 4 | 3.2 ± 0.38 |
| | 1.0 | 9, 11, 7, 5, 6 | 7.6 ± 1.09 |
| | 10.0 | 7, 10, 12, 8, 5 | 8.4 ± 1.23 |
| | 100.0 | 7, 6, 6, 7, 8 | 6.8 ± 0.83 |

The activity is evident for MI concentrations $\geq 1$ nM in the assay.

Figure 31A:
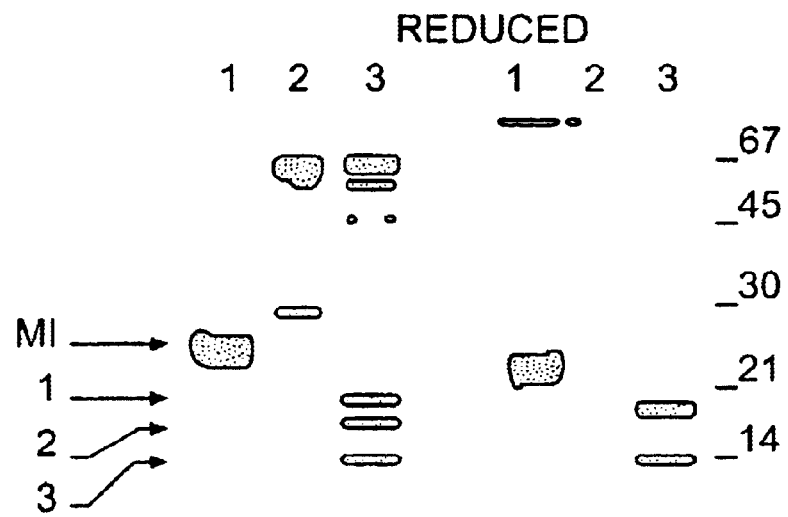
FIGS. 31A and B show results of plasmin digestion of MI.
Figure 31B:
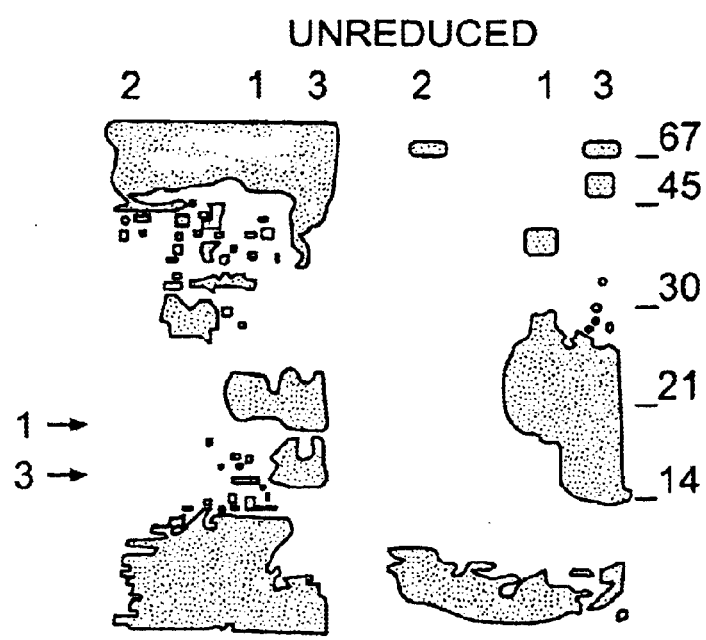
Figure 33:
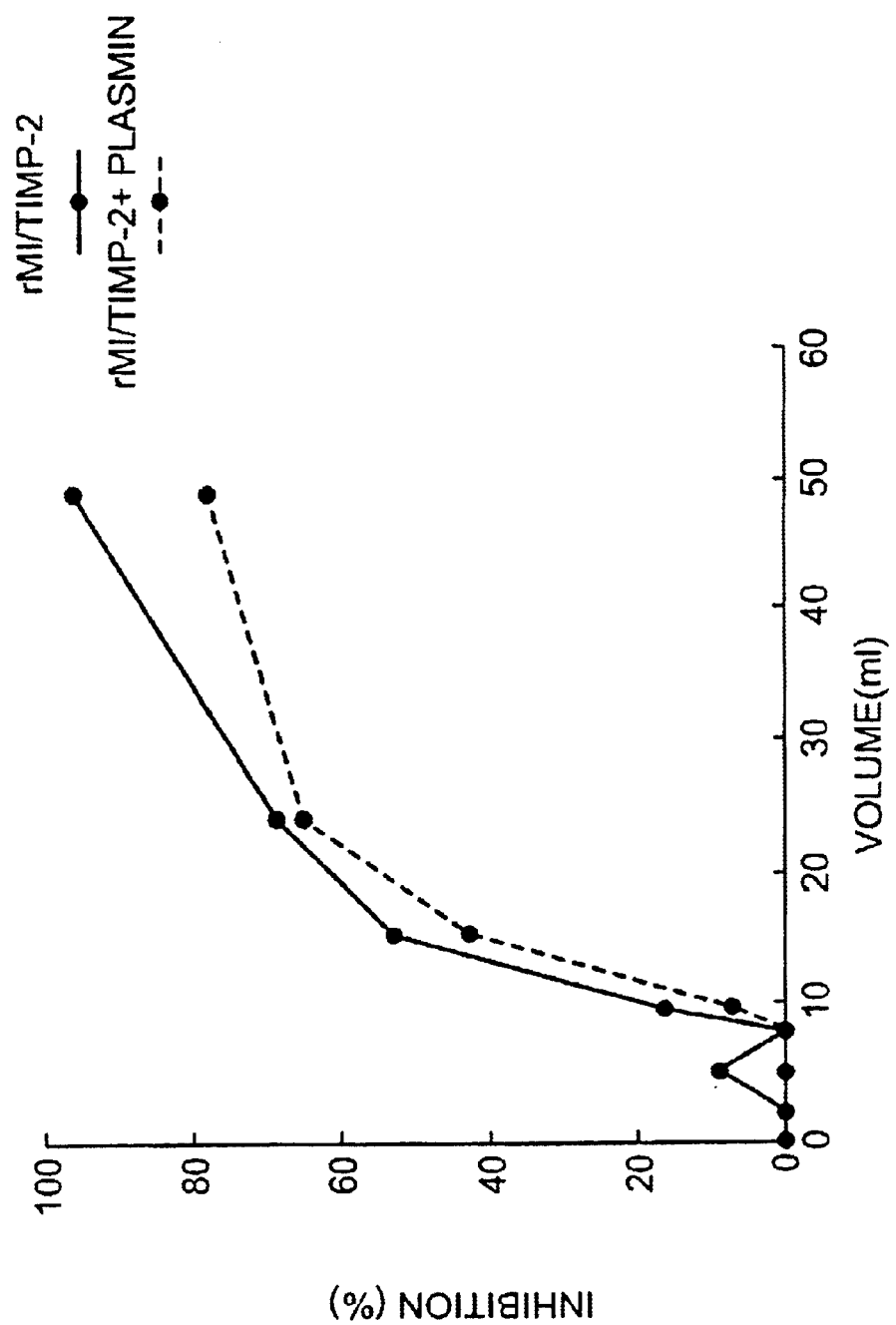
FIG. 33 shows inhibition of collagenase by human MI and by human MI digested with plasmin.

EXAMPLE 14
Production of Active MI Fragments
1. In an attempt to identify regions of the MI molecule potentially involved in different functions, limited proteolytic digestion of CHO cell-derived recombinant human MI was performed and the peptides obtained were analyzed. The results of digestion with plasmin are given in FIG. 31. MI (1.1 μg=50 pmol) was incubated with plasmin (37 μg=50 pmol) at 37° C. for 1 h in 5 μl of 50 mM Tris, 200 mM NaCl, 10 mM CaCl$_2$, pH 7.5. After incubation, samples were analysed by SDS-PAGE with (FIG. 31A) or without (FIG. 31B) reduction by 50 mM dithiothreitol. The gels in FIG. 31A left, FIG. 31A right, and FIG. 31B left are SDS-polyacrylamide gradient gels (5–15% acrylamide); the gel in FIG. 31B right is a SDS-gelatin substrate gel. After electrophoresis, gels were processed as follows: FIG. 31A left, silver stained; FIG. 31A right, Western blot as described in Example 1, Section 4 using a rabbit polyclonal antiserum against MI and peroxidase conjugated goat serum against rabbit IgG; FIG. 31B left, silver-stained; FIG. 31B right, SDS-gelatin substrate gel stained with Coomassie blue after digestion of the gelatin with crude gelatinase (see Example 1, Section 4; dense zones represent proteins with antigelatinase activity). For each gel: lane 1, MI (1.1 μg); lane 2, plasmin (3.7 μg); lane 3, MI and plasmin. It can be seen that proteolytic digestion of MI by plasmin resulted in the formation of three products with M$_r$ of 19 kDa (peptide 1), 17 kDa (peptide 2) and 13.5 kDa (peptide 3) identified by SDS-PAGE run under reducing conditions (FIG. 31A left). Only peptides 1 and 3 were recognized by an anti-MI polyclonal antibody by SDS-PAGE with immunoblot analysis (FIG. 31A right). When electrophoresed in the absence of reducing agent, peptides 1 and 3 migrated more slowly, with apparent M$_r$ of 20 kDa and 14.5 kDa, respectively (FIG. 31B left). These peptides retained their anticollagenase activity as shown by the SDS-gelatin PAGE (FIG. 31B right). N-terminal amino acid sequencing (see Example 2) indicated that peptides 1 and 3 retain the amino-terminal region of MI, and that peptide 2 is a fragment of plasmin (FIG. 32). After electrophoresis and quick stain with Coomassie blue, bands were electroblotted onto polyvinylidene difluoride membrane [Sambrook et al. (1989) Molecular Cloning. A Laboratory Manual] and sequenced. Bands 1, 2 and 3 correspond to the three peptides indicated at the left margin of FIG. 31A. From these data it is apparent that MI is relatively resistant to proteolytic degradation by plasmin [or trypsin; see Cawston et al. J. Biochem. 195, 159–165 (1981); Murphy et al. J. Biochem. 195, 167–170 (1981)]. This was further confirmed by showing that incubation of MI with plasmin does not result in a significant loss of inhibitory activity (FIG. 33). In the experiment of FIG. 33, MI (0.55 μg=25 pmol) was incubated with plasmin for 1 h at 37° C. The reaction was then blocked by addition of soybean trypsin inhibitor (9.5 pg). Aliquots of the mixture were then tested for inhibitory activity against interstitial collagenase (70 mU; see Example 1, section 2) in comparison with the inhibitory activity of aliquots containing similar concentrations of undigested MI.

Plasmin and trypsin cleave proteins at Lys or Arg residues. MI contains 23 Lys plus Arg residues. The limited digestion of MI by plasmin indicates that many of the Lys and Arg residues are inaccessible to plasmin because of the structure of MI, which probably includes six disulfide bonds. This interpretation is supported by the finding that reduced-alkylated MI is much more susceptible to digestion by plasmin (i.e., no large peptides remain as judged by SDS-PAGE).

Figure 34:
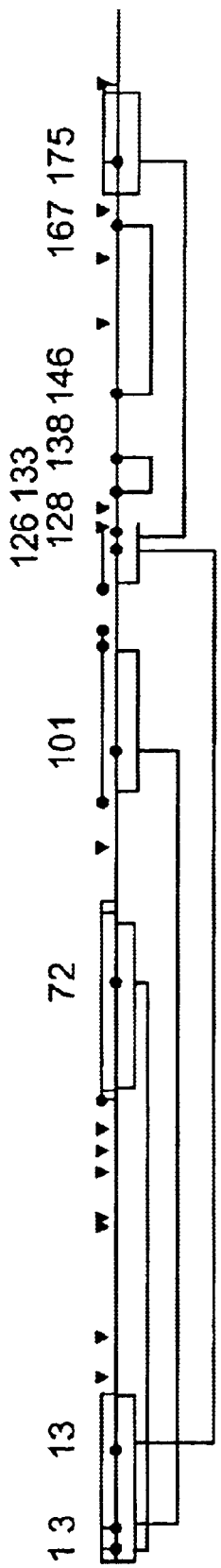
FIG. 34 is a linear diagram of human MI showing the presence of Lys and Arg residues (arrows) and theoretical assignment of the 6 disulfide bonds. Numbers on top indicate positions of Cys residues.

The apparent size of peptide 3 by SDS-PAGE (14.5 kDal; FIG. 31) suggests that it contains about 130–135 amino acids. Since it retains the N-terminal region, it would correspond to amino acids 1–130/135 of MI. By SDS-PAGE using gels with high percentage acrylamide, a small (2.5 kDal) fragment could be visualized in plasmin digests of MI. This fragment had the N-terminal sequence (Cys)-Pro-Met-Ile-Pro-(Cys)-Tyr-Ile-Ser-Ser-Pro-Xaa-Glu- (SEQ ID No: 1), i.e., it starts at residue 133 of MI (see FIG. 2), and results from cleavage by plasmin of the bond between Arg 132 and Cys 133. It is likely that the 2.5 kDal fragment extends to residue Arg 170, and that after plasmin treatment under non-reducing conditions, the fragment representing amino acids 171–194 remains attached to the 1–132 fragment via a disulfide bond between Cys 128 and Cys 175. This suggestion is based on the likelihood that human MI has the same disulfide structure as human TIMP [Williamson et al., Biochem. J. 268, 267–274 (1990)]. The theoretical disulfide structure for human MI is shown in linearized fashion in FIG. 34. The numbers in FIG. 34 indicate the positions of Cys residues and the brackets indicate disulfide linkages inferred by analogy to those present in TIMP and probably MI as well. The arrowheads indicate positions of Lys and Arg residues. Note that the fragment 133–170 produced by plasmin cleavage has two internal disulfide bonds (Cys 133-Cys 138 and Cys 146-Cys 167) but no covalent linkages to fragment 1–132 or fragment 171–194. As suggested above, the disulfide bond Cys 128-Cys 175 would keep fragments 1–132 and 171–194 covalently linked after excision of fragment 133–170 by plasmin.

The data presented show that the N-terminal portion of MI (residues 1–132) is sufficient for the anticollagenase activity.

2. Dissection of Functional Domains of MI.

It is possible that the different specific functions of MI could involve different portions of the molecule. These specific functions include 1) binding to activated metalloproteinase, 2) inhibition of activated metalloproteinase, 3) binding to metalloproteinase proenzyme, 4) inhibition of autoproteolytic activation of proenzyme. Various approaches are taken to ascertain whether different regions of MI are involved in these functions.

a. Isolation of Peptides.

Proteolytically-generated peptides are isolated by reverse phase chromatography (e.g., using a C-18 column and acetonitrite gradient; see Williamson et al., Biochem J., 1990, supra) or gel filtration chromatography to preserved their function. These fragments are tested for their ability to carry out the specific functions listed above, using methods outlined in previous Examples.

b. Mutations.

Deletion mutation is used to confirm the functional role of the N-terminal portion of MI and site-directed mutagenesis is used to investigate the role of specific cysteine residues in maintaining the stability and the activity of the molecule. cDNAs with deletions corresponding to the C-terminal end of MI were prepared using controlled exonucleotic cleavage of MI cDNA by exonuclease III. Alternatively, a cDNA with deletion of codons for amino acids 135 to 194 was obtained from the NcoI-StuI human MI cDNA using a unique Nla III restriction site [C ATG↓ located at codon −26 (Methionine) and codon 135 (Methionine). A linker with a termination codon was then inserted and these constructs were reinserted into a pcDNA vector by blunt end ligation. This vector is suitable for expression in rat embryo cells and CHO cells. The vector was transfected into CHO cells and tested for transient expression. Alternatively, a pcD vector containing a SV40 promoter, splicing and polyadenylation sequences suitable for expression in COS cells is used [Okayama and Berg, Mol. Cell. Biol. 3, 280–289 (1983)]. If needed, stable expression is obtained by co-transfection with plasmid pY3 containing the hygromycin B phosphotransferase gene [Blocklinger and Diegelman, Mol. Cell. Biol. 4,2929–2931 (1984)] and transfected cells are selected for resistance to hygromycin B (0.4 mg/ml) (see Example 12).

Site-directed mutagenesis was achieved by oligonucleotide-directed mutagenesis using the dual primer method described by Zoller and Smith [Methods Enzymol. 154,329–240 (1987)]. Substitution of serine or alanine for individual cysteine residues allows the elimination of individual disulfide bonds without chemical reduction of the protein [Schultz et al., Proteins: Structure, Function and Genetics 2,290–297 (1987)]. For example, individual substitution of Cys 175, Cys 168 and Cys 138 allows determination of the importance of each of the 3 disulfide bonds of the C-terminal portion of MI and examination of the influence of the structure of this domain on the stability and function of the molecule. Comparison between deletion mutants and mutants involving cysteine substitutions indicates whether the tertiary structure of the C-terminal portion has any influence on the tertiary structure and function of the N-terminal portion.

While the present invention has been described in terms of preferred embodiments, it is understood that variations and modifications will occur to those skilled in the art. Therefore, it is intended that the appended claims cover all such equivalent variations which come within the scope of the invention as claimed.

What is claim is:

1. An isolated and purified antibody, wherein said antibody binds specifically to a polypeptide comprising an amino acid sequence SEQ ID NO: 7 or SEQ ID NO: 9.

2. The antibody according to claim 1, wherein said antibody is a monoclonal antibody.

3. The antibody according to claim 1, comprising a detectable label.

4. A hybridoma cell secreting an antibody according to claim 2.

* * * * *

UNITED STATES PATENT AND TRADEMARK OFFICE
CERTIFICATE OF CORRECTION

PATENT NO.     : 6,849,450 B2
DATED          : February 1, 2005
INVENTOR(S)    : Keith E. Langley et al.

It is certified that error appears in the above-identified patent and that said Letters Patent is hereby corrected as shown below:

Title page,
Item [73], Assignees, "Thousands Oaks," should read -- Thousand Oaks, --.

Column 67,
Line 51, "What is claim is:" should read -- What is claimed is: --.

Signed and Sealed this

Seventeenth Day of May, 2005

JON W. DUDAS
*Director of the United States Patent and Trademark Office*

```
                         SEQUENCE LISTING

<160> NUMBER OF SEQ ID NOS: 36

<210> SEQ ID NO 1
<211> LENGTH: 13
<212> TYPE: PRT
<213> ORGANISM: Homo sapiens

<400> SEQUENCE: 1

Cys Pro Met Ile Pro Cys Tyr Ile Ser Ser Pro Asp Glu
 1               5                  10

<210> SEQ ID NO 2
<211> LENGTH: 19
<212> TYPE: PRT
<213> ORGANISM: Homo sapiens

<400> SEQUENCE: 2

Cys Ser Cys Ser Pro Val His Pro Gln Gln Ala Phe Cys Asn Ala Asp
 1               5                  10                  15

Val Val Ile

<210> SEQ ID NO 3
<211> LENGTH: 20
<212> TYPE: PRT
<213> ORGANISM: Homo sapiens

<400> SEQUENCE: 3

Val Val Phe Phe Pro Val Ala His Pro His Ser Trp Pro Thr Gln Val
 1               5                  10                  15

Ser Leu Arg Thr
            20

<210> SEQ ID NO 4
<211> LENGTH: 21
<212> TYPE: PRT
<213> ORGANISM: Homo sapiens

<400> SEQUENCE: 4

Val Val Gly Gly Pro Ala Val Ala His Pro His Ser Trp Pro Thr Gln
 1               5                  10                  15

Val Ser Leu Arg Thr
            20

<210> SEQ ID NO 5
<211> LENGTH: 6
<212> TYPE: PRT
```

-continued

<213> ORGANISM: Homo sapiens

<400> SEQUENCE: 5

Cys Ser Cys Ser Pro Val
 1               5

<210> SEQ ID NO 6
<211> LENGTH: 1045
<212> TYPE: DNA
<213> ORGANISM: Bos taurus

<400> SEQUENCE: 6

```
aattccggct tctatggagc actcgggacc aggtccgcgg cgcgcgcact cgctcgctcg      60
ccgcccccca gccagctctc gcttccgcgc cgccagccgc gccccgcgcc tcctcgctgc     120
accccgcgac ctagagccaa gaaagtttgt gtggcgagtg agggccggag aggagagcgc     180
gcccgcggag tgccgtccag accagcgcgg ccccggcgga gagggagcg ccccgagccc      240
aggcggcggc ggctagcccg agtccgcgac ccccgcccct ccgcccgcca tgggcgccgc     300
cgcccgcagc ctgccgctcg cgttctgcct cctgctgctg gggacgctgc tcccccgggc     360
cgacgcctgc agctgctccc cggtgcaccc gcaacaggcg ttttgcaatg cagacatagt     420
gatcagggcc aaagcagtca ataagaagga ggtggactct ggcaacgaca tctacggcaa     480
ccccatcaag cggattcagt atgagatcaa gcagataaag atgttcaagg acctgatca     540
ggacatagag tttatctaca cagccccgc cgctgccgtg tgtggggtct cgctggacat     600
tggaggaaag aaggagtatc tcattgcagg gaaggccgag gggaatggca atatgcatat     660
caccctctgt gacttcatcg tgccctggga caccctgagt gccacccaga gaagagcct     720
gaaccacagg taccagatgg gctgtgagtg caagatcact cgatgcccca tgatcccatg     780
ctacatctcc tctccggacg agtgcctctg gatggactgg gtcacggaga gaacatcaa     840
cggacaccag gccaagttct tcgcctgcat caagagaagc gacggctcct gcgcctggta     900
ccgcggagca gcaccccca agcaggagtt tctggacatg aggacccgta agcaggccac     960
caggactcct ggggccaatt gacagtgtcc aagagttcag actggtccag ctccgacatc    1020
ccttcctgga cacagcatga ataaa                                           1045
```

<210> SEQ ID NO 7
<211> LENGTH: 220
<212> TYPE: PRT
<213> ORGANISM: Bos taurus

<400> SEQUENCE: 7

Met Gly Ala Ala Ala Arg Ser Leu Pro Leu Ala Phe Cys Leu Leu Leu
 1               5                  10                  15

Leu Gly Thr Leu Leu Pro Arg Ala Asp Ala Cys Ser Cys Ser Pro Val
                20                  25                  30

His Pro Gln Gln Ala Phe Cys Asn Ala Asp Ile Val Ile Arg Ala Lys
            35                  40                  45

Ala Val Asn Lys Lys Glu Val Asp Ser Gly Asn Asp Ile Tyr Gly Asn
        50                  55                  60

Pro Ile Lys Arg Ile Gln Tyr Glu Ile Lys Gln Ile Lys Met Phe Lys
    65                  70                  75                  80

Gly Pro Asp Gln Asp Ile Glu Phe Ile Tyr Thr Ala Pro Ala Ala Ala
                85                  90                  95

Val Cys Gly Val Ser Leu Asp Ile Gly Gly Lys Lys Glu Tyr Leu Ile
               100                 105                 110

```
Ala Gly Lys Ala Glu Gly Asn Gly Asn Met His Ile Thr Leu Cys Asp
        115                 120                 125

Phe Ile Val Pro Trp Asp Thr Leu Ser Ala Thr Gln Lys Lys Ser Leu
    130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala
        195                 200                 205

Pro Pro Lys Gln Glu Phe Leu Asp Ile Glu Asp Pro
    210                 215                 220

<210> SEQ ID NO 8
<211> LENGTH: 1032
<212> TYPE: DNA
<213> ORGANISM: Homo sapiens

<400> SEQUENCE: 8
attccggccc gccgtccccc accccgccgc cccgcccggc gaattgcgcc ccgcgcccct      60
cccctcgcgc ccccgagaca agaggagag aagtttgcgc ggccgagcgg ggcaggtgag      120
gagggtgagc cgcgcgggag gggcccgcct cggccccggc tcagccccg cccgcgcccc      180
cagcccgccg ccgcgagcag cgcccggacc ccccagcggc ggccccgcc cgcccagccc      240
cccggcccgc catgggcgcc gcggcccgca ccctgcggct ggcgctcggc ctcctgctgc      300
tggcgacgct gcttcgcccg ccgacgcct gcagctgctc cccggtgcac ccgcaacagg      360
cgttttgcaa tgcagatgta gtgatcaggg ccaaagcggt cagtgagaag gaagtggact      420
ctggaaacga catttatggc aaccctatca gaggatcca gtatgagatc aagcagataa      480
agatgttcaa agggcctgag aaggatatag agtttatcta cacggccccc tcctcggcag      540
tgtgtgggt ctcgctggac gttggaggaa agaaggaata tctcattgca ggaaaggccg      600
agggggacgg caagatgcac atcaccctct gtgacttcat cgtgccctgg gacacctga      660
gcaccaccca gaagaagagc ctgaaccaca ggtaccagat gggctgcgag tgcaagatca      720
cgcgctgccc catgatcccg tgctacatct cctccccgga cgagtgcctc tggatggact      780
gggtcacaga gaagaacatc aacgggcacc aggccaagtt cttcgcctgc atcaagaaga      840
gtgacggctc ctgtgcgtgg taccgcggcg cggcgccccc caagcaggag tttctcgaca      900
tcgaggaccc ataagcaggc ctccaacgcc cctgtggcca actgcaaaaa aagcctccaa      960
gggtttcgac tggtccagct ctgacatccc ttcctggaaa cagcatgaat aaaacactca      1020
tccccggaat tc                                                         1032

<210> SEQ ID NO 9
<211> LENGTH: 220
<212> TYPE: PRT
<213> ORGANISM: Homo sapiens

<400> SEQUENCE: 9

Met Gly Ala Ala Ala Arg Thr Leu Arg Leu Ala Leu Gly Leu Leu Leu
  1               5                  10                  15

Leu Ala Thr Leu Leu Arg Pro Ala Asp Ala Cys Ser Cys Ser Pro Val
             20                  25                  30
```

```
His Pro Gln Gln Ala Phe Cys Asn Ala Asp Val Val Ile Arg Ala Lys
        35                  40                  45

Ala Val Ser Glu Lys Glu Val Asp Ser Gly Asn Asp Ile Tyr Gly Asn
 50                  55                  60

Pro Ile Lys Arg Ile Gln Tyr Glu Ile Lys Gln Ile Lys Met Phe Lys
 65                  70                  75                  80

Gly Pro Glu Lys Asp Ile Glu Phe Ile Tyr Thr Ala Pro Ser Ser Ala
                 85                  90                  95

Val Cys Gly Val Ser Leu Asp Val Gly Gly Lys Lys Glu Tyr Leu Ile
                100                 105                 110

Ala Gly Lys Ala Glu Gly Asp Gly Lys Met His Ile Thr Leu Cys Asp
            115                 120                 125

Phe Ile Val Pro Trp Asp Thr Leu Ser Thr Thr Gln Lys Lys Ser Leu
        130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
                180                 185                 190

Cys Ile Lys Arg Ser Asp Gly Ser Cys Ala Trp Tyr Arg Gly Ala Ala
            195                 200                 205

Pro Pro Lys Gln Glu Phe Leu Asp Ile Glu Asp Pro
        210                 215                 220

<210> SEQ ID NO 10
<211> LENGTH: 45
<212> TYPE: PRT
<213> ORGANISM: Bos taurus

<400> SEQUENCE: 10

Cys Ser Cys Ser Pro Cys His Pro Gln Gln Ala Phe Cys Asn Ala Asp
 1               5                  10                  15

Ile Val Ile Arg Ala Lys Ala Val Asn Lys Lys Glu Val Asp Ser Gly
            20                  25                  30

Asn Asp Ile Tyr Gly Asn Pro Ile Lys Arg Lys Gln Tyr
            35                  40                  45

<210> SEQ ID NO 11
<211> LENGTH: 49
<212> TYPE: PRT
<213> ORGANISM: Bos taurus

<400> SEQUENCE: 11

Cys Thr Cys Val Pro Pro His Pro Gln Thr Ala Phe Cys Asn Ser Asp
 1               5                  10                  15

Val Val Ile Arg Ala Lys Phe Val Gly Thr Ala Glu Val Asn Glu Thr
            20                  25                  30

Ala Leu Leu Tyr Arg Tyr Leu Ile Lys Met Leu Lys Met Pro Ser Gly
            35                  40                  45

Phe

<210> SEQ ID NO 12
<211> LENGTH: 49
<212> TYPE: PRT
<213> ORGANISM: Homo sapiens
```

```
<400> SEQUENCE: 12

Cys Thr Cys Val Pro Pro His Pro Gln Thr Ala Phe Cys Asn Ser Asp
 1               5                  10                  15

Leu Val Ile Arg Ala Lys Phe Val Gly Thr Pro Glu Val Asn Gln Thr
            20                  25                  30

Thr Leu Tyr Gln Arg Tyr Glu Ile Lys Met Thr Lys Met Tyr Lys Gly
        35                  40                  45

Phe

<210> SEQ ID NO 13
<211> LENGTH: 49
<212> TYPE: PRT
<213> ORGANISM: Bos taurus

<400> SEQUENCE: 13

Cys Thr Cys Val Pro Pro His Pro Gln Thr Ala Phe Cys Asn Ser Asp
 1               5                  10                  15

Val Val Ile Arg Ala Lys Phe Val Gly Thr Ala Glu Val Asn Glu Thr
            20                  25                  30

Ala Leu Leu Tyr Arg Tyr Leu Ile Lys Met Leu Lys Met Pro Ser Gly
        35                  40                  45

Phe

<210> SEQ ID NO 14
<211> LENGTH: 45
<212> TYPE: PRT
<213> ORGANISM: Bos taurus

<400> SEQUENCE: 14

Cys Ser Cys Ser Pro Val His Pro Gln Gln Ala Phe Cys Asn Ala Asp
 1               5                  10                  15

Ile Val Ile Arg Ala Lys Ala Val Asn Lys Lys Glu Val Asp Ser Gly
            20                  25                  30

Asn Asp Ile Tyr Gly Asn Pro Ile Lys Arg Ile Gln Tyr
        35                  40                  45

<210> SEQ ID NO 15
<211> LENGTH: 45
<212> TYPE: DNA
<213> ORGANISM: Bos taurus

<400> SEQUENCE: 15
gatcacaatg tcagcattgc agaaggcctg ctggggatgc acagg              45

<210> SEQ ID NO 16
<211> LENGTH: 30
<212> TYPE: DNA
<213> ORGANISM: Artificial Sequence
<220> FEATURE:
<221> NAME/KEY: modified_base
<222> LOCATION: (4)
<223> OTHER INFORMATION: i
<220> FEATURE:
<221> NAME/KEY: modified_base
<222> LOCATION: (19)
<223> OTHER INFORMATION: i
<220> FEATURE:
<221> NAME/KEY: modified_base
<222> LOCATION: (22)
<223> OTHER INFORMATION: i
<220> FEATURE:
<221> NAME/KEY: modified_base
<222> LOCATION: (28)
```

```
<223> OTHER INFORMATION: i
<220> FEATURE:
<223> OTHER INFORMATION: Description of Artificial Sequence:
      oligonucleotide

<400> SEQUENCE: 16
gtcnacytcy ttyttgttna cngcyttngc                                    30

<210> SEQ ID NO 17
<211> LENGTH: 30
<212> TYPE: DNA
<213> ORGANISM: Artificial Sequence
<220> FEATURE:
<221> NAME/KEY: modified_base
<222> LOCATION: (4)
<223> OTHER INFORMATION: i
<220> FEATURE:
<221> NAME/KEY: modified_base
<222> LOCATION: (7)
<223> OTHER INFORMATION: i
<220> FEATURE:
<221> NAME/KEY: modified_base
<222> LOCATION: (13)
<223> OTHER INFORMATION: i
<220> FEATURE:
<221> NAME/KEY: modified_base
<222> LOCATION: (17)
<223> OTHER INFORMATION: i
<220> FEATURE:
<221> NAME/KEY: modified_base
<222> LOCATION: (26)
<223> OTHER INFORMATION: i
<220> FEATURE:
<223> OTHER INFORMATION: Description of Artificial Sequence:
      oligonucleotide

<400> SEQUENCE: 17
cttnatnggr ttnccrtana trtcrttncc                                    30

<210> SEQ ID NO 18
<211> LENGTH: 51
<212> TYPE: DNA
<213> ORGANISM: Bos taurus

<400> SEQUENCE: 18
cgggtcctcg atgtccagaa actcctgctt gggggtgct gctccgcggt a              51

<210> SEQ ID NO 19
<211> LENGTH: 48
<212> TYPE: DNA
<213> ORGANISM: Bos taurus

<400> SEQUENCE: 19
gaacttggcc tggtgtccgt tgatgttctt ctccgtgacg tccatcca                 48

<210> SEQ ID NO 20
<211> LENGTH: 51
<212> TYPE: DNA
<213> ORGANISM: Bos taurus

<400> SEQUENCE: 20
cgcctcacag cccatctggt acctgtggtt caggctcttc ttctgggtgg c             51

<210> SEQ ID NO 21
<211> LENGTH: 48
<212> TYPE: DNA
<213> ORGANISM: Bos taurus

<400> SEQUENCE: 21
```
ggggttgccg tagatgtcgt tgccagagtc ctccttctta ttgactgc        48

<210> SEQ ID NO 22
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
cgatttgatt ctagaaggag gaataacata tggttaacgc gttggaattc ggtac        55

<210> SEQ ID NO 23
<211> LENGTH: 49
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
taaactaaga tcttcctcct tattgtatac caattgcgca accttaagc        49

<210> SEQ ID NO 24
<211> LENGTH: 141
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
ctaattccgc tctcacctac caaacaatgc ccccctgcaa aaataaatt catataaaaa        60 acatacagat aaccatctgc ggtgataaat tatctctggc ggtgttgaca taaataccac       120
tggcggtgat actgagcaca t        141

<210> SEQ ID NO 25
<211> LENGTH: 147
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
tgcagattaa ggcgagagtg gatggtttgt tacgggggga cgttttttat ttaagtatat        60
tttttgtatg tctattggta gacgccacta tttaatagag accgccacaa ctgtatttat       120
ggtgaccgcc actatgactc gtgtagc        147

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 26

Met Arg Phe Pro Ser Ile Phe Thr Ala
 1               5

<210> SEQ ID NO 27

```
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
gatcacacat aaataaacaa aatgagattt ccttcaatt ttactgca                48

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
tgtgtattta tttgttttac tctaaaggaa gttaaaaatg                        40

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
agcttgcatg cgagctcccc gggctcgaga tctgataaca acagtgtaga tgtaacaaaa  60

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
acgtacgctc gagggggcccg agctctagac tattgttgtc acatctacat tgttttagct  60

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
aattcgatat cgatggtacc cgggatccgt cgacagatct g                     41

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
gctatagcta ccatgggccc taggcagctg tctagactta a                     41

<210> SEQ ID NO 33
<211> LENGTH: 55
```

```
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
cgatttgatt ctagaaggag gaataacata tggttaacgc gttggaattc ggtac          55

<210> SEQ ID NO 34
<211> LENGTH: 49
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
taaactaaga tcttcctcct tattgtatac caattgcgca accttaagc                49

<210> SEQ ID NO 35
<211> LENGTH: 156
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
ctagaaaaaa ccaaggaggt aataaataat gtgttcttgt tctcctgtac accctcaaca     60
agctttttgt aacgctgatg tagttatccg tgcaaaagct gtttctgaaa aagaagttga    120
ttctggtaac gacatctacg gtaacccgat caaaag                              156

<210> SEQ ID NO 36
<211> LENGTH: 156
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
ttttttggtt cctccattat ttattacaca agaacaagag gacatgtggg agttgttcga     60
aaaacattgc gactacatca ataggcacgt tttcgacaaa gacttttct tcaactaaga    120 ccattgctgt agatgccatt gggctagttt cctag                               156
```